US012681017B2

(12) United States Patent
Ebmeyer et al.

(10) Patent No.: US 12,681,017 B2
(45) Date of Patent: Jul. 14, 2026

(54) PRO-ADRENOMEDULLIN FOR PROGNOSING DISEASE PROGRESSION IN SEVERE ACUTE RESPIRATORY SYNDROME (SARS)

(71) Applicant: B.R.A.H.M.S GMBH, Hennigsdorf (DE)

(72) Inventors: Stefan Ebmeyer, Hoppegarten (DE); Manne Krop, Berlin (DE); Jutta Odarjuk, Berlin (DE)

( * ) Notice: Subject to any disclaimer, the term of this patent is extended or adjusted under 35 U.S.C. 154(b) by 810 days.

(21) Appl. No.: 17/916,993

(22) PCT Filed: Apr. 6, 2021

(86) PCT No.: PCT/EP2021/058885
§ 371 (c)(1),
(2) Date: Oct. 4, 2022

(87) PCT Pub. No.: WO2021/204770
PCT Pub. Date: Oct. 14, 2021

(65) Prior Publication Data
US 2023/0160893 A1 May 25, 2023

(30) Foreign Application Priority Data

| | | | |
|---|---|---|---|
| Apr. 6, 2020 | (EP) | ..................................... | 20168321 |
| Apr. 7, 2020 | (EP) | ..................................... | 20168591 |
| Jun. 12, 2020 | (EP) | ..................................... | 20179787 |
| Aug. 14, 2020 | (EP) | ..................................... | 20191084 |

(51) Int. Cl.
*G01N 33/569* (2006.01)
*G01N 33/74* (2006.01)

(52) U.S. Cl.
CPC ....... *G01N 33/56983* (2013.01); *G01N 33/74* (2013.01); *G01N 2333/165* (2013.01); *G01N 2800/12* (2013.01); *G01N 2800/52* (2013.01); *G01N 2800/56* (2013.01)

(58) Field of Classification Search
None
See application file for complete search history.

(56) References Cited

PUBLICATIONS

Morgenthaler et al. Clinical Chemistry, vol. 51, Issue 10, Oct. 1, 2005, pp. 1823-1829, https://doi.org/10.1373/clinchem.2005.051110 (Year: 2005).*

Spanish Respiratory Society Guidelines Archivos de Bronconeumología ((English Edition)) vol. 41, Issue 5, May 2005, pp. 272-289 https://doi.org/10.1016/S1579-2129(06)60222-X (Year: 2005).*

Reducing bacterial resistance with Impact Sixth Edition Pneumonia Severity Index (PSI) for Community Acquired Pneumonia (retrieved online https://impact.chp.gov.hk/calculator_4_2.php on Oct. 29, 2025) (Year: 2025).*

Saeed et al. Critical Care (2019) 23:40 https://doi.org/10.1186/s13054-019-2329-5 (Year: 2019).*

ThermoFisher News (retrieved online https://www.brahms.de/en-gb/news-media/news.html on Oct. 30, 2025) (Year: 2025).*

Wayback Machine (retrieved online Wayback Machine—Calendar of https://www.brahms.de/en-gb/news-media/news/covid-19-and-scarce-hospital-resources-brahms-mr-proadm-for-risk-stratification-to-support-decisions-on-the-required-level-of-care.html Oct. 30, 2025) (Year: 2025).*

Wayback Machine (retrieved online https://web.archive.org/web/20260000000000*/%20https://www.brahms.de/en-gb/news-media/news/covid-19-and-scarce-hospital-resources-brahms-mr-proadm-for-risk-stratification-to-support-decisions-on-the-required-level-of-care.html on Feb. 27, 2026) (Year: 2026).*

ThermoFisher News (retrieved online https://www.brahms.de/en-gb/news-media/news.html on Oct. 30, 2025) (Year: 2026).*

"COVID-19 and Scarce Hospital Resources: B.R.A.H.M.S MR-proADM for Risk Stratification to Support Decisions on the Required Level of Care," 2020; retrieved from the Internet on Jul. 14, 2020 at https://www.mrproadm.com/news-media/news/covid-19-and-scarce-hospital-resources-brahms-mr-proadm-for-risk-stratification-to-support-decisions-on-the-required-level-of-care/ (5 pages).

Baldirà et al., "Biomarkers and clinical scores to aid the identification of disease severity and intensive care requirement following activation of an in-hospital sepsis code," *Annals of Intensive Care*, 10:7, 2020 (11 pages).

Bello et al., "Prognostic power of proadrenomedullin in community-acquired pneumonia is independent of aetiology," *European Respiratory Journal*, vol. 39, pp. 114-1155, 2012.

International Search Report and Written Opinion issued in PCT/EP2021/058885 on Jun. 2, 2021 (13 pages).

Schuetz et al., "The prognostic blood biomarker proadrenomedullin for outcome prediction in patients with chronic obstructive pulmonary disease (COPD): a qualitative clinical review," *Clinical Chemistry and Laboratory Medicine*, vol. 53, pp. 521-539, 2015.

(Continued)

*Primary Examiner* — Gregory S Emch
*Assistant Examiner* — Fernando Ivich
(74) *Attorney, Agent, or Firm* — Klarquist Sparkman, LLP

(57) ABSTRACT

The invention relates to a method for prognosing disease progression in a patient that has or is at risk of developing a severe acute respiratory syndrome (SARS), wherein the method comprises determining a level of pro-adrenomedullin (proADM) or fragment(s) thereof in a sample from the patient, wherein said level indicates the severity of SARS progression. The method is in some embodiments configured for use when a patient exhibits symptoms of a severe acute respiratory syndrome (SARS), a patient exhibits symptoms of infection with a SARS-virus, the patient is infected with a SARS-virus, such as a SARS-coronavirus, such as SARS-CoV2.

Figure 1:
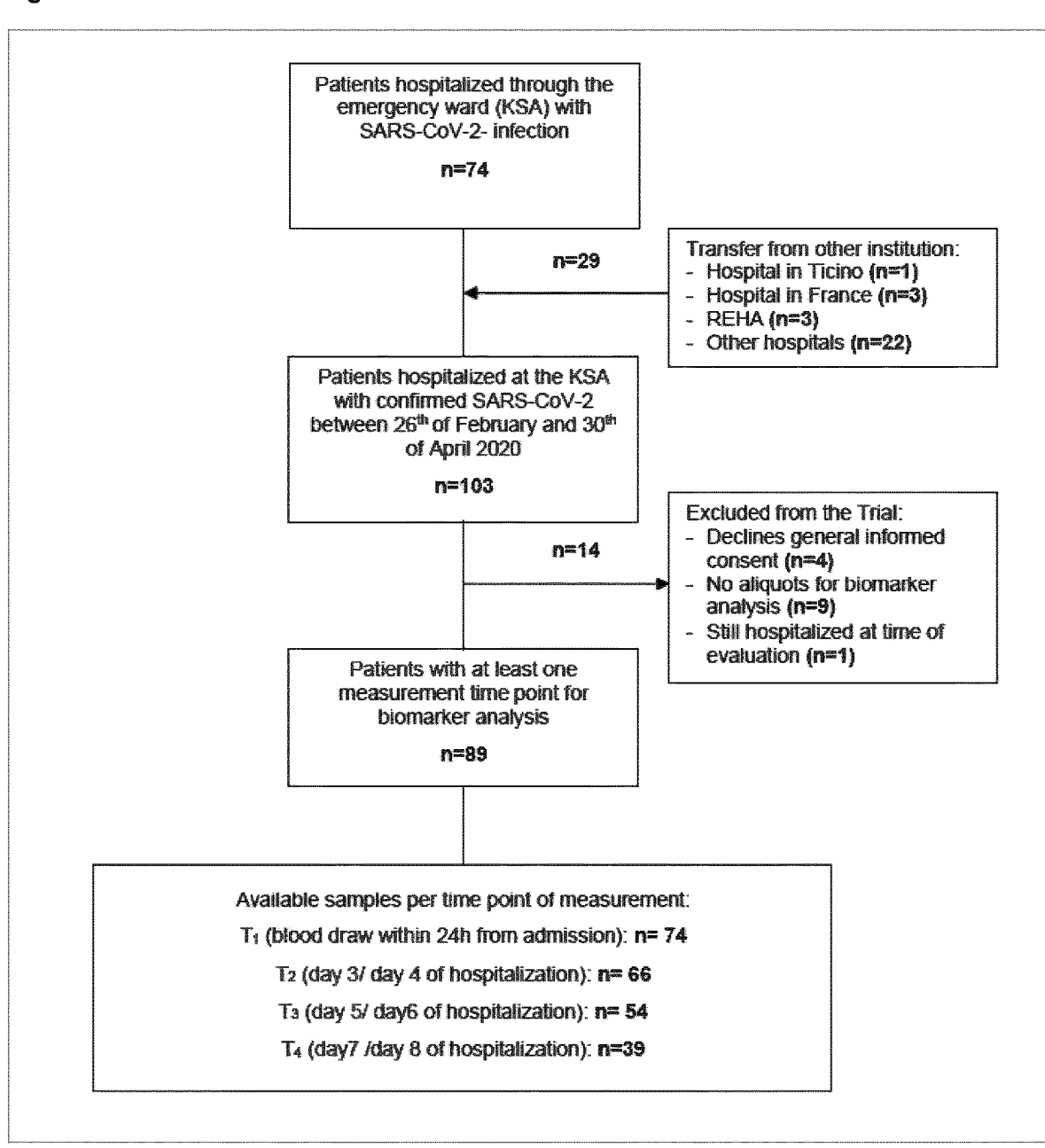

16 Claims, 4 Drawing Sheets
Specification includes a Sequence Listing.

(56) References Cited

PUBLICATIONS

Wang et al., "Coronavirus disease 2019 in elderly patients: Characteristics and prognostic factors based on 4-week follow-up," *Journal of Infection*, vol. 80, No. 6, pp. 639-645, 2020.

Written Opinion of the International Preliminary Examining Authority (PCT Rule 66) issued in PCT/EP2021/058885 on Jul. 14, 2022 (9 pages).

Zhou et al., "Clinical course and risk factors for mortality of adult inpatients with COVID-19 in Wuhan, China: a retrospective cohort study," *The Lancet*, vol. 395, pp. 1054-1062, 2020.

Zou et al., "Prognostic Factors for Severe Acute Respiratory Syndrome: A Clinical Analysis of 165 Cases," *Clinical Infectious Diseases*, vol. 38, pp. 483-489, 2004.

* cited by examiner

A

Number at risk
| | | | | |
|---|---|---|---|---|
| ProADM Cut-off (0-0.75nmol/l) | 21 | 21 | 20 | 20 |
| ProADM Cut-off (>0.75-1.5nmol/l) | 39 | 36 | 35 | 32 |
| ProADM Cut-off (>1.5nmol/l) | 14 | 11 | 11 | 8 |

B

Number at risk
| | | | | |
|---|---|---|---|---|
| ProADM Cut-off (<0.87nmol/l) | 34 | 34 | 33 | 33 |
| ProADM Cut-off (>0.87nmol/l) | 40 | 34 | 33 | 27 |

C

PRO-ADRENOMEDULLIN FOR PROGNOSING DISEASE PROGRESSION IN SEVERE ACUTE RESPIRATORY SYNDROME (SARS)

CROSS REFERENCE TO RELATED APPLICATIONS

This is the § 371 U.S. National Stage of International Application No. PCT/EP2021/058885, filed Apr. 6, 2021, which was published in English under PCT Article 21(2), which in turn claims the benefit of EP Application Serial No. 20168321.6, filed Apr. 6, 2020, EP Application Serial No. 20168591.4, filed Apr. 7, 2020, EP Application Serial No. 20179787.5, filed Jun. 12, 2020, and EP Application Serial No. 20191084.1, filed Aug. 14, 2020, all of which are incorporated herein by reference in their entirety.

The Sequence Listing is submitted as an ASCII text file in the form of the file named 10301-108772-01_ST25.txt, which was created on Oct. 4, 2022, and is 13,132 bytes, which is incorporated by reference herein.

The invention relates to the field of medical risk assessment, clinical diagnostics and prognostics, and therapy guidance, and corresponding methods and products.

The invention relates to a method for prognosing disease progression in a patient that has or is at risk of developing a severe acute respiratory syndrome (SARS), wherein the method comprises determining a level of pro-adrenomedullin (proADM) or fragment(s) thereof in a sample from the patient, wherein said level indicates the severity of SARS progression. The method is in some embodiments configured for use when a patient exhibits symptoms of a severe acute respiratory syndrome (SARS), when a patient exhibits symptoms of infection with a SARS-virus, or when the patient is infected with a SARS-virus, such as a SARS-coronavirus, such as SARS-CoV2.

The invention further relates to a method for therapy guidance, stratification and/or control for the patient, wherein the level of proADM or fragment(s) thereof indicates whether the patient is or is not at risk of disease progression to a condition that requires intensified treatment and/or disease monitoring, such as hospitalization and/or admission to an ICU.

The invention further relates to prognosing disease progression in a patient that has or is at risk of developing a severe acute respiratory syndrome (SARS), wherein the patient is infected with a SARS-coronavirus and shows mild or no symptoms of SARS or of infection with a SARS-virus. The invention further relates to a prognosing a subsequent adverse event in the health of a patient that has been diagnosed with SARS.

BACKGROUND OF THE INVENTION

Severe acute respiratory syndrome (SARS) is a virus mediated respiratory disease which was first observed in 2002. Based on scientific reports it is assumed that all human CoVs may be of zoonotic origin. Once a human becomes infected, the virus can quickly spread via droplet transmission and close contact between humans, eventually leading to epidemic scenarios or even to a pandemia (1-3). Typical symptoms can be fever, chills, dry cough, dyspnea and diarrhea (mayoclinic). The appearance and severity of symptoms can be different among infected patients. Some patients also appear to be asymptomatic (4). Hence, the clinical course can vary from harmless, self-healing scenarios with no presentation to a medical site, to severe cases where patients do not survive at Intensive Care Units (ICU).

From a pathophysiological point of view, SARS is a complex medical condition, where the virus starts replicating in the upper respiratory tract and can further spread to the lower respiratory tract or target more non-respiratory organs and cells. Clinical investigations show that also liver, kidney, heart, intestine, brain and lymphocytes can be affected (Jin 2020, Gu 2005).

It is proposed that the virus can directly promote cell damage, whereby a systemic inflammatory response followed by multiple organ injury is triggered. CoVs also cause a dysfunctional renin-angiotensin system, which increases the pulmonary vascular permeability being a key factor for the development pulmonary edema. Both, systemic inflammatory responses and a dysfunctional renin-angiotensin system contribute to a so-called cytokine storm that triggers the acute respiratory distress syndrome (ARDS). Multi-organ failure and/or the onset of ARDS represent a severe state of SARS patients with a high mortality risk within few weeks or days (3, 5).

The following risk factors are considered to foster a severe course of the syndrome: age, cardiovascular diseases, cancer, diabetes, immunosuppression, smoking and obesity (6). In this retrospective analyzing these and further clinical parameters and markers such as D-dimers and the SOFA score are analyzed for the prognosis of COVID-19. Lang Wang et al. ("Coronavirus disease 2019 in elderly patients: Characteristics and prognostic factors based an 4-week follow-up", Journal of Infection, vol. 80, no. 6, 1 Jan. 2020, pages 639-645) analyze older COVID-19 patients regarding certain clinical disease characteristics and prognostic factors. Zhengsheng Zou et al ("Prognostic Factors for Severe Acute Respiratory Syndrome: A Clinical Analysis of 165 Cases", Clin Infect Dis 2004 Feb. 15; 38(4): 483-489) also examine clinical/prognostic factors in SARS patients.

During epidemic scenarios, there is a clear need to maintain a functional healthcare system to ensure an appropriate care for low to high risk patients. Emergency Departments or Intensive Care Units can be quickly overcrowded with patients showing severe symptoms. For critically ill patients, a biomarker-based assessment can help to identify patients who may require an escalation of therapeutic interventions or who may not require an escalation of therapies and who may be eligible for an early ICU discharge.

A biomarker enabling risk assessment of SARS patients is pro-adrenomedullin (proADM), which has so far not been implicated in SARS. ProADM is a prohormone generated by multiple tissues in order to stabilise the microcirculation and to protect against endothelial permeability and consequent organ failure (7-14). No data was published so far regarding proADM for risk stratification of SARS patients, but the biomarker has shown considerable promise, for example in the fields of sepsis (15) and lower respiratory tract infections (16-18). Salvador Bello et al ("Prognostic power of proadrenomedullin in community-acquired pneumonia is independent of aetiology", European Respiratory Journal, vol. 39, no. 5, 10 Nov. 2011, pages 1144-1155) describe proADM as a prognostic factor in pneumonia that is independent of etiology. Philipp Schuetz et al (Clinical Chemistry and Laboratory Medicine, vol. 53, no. 4, 1 Jan. 2015, pages 521-539) show that proADM can be used to predict disease progression in COPD. Jaume Baldira et al ("Biomarkers and clinical scores to aid the identification of disease severity and intensive care requirement following activation of an in-hospital sepsis code", Annals of Intensive Care, vol. 10, no. 1, 1 Jan. 2020, pages 1-11) analyse various biomarkers and scores, and describes proADM as suitable for identifying infections in patients with suspected sepsis.

The endothelium and microcirculation is widely acknowledged to play a significant role in the pathophysiological host response to sepsis, with the regulation and distribution of blood flow within each organ of major importance (19, 20). Measures of the endothelium and microcirculation, such as via proADM, may therefore provide an alternative indication as to the severity of the general host response, compared to scores of individual organ dysfunction.

Considering the potentially fast rate of infection of SARS-viruses in the population at large, and the potential for large-scale hospital admissions in epidemic or pandemic scenarios, novel means are needed to assess the risk of disease progression in patients that have or are at risk of developing a severe acute respiratory syndrome (SARS), for example those caused by SARS-viruses. Until now, clinicians have insufficiently reliable means to assess whether patients require intensified treatment and/or disease monitoring or can be safely released from clinical care.

SUMMARY OF THE INVENTION

In light of the difficulties in the prior art, the technical problem underlying the present invention is the provision of means for prognosing disease progression in a patient that has or is at risk of developing a severe acute respiratory syndrome (SARS).

The technical problem underlying the present invention may be considered as the provision of means, based on a simple assay to be carried out by health care providers, for determining:

Whether hospitalization is necessary for a patient that has or is at risk of developing a severe acute respiratory syndrome (SARS), for example when a patient appears at a primary health care provider, such as a general medical practitioner, with symptoms of SARS or with symptoms of infection with a SARS-virus, or Whether treatment and supervision on an ICU is required for a patient that has or is at risk of developing a severe acute respiratory syndrome (SARS), for example when a patient appears in the ED or in hospital with symptoms of SARS or with symptoms of infection with a SARS-virus, or Whether treatment and supervision in hospital or on an ICU is required for a patient that has or is at risk of developing a severe acute respiratory syndrome (SARS) that has been diagnosed as suffering from infection with a SARS-virus, independent of whether symptoms of SARS are evident.

The present invention therefore relates to methods, kits and further means for diagnosis, prognosis, prediction, risk assessment and/or risk stratification, or therapy guidance, stratification and/or control of a patient with symptoms of SARS or of infection with a SARS-virus, or patients who have been diagnosed with SARS or an infection with a SARS-virus, on the basis of adrenomedullin (ADM) levels, in particular proADM or MR-proADM levels, determined in a sample from said patient.

One object of the invention is therefore the use of a biomarker, or combination of biomarkers or a biomarker in combination with a clinical score, to distinguish patients who are more likely or have a high risk of requiring hospitalization or treatment and/or supervision on an ICU (ie high risk of requiring intensive treatments provided in hospital or on an ICU) from patients who have a low risk of requiring such treatment.

The solution to the technical problem of the invention is provided in the independent claims.

Preferred embodiments of the invention are provided in the dependent claims.

Accordingly, proADM may be used as a tool to indicate the severity of SARS progression in patients with or at risk of SARS. Such patients may require a transfer to a clinical setting for intensified treatment and/or disease monitoring, such as an escalation of therapeutic interventions. Alternatively, the proposed approach enables patients to be identified for an early discharge from clinical care in conjunction with a de-escalation of specific therapies.

Therefore, in one aspect the invention relates to a method for prognosing disease progression in a patient that has or is at risk of developing a severe acute respiratory syndrome (SARS), wherein the method comprises determining a level of pro-adrenomedullin (proADM) or fragment(s) thereof in a sample from the patient, wherein said level indicates the severity of SARS progression.

In embodiments, the determined level proADM or fragment(s) thereof indicates a need of the patient for intensified treatment. Preferably, the determined level proADM or fragment(s) thereof indicates a need for oxygen support, invasive mechanical ventilation, or non-invasive mechanical ventilation. In embodiments, the need for intensified treatment, in particular oxygen support, invasive mechanical ventilation, or non-invasive mechanical ventilation, may be immediately after determining the level of proADM or fragment(s) thereof, or within 30 minutes, 1 hour, 2, 3, 4, 5, 6, 8, 12, 16, 20, or 24 hours or within 2, 3, 4, 5, 6, 7, 10, 14, 17, 21, 24, or 28 days. In embodiments, the need for intensified treatment, in particular oxygen support, invasive mechanical ventilation, or non-invasive mechanical ventilation, is during the hospital stay of the patient.

In embodiments, the determined level proADM or fragment(s) thereof indicates that the patient does not or will not need intensified treatment. Preferably, the determined level proADM or fragment(s) thereof indicates that the patient does not or will not need oxygen support, invasive mechanical ventilation, or non-invasive mechanical ventilation. In embodiments, the determined proADM or fragment(s) thereof indicates that the patient does not or will not need intensified treatment, in particular oxygen support, invasive mechanical ventilation, or non-invasive mechanical ventilation, immediately after determining the level of proADM or fragment(s) thereof, or within 30 minutes, 1 hour, 2, 3, 4, 5, 6, 8, 12, 16, 20, 24 hours or within 2, 3, 4, 5, 6, 7, 10, 14, 17, 21, 24, 28 days. In embodiments, the determined proADM or fragment(s) thereof indicates that the patient does not or will not need intensified treatment, in particular oxygen support, invasive mechanical ventilation, or non-invasive mechanical ventilation, during the hospital stay of the patient.

In embodiments, where the determined proADM or fragment(s) thereof indicates that the patient will not need intensified treatment, in particular oxygen support, invasive mechanical ventilation, or non-invasive mechanical ventilation, for example immediately after determining the level of proADM or fragment(s) thereof, or within 30 minutes, 1 hour, 2, 3, 4, 5, 6, 8, 12, 16, 20, 24 hours or within 2, 3, 4, 5, 6, 7, 10, 14, 17, 21, 24, or 28 days or during the hospital stay, the determined proADM or fragment(s) thereof indicates that the patient is not at risk of a disease progression to a condition that requires hospitalization.

In one embodiment, the method comprises additionally therapy guidance, stratification and/or control for the patient, wherein the level of proADM or fragment(s) thereof indicates whether the patient is at risk of disease progression to a condition that requires intensified treatment and/or disease monitoring.

In one embodiment, the patient exhibits symptoms of a severe acute respiratory syndrome (SARS).

In one embodiment, the patient exhibits symptoms of infection with a SARS-virus.

In one embodiment, the patient is infected with a SARS-virus.

In one embodiment, the patient is infected with a coronavirus.

In one embodiment, the patient is infected with a SARS-coronavirus.

In one embodiment, the SARS-coronavirus comprises SARS-CoV2.

In one embodiment, the patient is not infected with an influenza virus.

In one embodiment, the patient is additionally infected with an influenza virus.

In one embodiment, the patient exhibits symptoms of a severe acute respiratory syndrome (SARS) and is infected with an influenza virus. In one embodiment, the patient exhibits symptoms of infection with a SARS-virus and is infected with an influenza virus. In one embodiment, the patient is infected with a SARS-virus and is infected with an influenza virus. In one embodiment, the patient is infected with a coronavirus and is infected with an influenza virus. In one embodiment, the patient is infected with a SARS-coronavirus and is infected with an influenza virus.

In one embodiment, the patient is additionally at risk of developing an influenza virus infection.

In one embodiment, the patient exhibits symptoms of a severe acute respiratory syndrome (SARS) and is at risk of developing an influenza virus infection. In one embodiment, the patient exhibits symptoms of infection with a SARS-virus and is at risk of developing an influenza virus infection. In one embodiment, the patient is infected with a SARS-virus and is at risk of developing an influenza virus infection. In one embodiment, the patient is infected with a coronavirus and is at risk of developing an influenza virus infection. In one embodiment, the patient is infected with a SARS-coronavirus and is at risk of developing an influenza virus infection.

In one embodiment, the patient additionally exhibits symptoms of an influenza virus infection.

In one embodiment, the patient exhibits symptoms of a severe acute respiratory syndrome (SARS) and exhibits symptoms of an influenza virus infection. In one embodiment, the patient exhibits symptoms of infection with a SARS-virus and exhibits symptoms of an influenza virus infection. In one embodiment, the patient is infected with a SARS-virus and exhibits symptoms of an influenza virus infection. In one embodiment, the patient is infected with a coronavirus and exhibits symptoms of an influenza virus infection. In one embodiment, the patient is infected with a SARS-coronavirus and exhibits symptoms of an influenza virus infection.

In one embodiment, the patient additionally suffers from a bacterial infection.

In one embodiment, the patient exhibits symptoms of a severe acute respiratory syndrome (SARS) and suffers from a bacterial infection. In one embodiment, the patient exhibits symptoms of infection with a SARS-virus and suffers from a bacterial infection. In one embodiment, the patient is infected with a SARS-virus and suffers from a bacterial infection. In one embodiment, the patient is infected with a coronavirus and suffers from a bacterial infection. In one embodiment, the patient is infected with a SARS-coronavirus and suffers from a bacterial infection.

In one embodiment, the patient is additionally at risk of developing a bacterial infection.

In one embodiment, the patient exhibits symptoms of a severe acute respiratory syndrome (SARS) and is at risk of developing a bacterial infection. In one embodiment, the patient exhibits symptoms of infection with a SARS-virus and is at risk of developing a bacterial infection. In one embodiment, the patient is infected with a SARS-virus and is at risk of developing a bacterial infection. In one embodiment, the patient is infected with a coronavirus and is at risk of developing a bacterial infection. In one embodiment, the patient is infected with a SARS-coronavirus and is at risk of developing a bacterial infection.

In one embodiment, the patient additionally exhibits symptoms of a bacterial infection.

In one embodiment, the patient exhibits symptoms of a severe acute respiratory syndrome (SARS) and exhibits symptoms of a bacterial infection. In one embodiment, the patient exhibits symptoms of infection with a SARS-virus and exhibits symptoms of a bacterial infection. In one embodiment, the patient is infected with a SARS-virus and exhibits symptoms of a bacterial infection. In one embodiment, the patient is infected with a coronavirus and exhibits symptoms of a bacterial infection. In one embodiment, the patient is infected with a SARS-coronavirus and exhibits symptoms of a bacterial infection.

In one embodiment, the patient additional suffers from an influenza virus infection and a bacterial infection.

In one embodiment, the patient exhibits symptoms of a severe acute respiratory syndrome (SARS) and suffers from an influenza virus infection and a bacterial infection. In one embodiment, the patient exhibits symptoms of infection with a SARS-virus and suffers from an influenza virus infection and a bacterial infection. In one embodiment, the patient is infected with a SARS-virus and suffers from an influenza virus infection and a bacterial infection. In one embodiment, the patient is infected with a coronavirus and suffers from an influenza virus infection and a bacterial infection. In one embodiment, the patient is infected with a SARS-coronavirus and suffers from an influenza virus infection and a bacterial infection.

In one embodiment, the patient is additionally at risk of developing an influenza virus infection and a bacterial infection.

In one embodiment, the patient exhibits symptoms of a severe acute respiratory syndrome (SARS) and is at risk of developing an influenza virus infection and a bacterial infection. In one embodiment, the patient exhibits symptoms of infection with a SARS-virus and is at risk of developing an influenza virus infection and a bacterial infection. In one embodiment, the patient is infected with a SARS-virus and is at risk of developing an influenza virus infection and a bacterial infection. In one embodiment, the patient is infected with a coronavirus and is at risk of developing an influenza virus infection and a bacterial infection. In one embodiment, the patient is infected with a SARS-coronavirus and is at risk of developing an influenza virus infection and a bacterial infection.

In one embodiment, the patient additionally exhibits symptoms of an influenza virus infection and a bacterial infection.

In one embodiment, the patient exhibits symptoms of a severe acute respiratory syndrome (SARS) and exhibits symptoms of an influenza virus infection and a bacterial infection. In one embodiment, the patient exhibits symptoms of infection with a SARS-virus and exhibits symptoms of an influenza virus infection and a bacterial infection. In one embodiment, the patient is infected with a SARS-virus and exhibits symptoms of an influenza virus infection and a bacterial infection. In one embodiment, the patient is infected with a coronavirus and exhibits symptoms of an influenza virus infection and a bacterial infection. In one embodiment, the patient is infected with a SARS-coronavirus and exhibits symptoms of an influenza virus infection and a bacterial infection.

In one embodiment, the patient belongs to a patient group with an increased risk of an adverse event in case of developing a severe acute respiratory syndrome (SARS).

In one embodiment, the patient group with an increased risk of an adverse event is selected from the group consisting of patients with an age of 60 years or more, preferably 70 years or more; patients with long-term respiratory or lung disease, such as asthma, cystic fibrosis or chronic obstructive pulmonary disease (COPD); patients with long-term heart disease, such as heart failure, patients with long-term kidney disease; patients with long-term liver disease, such as hepatitis; patients with diabetes; patients with long-term neurological conditions, such as Parkinson's disease, motor neuron disease, multiple sclerosis (MS), cerebral palsy, or a learning disability; patients with splenic disease, such as sickle cell anemia or splenectomy; patients with a weakened immune system, such as patients with HIV or AIDS, or patients receiving immunosuppressive medication; patients with a body mass index (BMI) of 30 or above, a BMI of 35 or above, and a BMI of 40 or above (severely obese patients); pregnant women; patients that had an organ transplantation taking immunosuppressive medication and cancer patients, in particular cancer patients receiving chemotherapy or radiotherapy.

In one embodiment, determining a level of proADM or fragment(s) thereof comprises determining a level of MR-proADM in the sample.

In one embodiment, the sample is selected from the group consisting of a blood sample, such as a whole blood sample, a serum sample or a plasma sample, and/or a urine sample.

In one embodiment, the level of proADM or fragment(s) thereof is determined in a sample obtained by the first medical personnel to consult with the patient after occurrence of the symptoms of SARS or of infection with a SARS-virus.

In one embodiment, the patient is infected with a SARS-coronavirus and shows mild or no symptoms of SARS or of infection with a SARS-virus.

For example, the method may be employed in combination with testing for the presence of a SARS-virus, such as a coronavirus, independent of whether symptoms are evident.

In one embodiment, the method comprises:

providing a sample from said patient, and determining a level of proADM or fragment(s) thereof in said sample, wherein a low risk level of proADM level or fragment(s) thereof in said sample indicates that the patient is not at risk of disease progression to a condition that requires intensified treatment and/or disease monitoring, and/or wherein a high risk level of proADM level or fragment(s) thereof in said sample indicates that the patient is at risk of disease progression to a condition that requires intensified treatment and/or disease monitoring.

In one embodiment, a low risk level of proADM level or fragment(s) thereof in said sample indicates that the patient is not at risk of a disease progression to a condition that requires hospitalization, and/or wherein a high risk level of proADM level or fragment(s) thereof in said sample indicates that the patient is at risk of a disease progression to a condition that requires hospitalization.

In one embodiment, a low risk level of proADM level or fragment(s) thereof in said sample indicates that the patient is not at risk of a disease progression to a condition that requires treatment and/or disease monitoring on an ICU, and/or wherein a high risk level of proADM level or fragment(s) thereof in said sample indicates that the patient is at risk of a disease progression to a condition that requires treatment and/or disease monitoring on an ICU.

In one embodiment, a low risk level of proADM level or fragment(s) thereof in said sample indicates that the patient is not at risk of a disease progression to a condition that requires oxygen support, invasive mechanical ventilation, or non-invasive mechanical ventilation, and/or wherein a high risk level of proADM level or fragment(s) thereof in said sample indicates that the patient is at risk of a disease progression to a condition that requires oxygen support, invasive mechanical ventilation, or non-invasive mechanical ventilation.

In embodiments, a low risk level of proADM level or fragment(s) thereof in said sample indicates that the patient is not at risk of a disease progression to a condition that requires oxygen support, invasive mechanical ventilation, or non-invasive mechanical ventilation immediately after determining the level of proADM or fragment(s) thereof, or within 30 minutes, 1 hour, 2, 3, 4, 5, 6, 8, 12, 16, 20, 24 hours or within 2, 3, 4, 5, 6, 7, 10, 14, 17, 21, 24, or 28 days, or during the hospital stay; and/or wherein a high risk level of proADM level or fragment(s) thereof in said sample indicates that the patient is at risk of a disease progression to a condition that requires oxygen support, invasive mechanical ventilation, or non-invasive mechanical ventilation immediately after determining the level of proADM or fragment(s) thereof, or within 30 minutes, 1 hour, 2, 3, 4, 5, 6, 8, 12, 16, 20, 24 hours or within 2, 3, 4, 5, 6, 7, 10, 14, 17, 21, 24, or 28 days or during the hospital stay In one embodiment, the low risk level is equal or below 0.87 nmol/l±20%, and/or wherein said high risk level is above 0.87 nmol/l±20%.

It represents a surprising finding that a cut-off value of proADM of or above 0.87 nmol/l±20% (preferably using an immunoassay for MR-proADM) enables a reliable indication that a patient is likely to experience worsening of their condition (such as a SARS-coronavirus infection), such that intensifying treatment and/or disease monitoring and/or hospitalization is necessary.

As such, the prognostic statements described herein appear to represent a surprising and beneficial finding in the field of SARS prognosis and patient management in a primary care and/or hospital setting.

In one embodiment, the low risk level is equal or below 0.93 nmol/l±20%, and/or wherein said high risk level is above 0.93 nmol/l±20%.

It represents a surprising finding that a cut-off value of proADM of or above 0.93 nmol/l±20% (preferably using an immunoassay for MR-proADM) enables a reliable indication that a patient is likely to experience worsening of their condition (such as a SARS-coronavirus infection), such that intensifying treatment and/or disease monitoring and/or hospitalization is necessary. In some embodiments, a cut-off value of proADM of or above 0.93 nmol/l±20% enables assessment of disease severity, disease progression, risk for in-hospital mortality and also for decisions regarding patient disposition, as patients with values above this cut-off showed increased risk of one or more of disease progression to a serious state, indicating a risk for in-hospital mortality.

In a further embodiment, the low risk level is equal or below 0.75 nmol/l±20%, and/or wherein said high risk level is above 0.75 nmol/l±20%.

In a further embodiment, the low risk level is equal or below 1.5 nmol/l±20%, and/or wherein said high risk level is above 1.5 nmol/l±20%.

In a further embodiment, the low risk level is equal or below 0.75 nmol/l±20%, and/or wherein said high risk level is above 2.5 nmol/l±20%.

In a further embodiment, the low risk level is equal or below 0.75 nmol/l±20%, and/or wherein said high risk level is above 2.5 nmol/l±20%.

Further cut-off values of the present invention, which can be associated with specific time points of sample isolation after occurrence of symptoms, presentation of the patient to medical personnel and/or hospitalization, are disclosed in the examples.

The term "indicates that the patient is, or is not, at risk of disease progression to a condition that requires hospitalization" relates in some embodiments to the prognosis of a worsening of patient condition. In some embodiments, this term relates to a prognosis of whether certain treatments, which are only or primarily available in hospital, are necessary. In some embodiments, this term relates to prognosis of disease outcome.

Although proADM is known to predict disease outcome for some medical conditions, the present invention presents particular cut-off values applicable to a patient that has or is at risk of developing a severe acute respiratory syndrome (SARS) in primary care scenarios in particular patient groups, which would not have been derived from the prior art or suggested previously in the context of predicting potential hospitalization.

In some embodiments, treatments commonly received in hospital relate to treatments excluding topical and/or oral antibiotic administration.

Examples of treatments commonly received in hospital relate further to intravenous administration of antiviral therapies, administration experimental therapies, off-label use of medication and treatments approved for other indications, administration of antibiotics, or other fluid therapy, such as fluid management, fluid resuscitation, fluid replacement and/or fluid redistribution, such as of colloids and/or crystalloids, or blood transfusions.

Other treatments primarily available in hospital are, but are not limited to, renal replacement therapy (RRT), artificial and mechanical ventilation, surgery or cleaning procedures, such as focus cleaning.

The term "hospitalization" refers preferably, in some embodiments, to hospital admission. This differs from being referred to hospital, being assessed, and subsequently released (sent home). Hospital admission refers preferably to maintained control and/or assessment of the medical condition of a patient in the hospital, whether it be in an emergency room, ward, intensive care station, or other area of a hospital or clinic. Admission preferably, in some embodiments, relate to overnight admission of the patient for monitoring.

In embodiments, the method of the invention includes a step of hospitalizing the patient in case a high risk level of proADM has been determined. In embodiments of the invention, hospitalizing the patient refers to admission of the patient to a hospital or clinic or similar medical institution for a maintained control and/or assessment of the medical condition or the health status and/or monitoring of changes of the health state of the patient and/or medical treatment, preferably for several hours, such as more than 5, 6, 7, 8, 9, 10, 11, 12, 15, 18 or 24 hours or longer.

The method of the invention represents a significant and surprising advancement in comparison to known methods of the state of the art. Although determining the level of proADM as a biomarker in sepsis patients has been described, there has been no prior disclosure regarding the use of proADM as a marker in a method for therapy guidance, stratification and/or control in a patient that has or is at risk of developing a severe acute respiratory syndrome (SARS), such as a coronavirus infection or preferably COVID-19 (infection with SARS-CoV2), for deciding whether such a patient requires intensifying treatment and/or disease monitoring and/or hospitalization or not.

In particular, the method of the invention defines a high risk level of proADM or fragment(s) thereof, which is decisive for indicating whether the patient should be hospitalized or not, and which has not been previously disclosed in the context of this decision making process. The present invention is particularly useful for patients with symptoms of SARS or of an infection with a SARS-virus and/or that may not exhibit symptoms of viral pneumonia, pneumonia, sepsis, acute respiratory distress syndrome (ARDS) and/or respiratory failure. The method of the invention is also particularly useful for patients that do not suffer from hematological disorders or other disorders that may affect the immune system and/or the defense of the patients against infections, wherein these patients may for example only display mild symptoms of SARS or of infection with a SARS-virus.

In embodiments, the patient has already been diagnosed with SARS, such as COVID-19.

In embodiments, the patient shows no symptoms of SARS or of an infection with a SARS-virus. In embodiments, the patient is at risk of developing SARS and shows no symptoms of SARS or of an infection with a SARS-virus.

In one embodiment, the level of proADM or fragment(s) thereof is determined in a sample obtained by the first medical personnel to consult with the patient after occurrence of the symptoms of SARS or of infection with a SARS-virus.

In embodiments of the invention the term "first medical personnel to consult with the patient after occurrence of the symptoms of SARS or of infection with a SARS-virus" relates to, but is not limited to, general practitioners (GP), home health care workers or care givers, nurses in residences for retirees, ambulance drivers, or workers, paramedics, doctors making home visits, nurses in community clinics, and the like. The first medical personnel is preferably construed to encompass and medical staff, whether a doctor or other care giver, who first encounters a patient who has developed symptoms of infectious disease, but who has preferably not been diagnosed with a sever illness. In some embodiments, the first medical personnel to encounter a subject is in a hospital, in the admissions area, in the emergency room or emergency department (ED), who are receiving subjects presenting with symptoms of SARS or of infection with a SARS-virus.

It is entirely surprising that based on a single proADM measurement an accurate and reliable conclusion can be made as to whether the patient will go on to develop a SARS of such severity that hospitalization is required, such as viral pneumonia. This prognostic ability of proADM is, to the knowledge of the inventors, novel and surprising.

In one embodiment, the patient is presented in a primary care unit and a high risk level of proADM or fragment(s)

thereof indicates that hospitalization of the patient is required, and wherein a low risk level of proADM or fragment(s) indicates that hospitalization of the patient is not required.

In preferred embodiments of the present invention the method is defined by the prognosis of potential hospitalization in a patient group, for whom it was previously difficult, if not impossible, to determine by routine clinical and/or molecular diagnostic means, whether a serious risk existed of serious deterioration of medical conditions, thereby requiring hospitalization. This patient group may be considered patients with mild symptoms of SARS or of infection with a SARS-virus, or patients at risk of developing a SARS.

In one embodiment, at the time of sample provision the patient shows mild symptoms of SARS or infection with a SARS-virus corresponding to a qSOFA score of 0 or 1.

In one embodiment, at the time of sample provision, the patient shows mild symptoms of SARS or infection with a SARS-virus corresponding to a PSI score of ≤90.

In one embodiment, at the time of sample provision the patient shows no clinical symptoms for a blood stream infection, a sepsis, a severe sepsis and/or septic shock in the patient.

In one embodiment, at the time of sample provision the patient shows no clinical symptoms for a bacterial infection of the respiratory tract, pneumonia, respiratory failure, multi-organ failure and/or acute respiratory distress syndrome (ARDS).

It was entirely surprising that patients that only show mild symptoms of SARS or infection with a SARS-virus, such as patients corresponding to a qSOFA score of 0 or 1, and patients that show symptoms of SARS or infection with a SARS-virus that however do not indicate the presence of a blood stream infection, sepsis, bacterial infection of the respiratory tract, pneumonia, respiratory failure, multi-organ failure and/or acute respiratory distress syndrome (ARDS), can be categorized as requiring hospitalization on the basis of determining a high risk level of proADM or fragment(s) according to the present invention.

It was entirely surprising that patients that only show mild symptoms of SARS or infection with a SARS-virus, such as patients corresponding to a PSI score of ≤90, and patients that show symptoms of SARS or infection with a SARS-virus that however do not indicate the presence of a blood stream infection, sepsis, bacterial infection of the respiratory tract, pneumonia, respiratory failure, multi-organ failure and/or acute respiratory distress syndrome (ARDS), can be categorized as requiring hospitalization on the basis of determining a high risk level of proADM or fragment(s) according to the present invention.

This represents a great advantage of the method of the invention, since a specialized physician would not expect that patients with mild symptoms of SARS or of infection with a SARS-virus and/or symptoms that do not hint towards blood stream infection, sepsis, additional bacterial infection of the respiratory tract, pneumonia, respiratory failure, multi-organ failure and/or acute respiratory distress syndrome (ARDS), would require hospitalization, for example to monitor progression of the symptoms of the SARS or of infection with a SARS-virus and perform treatment. Such patients may usually be examined by medical personnel and subsequently released from continuous medical observation, for example with treatment instructions that can be carried out without professional medical supervision. However, the method of the present invention can identify patients, by objective means, who do not exhibit severe symptoms of a SARS or of infection with a SARS-virus and that still do require hospitalization.

On the other hand, for reasons of caution there is a tendency of medical personnel, in particular personnel that is not specialized in the field of SARS or of infection with a SARS-virus, to send patients with symptoms of a SARS or of infection with a SARS-virus and even with mild symptoms that do not indicate blood stream infection, sepsis, additional bacterial infection of the respiratory tract, pneumonia, respiratory failure, multi-organ failure and/or ARDS to the hospital or emergency department, although this may not be required. The method of the invention represents a great advantage since it can provide objective criteria even to unexperienced medical personnel that may not be specialized in SARS or of infection with a SARS-virus to decide whether a patient has to be hospitalized or not. So the rate of unnecessary hospital admissions that are due to overly cautious decision making of the medical personnel observing the patient could be lowered by the aid of the method of the invention. On the other hand, the rate of patients with mild symptoms that are not admitted to the hospital although they would require constant medical observation may be increased.

A preferred cut-off value of 0.87 nmol/L±20% is completely unexpected and surprising and has not been reported in the state of the art for the patient group described herein and for the decision making process of hospitalizing a patient or not. This cut-off is particularly beneficial for deciding to hospitalize patients with mild symptom and patients that are not suspected of progressing to a severe disease state, such as a state requiring mechanical ventilation, since these patients may in many cases be wrongly released from constant medical supervision due to the lack of suitable diagnostic and prognostic tests that support the decision making process.

In one embodiment, the level of proADM or fragment(s) thereof in said sample in between 0.5 nm/L±20% and 0.87 nmol/L±20% indicates the presence of the disease and that the patient is not at risk of a disease progression to a condition that requires a hospitalization.

The range of proADM values from 0.5 nm/L±20% and 0.87 nmol/L±20% is of particular benefit, as healthy patients often have proADM levels from 0.0 to 0.5 nmol/L. In some embodiments, patients with over 1.5 nmol/L also require serious treatment. Therefore, there previously existed a "gray zone" of uncertainty for medical professionals, when ADM values from 0.5 nm/L±20% to 0.87 nmol/L±20% were measured. The present invention however now enables reliable prognostic statement for such patients. In some embodiments, these patients are ruled out from hospitalization, as they do not exhibit a significant risk of progressing to a serious condition requiring hospitalization.

A preferred cut-off value of 0.93 nmol/L±20% is completely unexpected and surprising and has not been reported in the state of the art for the patient group described herein and for the decision making process of hospitalizing a patient or not. This cut-off is particularly beneficial for deciding to hospitalize patients with mild symptom and patients that are not suspected of progressing to a severe disease state, such as a state requiring mechanical ventilation, since these patients may in many cases be wrongly released from constant medical supervision due to the lack of suitable diagnostic and prognostic tests that support the decision making process.

In one embodiment, the level of proADM or fragment(s) thereof in said sample in between 0.5 nm/L±20% and 0.93 nmol/L±20% indicates the presence of the disease and that the patient is not at risk of a disease progression to a condition that requires a hospitalization.

The range of proADM values from 0.5 nm/L±20% and 0.93 nmol/L±20% is of particular benefit, as healthy patients often have proADM levels from 0.0 to 0.5 nmol/L. In some embodiments, patients with over 1.5 nmol/L also require serious treatment. Therefore, there previously existed a "gray zone" of uncertainty for medical professionals, when ADM values from 0.5 nm/L±20% to 0.93 nmol/L±20% were measured. The present invention however now enables reliable prognostic statement for such patients. In some embodiments, these patients are ruled out from hospitalization, as they do not exhibit a significant risk of progressing to a serious condition requiring hospitalization.

In one embodiment, a high risk level of proADM or fragments thereof indicates that the patient is at risk of disease progression to a life-threatening condition within 28 days, 72 hours, 48 hours, 24 hours, preferably 12 hours and wherein a low risk level of proADM indicates that the patient is not at risk of disease progression to a life-threating condition within 28 days 72 hours, 48 hours, 24 hours, preferably 12 hours.

In one embodiment, a high risk level of proADM or fragments thereof indicates that the patient is at risk of disease progression to a life-threatening condition within 21 days, 14 days, 7 days, 5 days, or 4 days, and a low risk level of proADM indicates that the patient is not at risk of disease progression to a life-threating condition within 21 days, 14 days, 7 days, 5 days, or 4 days.

In a preferred embodiment, a high risk level of proADM or fragments thereof indicates that the patient is at risk of disease progression to a life-threatening condition within 7 days, and a low risk level of proADM indicates that the patient is not at risk of disease progression to a life-threating condition within 7 days.

In embodiments, a high risk level of proADM or fragment (s) thereof in said sample, preferably a high risk level of over 1.5 nmol/L, indicates that the patient is at risk of a disease progression to a condition that requires hospitalization and/or treatment and/or disease monitoring on an ICU and/or of an adverse event. In embodiments, a high risk level of proADM or fragment(s) thereof in said sample, preferably a high risk level of over 1.5 nmol/L, indicates the occurrence of an adverse event, such as death, in particular death within 1, 2, 3, 4, 5, 6, 7, 8, 9, 10, 12, 14, 16, 18, 21, 24, or 28 days, preferably 7 or 28 days. In embodiments, a low risk level of proADM or fragment(s) thereof in said sample, preferably a low risk level of 1.5 nmol/L or below, indicates the absence of an adverse event, such as death, in particular death within 1, 2, 3, 4, 5, 6, 7, 8, 9, 10, 12, 14, 16, 18, 21, 24, or 28 days, preferably 7 or 28 days.

In one embodiment, the level of proADM or fragment(s) thereof in said sample is indicative of the risk of a development of a systemic inflammatory response (SIRS), coagulation disorders, blood stream infection, sepsis, severe sepsis and/or septic shock in the patient that requires hospitalization.

In one embodiment, the level of proADM or fragment(s) thereof in said sample is indicative of the risk of a development of a bacterial infection of the respiratory tract, pneumonia, respiratory failure, multi-organ failure and/or ARDS.

In one embodiment, a high risk level of proADM thereof indicates that the patient is at risk to develop a systemic inflammatory response (SIRS), coagulation disorders, blood stream infection, sepsis, severe sepsis and/or septic shock that requires hospitalization within 72 hours, 48 hours, 24 hours, preferably 12 hours and wherein a low risk level of proADM indicates that the patient is not at risk to develop blood stream infection, a sepsis, a severe sepsis and/or a septic shock within 48 hours, 24 hours, preferably 12 hours.

In one embodiment, a high risk level of proADM thereof indicates that the patient is at risk to develop a pathogenesis of a viral infection of the respiratory tract comprising pneumonia, respiratory failure, multi-organ failure and/or ARDS that requires hospitalization within 72 hours, 48 hours, 24 hours, 12 hours or immediate and wherein a low risk level of proADM indicates that the patient is not at risk to develop a bacterial infection of the respiratory tract, pneumonia, respiratory failure, multi-organ failure and/or ARDS within 72 hours, 48 hours, 24 hours, preferably 12 hours or immediate.

In one embodiment, the level of proADM or fragment(s) thereof in said sample is indicative of the patient requiring frequent monitoring and/or critical care treatment. In one embodiment, the patient with a high risk level will require a medical treatment provided in a hospital setting. Examples of these treatments include but are not limited to fluid therapy, intravenous antibiotics, mechanical ventilation, experimental therapy, off-label administration of pharmaceutical compositions, antiviral therapy, in some embodiments essentially any treatment beyond oral antibiotics, which may be self-administered at home.

In one embodiment, the method additionally comprises:
determining at least one clinical score, such as NEWS, SOFA, qSOFA, CRB-65, PSI and/or APACHE II score, for the patient suspected of having an infectious disease,
wherein the at least one clinical score and the level of proADM or fragment(s) thereof is indicative of the presence of the SARS or of infection with a SARS-virus, such as virus-induced pneumonia, and whether the patient is at risk of a disease progression to a condition that requires a hospitalization.

In one embodiment, determining a level of proADM or fragment(s) thereof comprises determining a level of MR-proADM in the sample. As demonstrated in the examples below, MR-proADM, preferably determined using established immunoassay products of B.R.A.H.M.S (Hennigsdorf, Germany), shows a reliable and effective prognosis according to the methods described herein. Alternative ADM molecules, including precursors or fragments, may also be employed.

In one embodiment, the sample is selected from the group consisting of a blood sample, such as a whole blood sample, a serum sample or a plasma sample, and/or a urine sample.

In one embodiment, the sample is isolated from the patients within 24 hours, 6 hours, 2 hours, 1 hour, more preferably within 30 minutes or 15 minutes after the symptoms have been determined.

In embodiments, the sample is isolated from the patient within 24 h (1 day), 2 days, 3, days, 4 days, 5 days, 6 days, 7 days, 8 days 9 days or 10 days after the symptoms have been determined and/or the time point of presentation to medical personnel and/or the time point of hospitalization.

Surprisingly, the preferred cut-off levels of 0.75, 0.87, 1.5, 2.25 and 2.5 nmol/l can be used at different time points after occurrence of symptoms and/or presentation to medical personnel and/or hospitalization for the prognosis of disease progression. These preferred cut-of levels are associated with advantageous sensitivity and specificity, depending on the specific application of the method of the invention.

In one embodiment, the method additionally comprises determining a level of at least one additional biomarker or fragment(s) thereof in a sample from said patient. Preferably, the level of the at least one additional biomarker is indicative of an initiation of treatment with an anti-infective agent, preferably an anti-viral agent and/or an antibiotic or antimitotic agent.

In one embodiment, the method additionally comprises:
- a. determining a level of at least one additional biomarker or fragment(s) thereof in a sample from said patient, wherein the at least one additional biomarker preferably is PCT or fragment(s) thereof, and
- b. wherein the level of the at least one additional biomarker is indicative of an initiation of treatment with an anti-infective agent, preferably an anti-viral agent and/or an antibiotic or antimitotic agent.

In one embodiment, at least one additional biomarker is PCT or fragment(s) thereof and a level of PCT or fragment(s) thereof above 0.25 ng/ml, preferably above 0.5 ng/ml is indicative of an bacterial infection or sepsis and indicates an initiation of a treatment with an anti-infective agent, preferably an antibiotic or antimitotic agent.

In one embodiment, at least one additional biomarker is PCT or fragment(s) thereof and a level of PCT or fragment(s) thereof below 0.25 ng/ml is indicative of a bacterial infection or sepsis and indicates an initiation of a treatment with an anti-infective agent, preferably an antibiotic or antimitotic agent, is not needed.

In one embodiment, at least one additional biomarker is PCT or fragment(s) thereof and a level of PCT or fragment(s) thereof below 0.1 ng/ml is indicative of the absence of a bacterial infection.

As demonstrated in more detail below, the combined measurement of additional biomarkers, in particular PCT, or other or additional acute care biomarkers such as D-Dimer, Troponin or Copeptin enables improved prognosis and/or further SARS related indications on the extent, severity or type of infection, myocardial infarction or coagulation disorders present in the subject. The combined measurement of PCT and proADM may, in some embodiments, lead to the decision regarding hospitalization in addition to the antibiotic dose and means of administration to the patient. The combination of these biomarkers therefore provides a beneficial and—in the particular patient group and practitioner group of the present invention—surprising effect.

In embodiments, the at least one additional biomarker additional biomarker is arginine vasopressin (AVP), pro-arginine vasopressin (proAVP) and/or Copeptin (CT-proAVP).

In embodiments, the additional biomarker includes Endothelin-1 (ET-1), such as CT-proET-1.

Surprisingly, it could be shown that the combined measurement of ET-1 (including CT-proET-1) and/or AVP (including proAVP and/or CT-proAVP) as additional biomarkers with proADM enables improved prognosis of disease progression. This improved prognosis can include an indication or prediction of the occurrence of an adverse event, such as death, preferably within a certain time frame after diagnosis and treatment initiation, such as within 1, 2, 3, 4, 5, 6, 7, 8, 9, 10, 12, 14, 16, 18, 21, 24, or 28 days.

The invention further relates to a method for therapy guidance, stratification and/or control in a patient with symptoms of a SARS or of infection with a SARS-virus, comprising a prognosis of disease progression, the method comprising:
providing a sample from said patient,
determining a level of proADM or fragment(s) thereof in said sample, and comparing the level of proADM or fragment(s) thereof in said sample to a cut-off value,
wherein said cut-off value is 0.87 nmol/l±20%,
wherein a (low risk) level of proADM or fragment(s) thereof in said sample below said cut-off value indicates that the patient is not at risk of a disease progression to a condition that requires hospitalization, and wherein a high risk level of proADM or fragment(s) thereof in said sample above said cut-off value indicates that the patient is at risk of a disease progression to a condition that requires hospitalization.

The method therefore relates to a method of treating a SARS or of infection with a SARS-virus in a patient, including electing the patient for treatment employing a method for therapy guidance, stratification and/or control in a patient with symptoms of a SARS or of infection with a SARS-virus, comprising a prognosis of disease progression, the method comprising:
providing a sample from said patient,
determining a level of proADM or fragment(s) thereof in said sample, and
comparing the level of proADM or fragment(s) thereof in said sample to a cut-off value,
wherein said cut-off value is 0.87 nmol/l±20%,
wherein a (low risk) level of proADM or fragment(s) thereof in said sample below said cut-off value indicates that the patient is not at risk of a disease progression to a condition that requires hospitalization, and wherein a high risk level of proADM or fragment(s) thereof in said sample above said cut-off value indicates that the patient is at risk of a disease progression to a condition that requires hospitalization.

The method of treatment preferably includes the administration of suitable therapeutic measures to said patient using preferably one or more of the particular therapies described herein.

In one embodiment, the invention relates to or comprises a method for treating a patient with symptoms of a SARS or of infection with a SARS-virus, the method comprising the steps of:
determining whether the patient has a high or low risk level of proADM, by:
obtaining or having obtained a biological sample from the patient;
performing or having performed an assay that determines a level of proADM or fragment(s) thereof in said sample;
wherein a low risk level of proADM level or fragment(s) thereof in said sample is equal or below 0.87 nmol/l±20%, and/or
wherein a high risk level of proADM level or fragment(s) thereof in said sample is above 0.87 nmol/l±20%,
wherein when a high risk level of proADM level or fragment(s) thereof in said sample is determined, the patient is treated, said treatment preferably including hospitalization, or a medical treatment available only or primarily at a hospital.

The invention further relates to a method for therapy guidance, stratification and/or control in a patient with symptoms of a SARS or of infection with a SARS-virus, comprising a prognosis of disease progression, the method comprising:
providing a sample from said patient,
determining a level of proADM or fragment(s) thereof in said sample, and
comparing the level of proADM or fragment(s) thereof in said sample to a cut-off value, wherein said cut-off value is 0.93 nmol/l±20%, wherein a (low risk) level of proADM or fragment(s) thereof in said sample below said cut-off value indicates that the patient is not at risk of a disease progression to a condition that requires hospitalization, and wherein a high risk level of proADM or fragment(s) thereof in said sample above said cut-off value indicates that the patient is at risk of a disease progression to a condition that requires hospitalization.

The method therefore relates to a method of treating a SARS or of infection with a SARS-virus in a patient, including electing the patient for treatment employing a method for therapy guidance, stratification and/or control in a patient with symptoms of a SARS or of infection with a SARS-virus, comprising a prognosis of disease progression, the method comprising:

providing a sample from said patient, determining a level of proADM or fragment(s) thereof in said sample, and comparing the level of proADM or fragment(s) thereof in said sample to a cut-off value, wherein said cut-off value is 0.93 nmol/l±20%, wherein a (low risk) level of proADM or fragment(s) thereof in said sample below said cut-off value indicates that the patient is not at risk of a disease progression to a condition that requires hospitalization, and wherein a high risk level of proADM or fragment(s) thereof in said sample above said cut-off value indicates that the patient is at risk of a disease progression to a condition that requires hospitalization.

wherein preferably when a high risk level of proADM level or fragment(s) thereof in said sample is determined, the patient is treated, said treatment preferably including hospitalization, or a medical treatment available only or primarily at a hospital.

In embodiments of the method for therapy guidance, stratification and/or control in a patient with symptoms of a SARS or of infection with a SARS-virus of the invention, in addition or alternatively to the cut-off value of 0.87 nmol/l, other cut-off values, such as 0.93 nmol/l, can be used. As shown in the examples, cut-off values of 0.75, 1.5, 2.25 and 2.5 nmol/l are useful and therefore represent suitable cut-off values to be used in the context of this aspect of the invention. The examples disclose further cut-off values that can be employed, and that are associated with specific advantageous when used in conjunction with specific time points of sample isolation. Events determining time points of sample isolation, such as the initial occurrence of symptoms in a patient, hospitalization of a patient or diagnosis of SARS infection, for example by a positive laboratory test result, are disclosed herein.

The present invention therefore provides a new, quick and reliable test for primary healthcare practitioners, such as doctors, nurses, etc., to quickly assess the risk of patient with symptoms of a SARS or of infection with a SARS-virus to develop a condition requiring hospitalization, such as sepsis.

In certain embodiments of the method of the invention, the condition requiring hospitalization is a viral infection-related complication, such as an infection, a nosocomial infection, sepsis and/or septic shock. In certain embodiments of the method of the invention, the condition comprises an infection, a nosocomial infection, sepsis and/or septic shock, preferably based on a respiratory infectious disease, urinary tract infectious disease, a skin infectious disease or an abdominal infectious disease.

It is particular advantage that the cut-off of proADM or fragment(s) thereof to be used in the context of the method of the invention can be used to rule-out hospitalization. Accordingly, the method enables a more accurate assessment of the prognosis/risk of a patient, depending on the situation of sample isolation and the further information available at that time, for example an increased risk of developing severe condition.

Depending on the result of the method of the present invention, embodiments of the method may comprise subsequent therapeutic decisions and/or therapeutic actions. Such therapeutic decisions may include the initiation, change or modification of medical treatment. Preferably, if the method of the present invention is indicative of development to a condition requiring treatment in hospital, suitable therapeutic measures, such as initiation or change of a certain medication, mechanical ventilation, surgery or fluid therapy may be initiated.

Any therapy, medical treatment or therapeutic action disclosed herein can be employed in the context of the method of the invention as a subsequent therapeutic decision or therapeutic action, in particular if the therapeutic measure is specifically administered in hospital, including but not limited to mechanical ventilation, intravenous fluid therapy, dialysis, management of electrolyte abnormalities (in particular potassium, calcium and phosphorus). Furthermore, a maintained intensive observation and care of the patient may be indicated potentially over extended periods of time, such as several day, weeks or even months. This may involve keeping or moving the patient to an ICU and/or prolonging the stay of the patient in an ICU.

On the other hand, if the result of the method of the present invention is indicative of the absence of risk of developing a condition requiring hospitalization, no specific treatment measures with respect to such complication may be required, or less serious, self-administrable treatments may be prescribed.

Embodiments of the Invention Relating to Patients that have been Diagnosed with SARS and that May be Critically Ill In a further aspect disclosed herein, the present invention relates to the provision of means for the prognosis, risk assessment and/or risk stratification of a subsequent adverse event in the health of a patient that has been diagnosed with SARS and that may be critically ill, in particular within a short time frame after initiating treatment.

The present invention therefore seeks to provide a method, kit and further means for therapy monitoring of a patient that has been diagnosed with SARS and that may be critically ill, as well as means for the prognosis, risk assessment and/or risk stratification of a subsequent adverse event in the health of a patient that has been diagnosed with SARS and that may be critically ill on the basis of proadrenomedullin (proADM) levels determined in a sample from a patient. One object of the invention is therefore the use of a biomarker or combination of biomarkers to distinguish a patient that has been diagnosed with SARS and that may be critically ill who has undergone or are undergoing treatment, who has a high risk of an adverse event, from a patient that has been diagnosed with SARS and that may be critically ill who has a low risk of a subsequent adverse event.

In embodiments, the invention therefore relates to a method for prognosing disease progression, wherein the method comprises prognosing a subsequent adverse event in the health of a patient that has been diagnosed with SARS, comprising providing a sample of said patient, wherein the sample is isolated from the patient after diagnosis and treatment initiation, determining a level of proadrenomedullin (proADM) or fragment(s) thereof in said sample, wherein said level of proADM or fragment(s) thereof indicates the likelihood of a subsequent adverse event in the health of said patient.

In embodiments, the present invention therefore relates to a method for therapy monitoring, comprising the prognosis, risk assessment and/or risk stratification of a subsequent adverse event in the health of a patient that has been diagnosed with SARS, comprising providing a sample of said patient, wherein the sample is isolated from the patient after diagnosis and preferably treatment initiation, determining a level of proADM or fragment(s) thereof in said sample, wherein said level of proADM or fragment(s) thereof correlates with the likelihood of a subsequent adverse event in the health of said patient.

In this aspect of the invention, the patients of the method of the present invention have already been diagnosed with SARS and are preferably already receiving treatment. The method of the present invention can therefore be used for monitoring the success of the treatment or therapy that has been initiated, on the basis of determining the likelihood of a subsequent adverse event. The therapy monitoring preferably involves the prognosis of an adverse event and/or the risk stratification or risk assessment of the patient with respect to a future adverse event, wherein this risk assessment and the determination of said risk is to be considered as a means of monitoring the initiated therapy.

Physicians or medical personnel who are treating patients that have been diagnosed with SARS can employ the method of the present invention in different clinical settings, such as primary care setting or, preferably, in a hospital setting, such as in an emergency department, or in an intensive care unit (ICU). The method is very useful to monitor the effect of a therapy that has been initiated on a patient that have been diagnosed with SARS and can be used to judge whether a patient under treatment is a high risk patient that should be under intense medical observation and should potentially receive additional therapeutic measures, or whether the patient is a low risk patient with an improving health state that might not require as intense observation and further treatment measures, possibly because the initiated treatment is successfully improving the state of the patient. Initial treatments of a patient that have been diagnosed with SARS may have a direct effect on the likelihood of adverse events in the health of the patient. As such, the assessment of risk/prognosis of a future adverse event provides feedback on or monitoring of the therapy instigated.

In the context of this method of the invention, the viral infection comprises preferably a coronavirus infection, such as an infection with a SARS-coronavirus. Preferably, the SARS-coronavirus comprises SARS-CoV2. In embodiments, the viral infection is not an influenza virus infection.

Furthermore, the patient may belong to a patient group with an increased risk of an adverse event in case of a SARS or an infection with a SARS-virus, such as patients with an age of 60 years or more, preferably 70 years or more, patients with long-term respiratory or lung disease, such as asthma, cystic fibrosis or chronic obstructive pulmonary disease (COPD), patients with long-term heart disease, such as heart failure, patients with long-term kidney disease, patients with long-term liver disease, such as hepatitis, patients with diabetes, patients with long-term neurological conditions, such as Parkinson's disease, motor neuron disease, multiple sclerosis (MS), cerebral palsy, or a learning disability, patients with splenic disease, such as sickle cell anemia or splenectomy, patients with a weakened immune system, such as patients with HIV or AIDS, or patients receiving immunosuppressive medication, patients with a body mass index (BMI) of 40 or above (severely obese patients), pregnant women, patients that had an organ transplantation taking immunosuppressive medication, cancer patients and in particular cancer patients receiving chemotherapy or radiotherapy.

The likelihood of the occurrence of a subsequent adverse event can be assessed on the comparison of the level of proADM or fragments thereof in the sample in comparison to a reference level (such as a threshold or cut-off value and/or a population average), wherein the reference level may correspond to proADM or fragments thereof in healthy patients, or in patients who have been diagnosed with SARS.

Accordingly, the method of the present invention can help to predict the likelihood of a subsequent adverse event in the health of the patient. This means, that the method of the invention can discriminate high risk patients, who are more likely to suffer from complications, or whose state will become more critical in the future, from low risk patients, whose health state is stable or even improving, so that it is not expected that they will suffer from an adverse event, such as death of the patient or a deterioration of the patient's clinical symptoms or signs, which might require certain therapeutic measures.

A particular advantage of the method of the present invention is that a patient who has been identified as a low risk patient by means of the method of the present invention could be more rapidly discharged from an ICU. Also, for low risk patients, the intensity and/or frequency of the observation of the health status of the patient could be decreased. Accordingly, the hospital or other medical institution in charge of the patient could more efficiently decide which patients require intensive medical care and observation. Consequently, the respective hospital or institution could, for example, more efficiently occupy ICU beds with high-risk patients. This would lead to an improved medical care for the high-risk patients, since the medical personnel could focus on such patients, while low risk patients could be discharged from the ICU. This would also lead to significant benefits from avoided costs for unnecessary measures that would otherwise be applied to low risk patients.

The time point when the patients have been diagnosed with SARS and the first treatment measures are initiated is defined as "time point 0", which may be the reference for the time point of isolation of the sample used for determining proADM or fragments thereof. If diagnosis of the patient and treatment initiation do not occur at the same time, time point 0 is the time point when the later of the two events of diagnosis and initiation of medical treatment occurs. Typically, diagnosis of patients suffering from SARS or from infection with a SARS-virus is immediately followed by or concomitant to initiation of therapy.

It was entirely surprising that the level of proADM or fragments thereof in a sample from the patient can provide critical information about the likelihood of the occurrence of a subsequent adverse event in the health of said patients. There has been no indication that a single measurement of proADM or fragments thereof after diagnosis and treatment initiation of a patient that has been diagnosed with SARS could provide such important information with respect to success of the ongoing treatment and prognosis of the health status of the patient.

The use of proADM or fragments thereof as a single parameter in embodiments of the present invention is advantageous over the use of clinical scores, since proADM levels can be determined fast and objectively, while determining clinical scores such as SOFA, SAPS II, APACHE II, PSI, CRB-65 and qSOFA requires more time for collecting several parameters that also involve patient examination and interrogation and subsequent analysis.

According to a preferred embodiment, the sample is isolated from said patient within 30 minutes after said diagnosis and treatment initiation, or at least 30 minutes, 1 hour, 2 hours, 6 hours, 12 hours, 24 hours, 4 days, 7 days or 10 days after said diagnosis and treatment initiation. Further possible time points of sample isolation include 2 days, 3 days, 4 days, 5 days, 6 days, 7 days, 8 days or 9 days after said diagnosis and treatment initiation. In other embodiments the sample is isolated from said patient 12-36 hours and/or 3-5 days after treatment initiation.

The fact that the level of proADM or fragments thereof at a time point as short as about 30 minutes after diagnosis and treatment initiation can provide such information was completely unexpected.

In embodiments, the sample is isolated from the patient within 30 minutes after said diagnosis and treatment initiation, or 30 minutes, 1 hour, 2 hours, 6 hours, 12 hours, 24 hours, 4 days, 7 days or 10 days after said diagnosis and treatment initiation.

In preferred embodiments of the method of the present invention said sample is isolated from said patient about 30 minutes, 1 hour, 2 hours, 3 hours, 4, hours, 5 hours, 6 hours, 7 hours, 8 hours, 9 hours, 10 hours, 11 hours, 12 hours, 14 hours, 16 hours, 18 hours, 20 hours 22 hours, 24 hours, 30 hours, 36 hours, 42 hours, 48 hours, 60 hours, 72 hours, 84 hours, 4 days, 5 days, 6 days, 7 days, 8 days 9 days or 10 days after said diagnosis and treatment initiation.

In other embodiments, the sample is isolated at time points after said diagnosis and initiating treatment of 30 minutes to 12 hours, 12-36 hours, 3-5 days, 7-14 days, 8-12 days, or 9-11 days.

Ranges between any given of the above values may be employed to define the time point of obtaining the sample.

In another preferred embodiment of the present invention, the patient has been diagnosed using at least one additional biomarker or a clinical score. It is particularly advantageous in the context of the present invention, if the initial diagnosis of SARS or of infection with a SARS-virus of the patient at time point 0 was based at least partially on the level of at least one biomarker or a determined clinical score.

In certain embodiments the present invention comprises the determination of additional parameters, such as markers, biomarkers, clinical scores or the like.

In preferred embodiments of the present invention, the adverse event in the health of said patient is death, preferably death within 2-30 days after diagnosis and treatment initiation, a new infection, such as a bacterial infection, respiratory failure, organ failure and/or a deterioration of clinical symptoms requiring a focus cleaning procedure, transfusion of blood products, infusion of colloids, emergency surgery, invasive mechanical ventilation and/or renal or liver replacement.

In preferred embodiments of the invention, said level of proADM or fragment(s) thereof correlates with the likelihood of a subsequent adverse event in the health of said patient within 1, 2, 3, 4, 5, 6, 7, 8, 9, 10, 11, 12, 13, 14, 15, 16, 17, 18, 19, or up to 30 days after diagnosis and treatment initiation.

In certain embodiments of the invention, the treatment received by the patient comprises one or more of symptomatic treatment, treatment to reduce fever and/or pain, anti-inflammatory treatment, antiviral treatment, antibiotic treatment, oxygen support, invasive mechanical ventilation, non-invasive mechanical ventilation, renal replacement therapy, vasopressor use, fluid therapy, extracorporeal blood purification and/or organ protection.

In preferred embodiments of the invention, the sample is selected from the group consisting of a blood sample, a serum sample, a plasma sample and/or a urine sample.

Preferably, the method is carried out in some embodiments by determining a level of proADM or fragment(s) thereof, wherein said determining of proADM comprises determining a level of MR-proADM in the sample. The employment of determining MR-proADM is preferred for any given embodiment described herein and may be considered in the context of each embodiment, accordingly. In preferred embodiments the "ADM fragment" may be considered to be MR-proADM.

In further embodiments of the invention the level of proADM or fragment(s) thereof correlates with the likelihood of a subsequent adverse event in the health of said patient. In a preferred embodiment the level of proADM or fragment(s) thereof positively correlates with the likelihood of a subsequent adverse event in the health of said patient. In other words, the higher the level of proADM determined, the greater the likelihood of a subsequent adverse event.

According to a preferred embodiment of the present invention, a low severity level of proADM or fragment(s) thereof is indicative of the absence of a subsequent adverse event, or indicates a low risk of a subsequent adverse event, wherein the low severity level is equal or below 2.25 nmol/l±20%, or a high severity level of proADM or fragment(s) thereof is indicative of a subsequent adverse event, or indicates a high risk of a subsequent adverse event, wherein the high severity level is above 2.25 nmol/l±20%.

According to a preferred embodiment of the present invention, a level of proADM or fragment(s) thereof equal or below 2.25 nmol/l±20% is indicative of the absence of a subsequent adverse event, or indicates a low risk of a subsequent adverse event, or a level of proADM or fragment(s) thereof above 2.25 nmol/l±20% is indicative of a subsequent adverse event, or indicates a high risk of a subsequent adverse event.

According to a preferred embodiment of the present invention, a low severity level of proADM or fragment(s) thereof is indicative of the absence of a subsequent adverse event, or indicates a low risk of a subsequent adverse event, wherein the low severity level is equal or below 2.5 nmol/l±20%, or a high severity level of proADM or fragment(s) thereof is indicative of a subsequent adverse event, or indicates a high risk of a subsequent adverse event, wherein the high severity level is above 2.5 nmol/l±20%.

According to a preferred embodiment of the present invention, a level of proADM or fragment(s) thereof equal or below 2.5 nmol/l±20% is indicative of the absence of a subsequent adverse event, or indicates a low risk of a subsequent adverse event, or a level of proADM or fragment(s) thereof above 2.5 nmol/l±20% is indicative of a subsequent adverse event, or indicates a high risk of a subsequent adverse event.

According to a preferred embodiment of the present invention, a low severity level of proADM or fragment(s) thereof is indicative of the absence of a subsequent adverse event, or indicates a low risk of a subsequent adverse event, wherein the low severity level is equal or below 1.5 nmol/l±20%, or a high severity level of proADM or fragment(s) thereof is indicative of a subsequent adverse event, or indicates a high risk of a subsequent adverse event, wherein the high severity level is above 1.5 nmol/l±20%.

According to a preferred embodiment of the present invention, a level of proADM or fragment(s) thereof equal or below 1.5 nmol/l±20% is indicative of the absence of a subsequent adverse event, or indicates a low risk of a subsequent adverse event, or a level of proADM or fragment(s) thereof above 1.5 nmol/l±20% is indicative of a subsequent adverse event, or indicates a high risk of a subsequent adverse event.

According to a preferred embodiment of the present invention, a low severity level of proADM or fragment(s) thereof is indicative of the absence of a subsequent adverse event, or indicates a low risk of a subsequent adverse event, wherein the low severity level is equal or below 0.87 nmol/l±20%, or a high severity level of proADM or fragment(s) thereof is indicative of a subsequent adverse event, or indicates a high risk of a subsequent adverse event, wherein the high severity level is above 0.87 nmol/l±20%.

According to a preferred embodiment of the present invention, a level of proADM or fragment(s) thereof equal or below 0.87 nmol/l±20% is indicative of the absence of a subsequent adverse event, or indicates a low risk of a subsequent adverse event, or a level of proADM or fragment(s) thereof above 0.87 nmol/l±20% is indicative of a subsequent adverse event, or indicates a high risk of a subsequent adverse event.

According to a preferred embodiment of the present invention, a low severity level of proADM or fragment(s) thereof is indicative of the absence of a subsequent adverse event, or indicates a low risk of a subsequent adverse event, wherein the low severity level is equal or below 0.75 nmol/l±20%, or a high severity level of proADM or fragment(s) thereof is indicative of a subsequent adverse event, or indicates a high risk of a subsequent adverse event, wherein the high severity level is above 0.75 nmol/l±20%.

According to a preferred embodiment of the present invention, a level of proADM or fragment(s) thereof equal or below 0.75 nmol/l±20% is indicative of the absence of a subsequent adverse event, or indicates a low risk of a subsequent adverse event, or a level of proADM or fragment(s) thereof above 0.75 nmol/l±20% is indicative of a subsequent adverse event, or indicates a high risk of a subsequent adverse event.

According to the present invention, the term "indicate" in the context of "indicative of a subsequent adverse event" and "indicative of the absence of a subsequent adverse event" is intended as a measure of risk and/or likelihood. Preferably, the "indication" of the presence or absence of an adverse event is intended as a risk assessment, and is typically not to be construed in a limiting fashion as to point definitively to the absolute presence or absence of said event.

Therefore, the term "indicative of the absence of a subsequent adverse event" or "indicative of a subsequent adverse event" can be understood as indicating a low or high risk of the occurrence of an adverse event, respectively. In some embodiments a low risk relates to a lower risk compared to proADM levels detected above the indicated values. In some embodiments a high risk relates to a higher risk compared to proADM levels detected below the indicated values.

Keeping the above in mind, the determination of high and low severity levels of proADM is however very reliable with respect to determining the presence or absence of a subsequent adverse event when using the cut-off values disclosed herein, such that the estimation of risk enables an appropriate action by a medical professional.

It was entirely surprising that a level of proADM or fragments thereof could be correlated with the likelihood of the presence or absence of a subsequent adverse event in the context of a patient that has been diagnosed with SARS and who was receiving treatment at this time point.

In one embodiment of the invention, a low severity level of proADM or fragment(s) thereof is indicative of the absence of a subsequent adverse event, wherein the low severity level is below a cut-off value in the range of 1.5 nmol/l and 4 nmol/l. Any value within these ranges may be considered as an appropriate cut-off value for a low severity levels of proADM or fragments thereof. For example, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0 nmol/l.

In further embodiments, a low severity level of proADM or fragment(s) thereof is indicative of the absence of a subsequent adverse event, wherein the low severity level is below a cut-off value in the range of 0.7 nmol/l and 1.5 nmol/l, for example, 0.7, 0.75, 0.8, 0.85, 0.9, 0.95, 1.0, 1.05, 1.1, 1.15, 1.2, 1.25, 1.3, 1.35, 1.4, 1.45, 1.5 nmol/l.

In one embodiment of the invention, a high severity level of proADM or fragment(s) thereof is indicative of a subsequent adverse event, wherein the high severity level is above a cut-off value in the range of 1.5 nmol/l and 4 nmol/l. Any value within these ranges may be considered as an appropriate cut-off value for a low seventy levels of proADM or fragments thereof. For example, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0 nmol/l.

In further embodiments, a high severity level of proADM or fragment(s) thereof is indicative of a subsequent adverse event, wherein the high severity level is above a cut-off value in the range of 0.7 nmol/l and 1.5 nmol/l, for example, 0.7, 0.75, 0.8, 0.85, 0.9, 0.95, 1.0, 1.05, 1.1, 1.15, 1.2, 1.25, 1.3, 1.35, 1.4, 1.45, 1.5 nmol/l.

In the embodiments described herein, the severity levels are defined preferably by cut-off values, that represent boundaries between low and high severity or risk levels. Any embodiments that present cut-offs therefore may use the format of a single cut-off value as a boundary between two severity levels.

According to a preferred embodiment of the present invention, a low severity level of proADM or fragment(s) thereof is indicative of the absence of a subsequent adverse event, wherein the low severity level is equal or below 2.25 nmol/l.

In embodiments of the invention, the patient is an intensive care unit (ICU)-patients, wherein.

the low severity level of proADM or fragment(s) thereof indicates discharging of said patient from ICU, or the high severity level of proADM or fragment(s) thereof indicates keeping said patient on the ICU and optionally modifying the treatment of the patient in the ICU.

It is a particular advantage of the present invention that based on the classification of the determined levels of proADM or fragments thereof it is possible to assess the probability of the occurrence of a future adverse event in the health of an ICU patient. Based on this assessment it is possible to adjust the next treatment options and decisions.

For example, if the level of proADM or fragments thereof falls into the category of a low severity level of proADM, the treating physician can decide with more confidence to discharge said patient from ICU, because it is unlikely that an adverse event in the health of said patient would occur, preferably, within the next 2-30 days. Accordingly, it might not be necessary to keep this patient on the ICU. It might also be possible to conclude that the ongoing treatment is successfully improving the health state of the patient, as assessed by a measurement of risk of an adverse event.

In contrast, if the determination of the level of proADM or fragments thereof of said ICU patient indicates a high severity level of proADM or fragments thereof, the treating physician should keep the patient on the ICU. Additionally, it should be considered to adjust the treatment of the patient, because it is likely that the current treatment is not improving the health state of the patient, which is why the patient is more likely to suffer form an adverse event in the future.

A treatment modification in the sense of the present invention would include, without limitation, an adjustment of the dose or administration regime of the ongoing medication. Change of the ongoing treatment to a different treatment, addition of a further treatment option to the ongoing treatment or stop of an ongoing treatment. Different treatments that can be applied to patients in the context of the present invention have been disclosed in the detailed description of this patent application.

According to a particularly preferred embodiment of the present invention the low severity level is equal or below 2.25 nmol/l, said sample is isolated from the ICU-patient 1 day or more after said diagnosis and treatment initiation, and the low severity level of proADM or fragment(s) thereof indicates discharging of said patient from ICU.

The present invention further relates to a method for therapy monitoring, comprising the prognosis, risk assessment and/or risk stratification of a subsequent adverse event in the health of a patient that has been diagnosed with SARS, comprising providing a sample of said patient, wherein the patient is an intensive care unit (ICU)-patient and medical treatment has been initiated, wherein the sample is isolated from the patient after admission to ICU and treatment initiation, determining a level of adrenomedullin (ADM) or fragment(s) thereof in said sample, wherein said level of proADM or fragment(s) thereof correlates with the likelihood of a subsequent adverse event in the health of said patient.

In the context of the method of the present invention relating to ICU-patients, the reference for the time point of isolation of the sample used for determining proADM or fragments thereof is the time point when the patients are admitted to the ICU and the first treatment measures are initiated (time point 0). This time point corresponds to the time point of diagnosis and treatment initiation in the method of the present invention relating to ICU patients that have been diagnosed as suffering from SARS or an infection with a SARS-virus.

All embodiments of the method of the present invention relating to patients that have been diagnosed with SARS are herewith also considered to correspond to embodiments of the method of the present invention relating to such patients being ICU-patients.

In embodiments, the patient is not an intensive care unit (ICU)-patient, such as a patient hospitalized in a non-ICU ward or an outpatient, wherein:

the low severity level of proADM or fragment(s) thereof indicates keeping said patient away from ICU admission, or the high severity level of proADM or fragment(s) thereof indicates transferring said patient to an ICU and optionally modifying the treatment of the patient in the ICU.

In embodiments of the method of the invention, the patient diagnosed with SARS is not an intensive care unit (ICU)-patients, but a patient hospitalized on a normal ward or an outpatient, wherein:

the low severity level of proADM or fragment(s) thereof indicates keeping said patient off ICU, or the high severity level of proADM or fragment(s) thereof indicates transferring said patient on an ICU and optionally modifying the treatment of the patient in the ICU wherein 2.25 nmol/l±20% is used as a threshold.

In embodiments, said sample is isolated from said patient 1 day or more after said diagnosis and treatment initiation. The time point of diagnosis and treatment initiation may be considered the time point of hospitalization of a patient. In embodiments, said sample is isolated on day 1 (within 24 hours) from presentation to medical personnel and/or hospitalization, or on day 1, day 2, day 3, day 4, day 5, day 6, day 7, day 8, day 9 or day 10 from hospitalization.

In embodiments, the alternative thresholds may be used, such as 0.75, 0.87, 1.5 or 2.5 nmol/l±20%. As shown in the examples, these thresholds are associated with specific advantageous, depending on intended medical conclusion and consequences to be drawn from the method of the invention.

The invention further relates to methods of treatment for the medical indications described herein, wherein the patient population to be treated is identified, stratified, monitored, prognosed, diagnosed or otherwise assessed using the methods described herein. Suitable treatments for the methods are disclosed herein. The present invention is therefore particularly advantageous in identifying patients with increased risk of having an adverse event and initiating preventative or risk-reducing treatments, or initiating treatments to address the presence of any given medical condition, preferably those understood as critical illness.

Embodiments Relating to PCT Determination

A further embodiment of the present invention comprises additionally determining a level of PCT or fragment(s) thereof in a sample isolated from the patient. In a preferred embodiment, the sample for determining a level of PCT or fragment(s) thereof is isolated before, at or after the time point of diagnosis and treatment initiation.

It is particularly advantageous to combine the determination of proADM or fragments thereof with the determination of PCT or fragments thereof in a sample, wherein the sample used for determining proADM may be the same or a different sample used for detecting PCT.

The additional determination of PCT is advantageous in the context of the methods disclosed herein since it is possible to rule out a bacterial infection on the basis of the determined PCT level. This is of particular importance since SARS patients are often at risk of bacterial coinfection.

The combined determination of proADM or fragments thereof with the determination of PCT or fragments thereof, whether in the same sample or in samples obtained at different time points, provides a synergistic effect with respect to the accuracy and reliability of determining the risk of a subsequent adverse event. These synergistic effects also exist for the combined assessment of proADM or fragments thereof with other markers or clinical scores, such as D-Dimer, Troponin, lactate, CRP, SOFA, SAPS II, APACHE II, NES, CRB-65, PSI score or other clinical assessments. For all embodiments of the invention disclosed herein comprising determining PCT, corresponding embodiments comprising instead of (or in addition to) PCT other relevant parameter, biomarker or clinical scores disclosed herein are herewith disclosed. Preferred biomarkers that can be determined in addition to proADM in the context of the invention comprise D-Dimer and Troponin.

According to a further preferred embodiment of the present invention, the method described herein comprises additionally determining a level of PCT or fragment(s) thereof in a first sample isolated from the patient, wherein said first sample is isolated before, at or after the time point of diagnosis and treatment initiation, determining a level of PCT or fragment(s) thereof in a second sample isolated from said patient, wherein the second sample has been isolated after the first sample, preferably within 30 minutes after isolation of the first sample or 30 minutes, 1 hour, 2 hours, 6 hours, 12 hours, 24 hours, 4 days, 7 or 10 days after isolation of the first sample, and determining a difference in the level of PCT or fragment(s) thereof in the second sample in comparison to the level of PCT or fragment(s) thereof in the first sample.

It is particularly advantageous to combine the determination of proADM or fragments thereof in a sample isolated from a patient with the determination of PCT or fragments thereof in a first sample and determining the level of PCT or fragments thereof in a second sample isolated after the first sample, wherein the sample used for the determination of proADM or fragments thereof may be the same of different than the first sample or the second sample used for determining PCT or fragments thereof.

In a preferred embodiment, the method described herein comprises additionally determining a level of PCT or fragment(s) thereof in a first sample isolated from the patient, wherein said first sample is isolated at or before the time point of diagnosis and treatment initiation (time point 0), determining a level of PCT or fragment(s) thereof in a second sample (corresponding to the sample of claim 1) isolated from said patient after said diagnosis and treatment initiation, preferably within 30 minutes, or at least 30 minutes, preferably 1 hour, 2 hours, 6 hours, 12 hours, 24 hours, 4 days, 7 days or 10 days after said diagnosis and treatment initiation, and determining whether a difference in the level of PCT or fragment(s) thereof in the second sample is evident in comparison to the level of PCT or fragment(s) thereof in the first sample.

It is particularly advantageous to combine the determination of proADM or fragments thereof (in a second sample) with the determination of PCT or fragments thereof in an earlier sample (first sample) that is isolated from said patient and that may be used for diagnosing said patient with SARS at time point 0 and determining the level of PCT or fragments thereof in a second sample isolated at a certain time point after diagnosis and treatment initiation, which is also preferably the same time point when proADM or fragments thereof are determined.

Determining a difference in the level of PCT or fragments thereof in the second sample in comparison to the first sample adds additional information to the information gained from the levels of proADM or fragments thereof in the second sample. Based on this combined information it might be possible to predict with a higher probability whether an adverse event in the health of said patient will occur as compared to predicting the likelihood of an adverse event purely on the information about the level of proADM or fragments thereof in the second sample. This represents a surprising finding, as biomarkers for sepsis are typically not synergistic or complementary, but represent mere alternative diagnostic markers.

In a preferred embodiment of the present invention, a lower level of PCT or fragment(s) thereof in the second sample compared to the first sample, and a low severity level of proADM or fragment(s) thereof, wherein the low severity level is equal or below 2.25 nmol/l±20%, is indicative of the absence of a subsequent adverse event, or a lower level of PCT or fragment(s) thereof in the second sample compared to the first sample, and a high severity level of proADM or fragment(s) thereof, wherein the high severity level is above 2.25 nmol/l±20%, is indicative of a subsequent adverse event.

In a preferred embodiment of the present invention, a lower level of PCT or fragment(s) thereof in the second sample compared to the first sample, and a low severity level of proADM or fragment(s) thereof, wherein the low severity level is equal or below 2.5 nmol/l±20%, is indicative of the absence of a subsequent adverse event, or a lower level of PCT or fragment(s) thereof in the second sample compared to the first sample, and a high severity level of proADM or fragment(s) thereof, wherein the high severity level is above 2.5 nmol/l±20%, is indicative of a subsequent adverse event.

In a preferred embodiment of the present invention, a lower level of PCT or fragment(s) thereof in the second sample compared to the first sample, and a low severity level of proADM or fragment(s) thereof, wherein the low severity level is equal or below 1.5 nmol/l±20%, is indicative of the absence of a subsequent adverse event, or a lower level of PCT or fragment(s) thereof in the second sample compared to the first sample, and a high severity level of proADM or fragment(s) thereof, wherein the high severity level is above 1.5 nmol/l±20%, is indicative of a subsequent adverse event.

In a preferred embodiment of the present invention, a lower level of PCT or fragment(s) thereof in the second sample compared to the first sample, and a low severity level of proADM or fragment(s) thereof, wherein the low severity level is equal or below 0.87 nmol/l±20%, is indicative of the absence of a subsequent adverse event, or a lower level of PCT or fragment(s) thereof in the second sample compared to the first sample, and a high severity level of proADM or fragment(s) thereof, wherein the high severity level is above 0.87 nmol/l±20%, is indicative of a subsequent adverse event.

In a preferred embodiment of the present invention, a lower level of PCT or fragment(s) thereof in the second sample compared to the first sample, and a low severity level of proADM or fragment(s) thereof, wherein the low severity level is equal or below 0.75 nmol/l±20%, is indicative of the absence of a subsequent adverse event, or a lower level of PCT or fragment(s) thereof in the second sample compared to the first sample, and a high severity level of proADM or fragment(s) thereof, wherein the high severity level is above 0.75 nmol/l±20%, is indicative of a subsequent adverse event.

In addition or as an alternative to PCT, other biomarkers, such as D-Dimer, Troponin, CRP or lactate, or clinical scores, such as one or more NEWS, SAPSII, CRB-65, qSOFA, SOFA, PSI, and APACHE II, can be used in the embodiments of the methods of the invention disclosed herein.

In the context of the present invention, determining a lower level of PCT (or another marker or clinical score) in the second sample as compared to the first sample can be indicative of decreasing levels of the respective marker or clinical score in the patient over the course of the initiated treatment. Conversely, elevated levels in the second sample as compared to the first sample might indicate increasing levels of the marker over the course of the treatment.

It was entirely surprising that a patient with a decrease of the level of PCT from the day of diagnosis and treatment initiation to a later time point at least 30 minutes after treatment has been initiated can still exhibit an elevated risk of a subsequent adverse event. In particular, this elevated risk is evident when a high severity level of proADM or fragments thereof has been determined.

It is believed that PCT is a marker for secondary bacterial infection in a critical ill patient, in particular for a patient with a viral infection of the respiratory tract, such as infection with a SARS-virus. Accordingly, decreasing PCT values over the course of a treatment are considered to indicate an improvement of the health status of the patient. However, as disclosed herein, it has become evident that despite a decreasing PCT value the patient can be at risk of suffering from a future adverse event, if the level of proADM or fragments thereof at the later time point is a high severity level. Accordingly, the treating physician can adjust the treatment of such a patient that would have not been identified as a high-risk patient without determining proADM or fragments thereof in the second sample.

On the other hand, a physician can be confident that an adverse event is unlikely to occur when the level of PCT is decreasing over the course of the treatment while the level of proADM or fragments thereof in the second sample is a low severity level of proADM or fragments thereof. Accordingly, such patients can be identified to be low-risk patients. It was entirely surprising that the combination of the determination of the change of PCT levels over the course of the treatment of a patient that has been diagnosed with SARS with the determination of proADM levels at the later time point leads to an improved treatment monitoring, prognosis and risk assessment for the occurrence of a future adverse event in the health of a patient.

According to another preferred embodiment of the method described herein, an elevated level of PCT or fragment(s) thereof in the second sample compared to the first sample, and a low severity level proADM or fragment(s) thereof, wherein the low severity level is equal or below 2.25 nmol/l±20%, is indicative of the absence of a subsequent adverse event, or an elevated level of PCT or fragment(s) thereof in the second sample compared to the first sample, and a high severity level of proADM or fragment(s) thereof, wherein the high severity level is above 2.25 nmol/l±20%, is indicative of a subsequent adverse event.

According to another preferred embodiment of the method described herein, an elevated level of PCT or fragment(s) thereof in the second sample compared to the first sample, and a low severity level proADM or fragment(s) thereof, wherein the low severity level is equal or below 2.5 nmol/l±20%, is indicative of the absence of a subsequent adverse event, or an elevated level of PCT or fragment(s) thereof in the second sample compared to the first sample, and a high severity level of proADM or fragment(s) thereof, wherein the high severity level is above 2.5 nmol/l±20%, is indicative of a subsequent adverse event.

According to another preferred embodiment of the method described herein, an elevated level of PCT or fragment(s) thereof in the second sample compared to the first sample, and a low severity level proADM or fragment(s) thereof, wherein the low severity level is equal or below 1.5 nmol/l±20%, is indicative of the absence of a subsequent adverse event, or an elevated level of PCT or fragment(s) thereof in the second sample compared to the first sample, and a high severity level of proADM or fragment(s) thereof, wherein the high severity level is above 1.5 nmol/l±20%, is indicative of a subsequent adverse event.

According to another preferred embodiment of the method described herein, an elevated level of PCT or fragment(s) thereof in the second sample compared to the first sample, and a low severity level proADM or fragment(s) thereof, wherein the low severity level is equal or below 0.87 nmol/l±20%, is indicative of the absence of a subsequent adverse event, or an elevated level of PCT or fragment(s) thereof in the second sample compared to the first sample, and a high severity level of proADM or fragment(s) thereof, wherein the high severity level is above 0.87 nmol/l±20%, is indicative of a subsequent adverse event.

According to another preferred embodiment of the method described herein, an elevated level of PCT or fragment(s) thereof in the second sample compared to the first sample, and a low severity level proADM or fragment(s) thereof, wherein the low severity level is equal or below 0.75 nmol/l±20%, is indicative of the absence of a subsequent adverse event, or an elevated level of PCT or fragment(s) thereof in the second sample compared to the first sample, and a high severity level of proADM or fragment(s) thereof, wherein the high severity level is above 0.75 nmol/l±20%, is indicative of a subsequent adverse event.

It is a great advantage of the present invention that it is possible to identify low risk patients in the group of patients that have been diagnosed with SARS based on the low severity level of proADM in the second sample, even if the level of PCT is increasing over the course of the treatment of the patient. This was entirely surprising, as it was believed that increasing levels of PCT indicate that the state of a patients that have been diagnosed with SARS is deteriorating and therefore the occurrence of an adverse event would have been assumed. Accordingly, a successful treatment might have been stopped and replaced by a modified or different treatment. The additional determination of proADM at the later time point allows the identification of low-risk patients within the group of patients with increasing PCT levels, which is a great advantage of the present invention.

On the other hand, it is possible to identify high-risk patients with increasing PCT levels and a high severity level of proADM or fragments thereof, which represent a more accurate identification of such patients that a likely to suffer from an adverse event in the future. Accordingly, the treatment of these patients could be adjusted while minimizing the risk that this patient might have been a low-risk patient.

In one embodiment the invention additionally comprises informing the patient of the results of the diagnostic method described herein.

A preferred embodiment of the method of the present invention comprises additionally determining a level of proADM or fragment(s) thereof in a first sample isolated from the patient, wherein said first sample is isolated before, at or after the time point of diagnosis and treatment initiation, and determining a level of proADM or fragment(s) thereof in a second sample isolated from said patient, wherein said second sample has been isolated after the first sample and after the time point of diagnosis and treatment initiation, preferably within 30 minutes after isolation of the first sample or 30 minutes, 1 hour, 2 hours, 6 hours, 12 hours, 24 hours, 4 days, 7 or 10 days after isolation of the first sample, and determining whether a difference in the level of proADM or fragment(s) thereof in the second sample in comparison to the level of proADM or fragment(s) thereof in the first sample is evident.

The first and the second sample used for determining a level of proADM or fragment(s) thereof may be the same of different from the first and the second sample used for determining a level of PCT or fragment(s) thereof.

A preferred embodiment of the method of the present invention comprises additionally determining a level of proADM or fragment(s) thereof in a first sample isolated from the patient, wherein said first sample is isolated at or before the time point of diagnosis and treatment initiation (time point 0), and determining a level of proADM or fragment(s) thereof in a second sample isolated after diagnosis and treatment initiation, preferably within 30 minutes, or after 30 minutes, 1 hour, 2 hours, 6 hours, 12 hours, 24 hours, 4 days, 7 or 10 days after said diagnosis and treatment initiation, and determining whether a difference in the level of proADM or fragment(s) thereof in the second sample in comparison to the level of proADM or fragment(s) thereof in the first sample is evident.

A further preferred embodiment of the method of the present invention comprises additionally determining a level of proADM or fragment(s) thereof and optionally PCT or fragment(s) thereof in a first sample isolated from the patient, wherein said first sample is isolated at or before the time point of diagnosis and treatment initiation (time point 0), and determining a level of proADM or fragment(s) thereof and optionally PCT or fragment(s) thereof in a second sample isolated from said patient after said diagnosis and treatment initiation, preferably within 30 minutes or at least 30 minutes after diagnosis and treatment initiation, preferably 1 hour, 2 hours, 6 hours, 12 hours, 24 hours, 4 days, 7 or 10 days after said diagnosis and treatment initiation, and determining a difference in the level of proADM or fragment(s) thereof and/or a difference in the level of PCT or fragments thereof in the second sample in comparison to the level of proADM or fragment(s) thereof in the first sample.

It was surprising that the determination of the change of the levels of proADM or fragments thereof from the time point of diagnosis and treatment initiation to a later time point can provide additional information with respect to the occurrence of a future adverse event in the health of a patient that has been diagnosed with SARS. It is a great advantage of this embodiment of the present invention that the same sample that is used for the determining of a diagnostic marker at time point 0 can also be used for determining the baseline level of proADM or fragments thereof, which can be compared to the level of proADM or fragments thereof at a later time point after diagnosis and treatment initiation. By determining the change of the level of proADM or fragments thereof of the course of patient treatment the accuracy of predicting the occurrence of an adverse event in the health of the patient can be further increased.

In one embodiment of the method described herein, an elevated level of proADM or fragment(s) thereof in the second sample compared to the first sample is indicative of a subsequent adverse event.

It was surprising that based on the change of the level of proADM or fragments thereof it is possible to confidently predict the likelihood of the occurrence of an adverse event in the health of the patient without determining further markers. An increase of the level or severity level of proADM or fragments thereof from the time point of diagnosis and treatment initiation indicates that it is likely that an adverse event will occur. Accordingly, based on the change of proADM or fragments thereof over the course of the treatment a physician can decide whether to change or modify the treatment of the patient or to stick to the initial treatment.

In a preferred embodiment of the method of the present invention an elevated level of proADM or fragment(s) thereof and an elevated level of PCT or fragment(s) thereof in the second sample compared to the first sample is indicative of a subsequent adverse event, and/or an elevated level of proADM or fragment(s) thereof and a lower level of PCT or fragment(s) thereof in the second sample compared to the first sample is indicative of a subsequent adverse event.

In preferred embodiments of the present invention an elevated level of proADM or fragments thereof in the second sample as compared to the first sample relates to an elevated severity level of proADM or fragments thereof. Conversely, in preferred embodiments of the present invention a lower level of proADM or fragments thereof in the second sample as compared to the first sample refer to a lower severity level of proADM or fragments thereof in the second sample as compared to the first sample.

It is a great advantage that based on the change in the level of proADM or fragments thereof in combination with the determined change of PCT or fragments thereof over the course of treatment of a patient that has been diagnosed with SARS the likelihood of an adverse event in the health of the patient can be determined. Accordingly, it is possible to confidently identify high-risk patients and low-risk patients based on the changes of these two markers. It was particularly surprising that decreasing PCT levels can be associated with an increased likelihood of a subsequent adverse event, if they coincide with increasing levels of proADM or fragments thereof.

According to a preferred embodiment of the present invention, the patients are intensive care unit (ICU)-patients, and
a lower level of PCT or fragment(s) thereof in the second sample compared to the first sample, and a low severity level of proADM or fragment(s) thereof, wherein the low severity level is equal or below 2.25 nmol/l±20%, indicates discharging of said patient from ICU;
a lower level of PCT or fragment(s) thereof in the second sample compared to the first sample, and a high severity level of proADM or fragment(s) thereof, wherein the high severity level is above 2.25 nmol/l±20%, indicates keeping the patient in the ICU and optionally modifying the treatment of the patient;
an elevated level of PCT or fragment(s) thereof in the second sample compared to the first sample, and a low severity level proADM or fragment(s) thereof, wherein the low severity level is equal or below 2.25 nmol/l±20%, indicates discharging of said patient from ICU; or
an elevated level of PCT or fragment(s) thereof in the second sample compared to the first sample, and a high severity level of proADM or fragment(s) thereof, wherein the high severity level is above 2.25 nmol/l±20%, indicates keeping the patient in the ICU and optionally modifying the treatment of the patient.

According to a preferred embodiment of the present invention, the patients are intensive care unit (ICU)-patients, and
a lower level of PCT or fragment(s) thereof in the second sample compared to the first sample, and a low severity level of proADM or fragment(s) thereof, wherein the low severity level is equal or below 2.5 nmol/l±20%, indicates discharging of said patient from ICU;
a lower level of PCT or fragment(s) thereof in the second sample compared to the first sample, and a high severity level of proADM or fragment(s) thereof, wherein the high severity level is above 2.5 nmol/l±20%, indicates keeping the patient in the ICU and optionally modifying the treatment of the patient;
an elevated level of PCT or fragment(s) thereof in the second sample compared to the first sample, and a low severity level proADM or fragment(s) thereof, wherein the low severity level is equal or below 2.5 nmol/l±20%, indicates discharging of said patient from ICU; or
an elevated level of PCT or fragment(s) thereof in the second sample compared to the first sample, and a high severity level of proADM or fragment(s) thereof, wherein the high severity level is above 2.5 nmol/l±20%, indicates keeping the patient in the ICU and optionally modifying the treatment of the patient.

According to a preferred embodiment of the present invention, the patients are intensive care unit (ICU)-patients, and
a lower level of PCT or fragment(s) thereof in the second sample compared to the first sample, and a low severity level of proADM or fragment(s) thereof, wherein the low severity level is equal or below 1.5 nmol/l±20%, indicates discharging of said patient from ICU;
a lower level of PCT or fragment(s) thereof in the second sample compared to the first sample, and a high severity level of proADM or fragment(s) thereof, wherein the high severity level is above 1.5 nmol/l±20%, indicates keeping the patient in the ICU and optionally modifying the treatment of the patient;
an elevated level of PCT or fragment(s) thereof in the second sample compared to the first sample, and a low severity level proADM or fragment(s) thereof, wherein the low severity level is equal or below 1.5 nmol/l±20%, indicates discharging of said patient from ICU; or
an elevated level of PCT or fragment(s) thereof in the second sample compared to the first sample, and a high severity level of proADM or fragment(s) thereof, wherein the high severity level is above 1.5 nmol/l±20%, indicates keeping the patient in the ICU and optionally modifying the treatment of the patient.

According to a preferred embodiment of the present invention, the patients are intensive care unit (ICU)-patients, and
a lower level of PCT or fragment(s) thereof in the second sample compared to the first sample, and a low severity level of proADM or fragment(s) thereof, wherein the low severity level is equal or below 0.87 nmol/l±20%, indicates discharging of said patient from ICU;
a lower level of PCT or fragment(s) thereof in the second sample compared to the first sample, and a high severity level of proADM or fragment(s) thereof, wherein the high severity level is above 0.87 nmol/l±20%, indicates keeping the patient in the ICU and optionally modifying the treatment of the patient;
an elevated level of PCT or fragment(s) thereof in the second sample compared to the first sample, and a low severity level proADM or fragment(s) thereof, wherein the low severity level is equal or below 0.87 nmol/l±20%, indicates discharging of said patient from ICU; or
an elevated level of PCT or fragment(s) thereof in the second sample compared to the first sample, and a high severity level of proADM or fragment(s) thereof, wherein the high severity level is above 0.87 nmol/l±20%, indicates keeping the patient in the ICU and optionally modifying the treatment of the patient.

According to a preferred embodiment of the present invention, the patients are intensive care unit (ICU)-patients, and
a lower level of PCT or fragment(s) thereof in the second sample compared to the first sample, and a low severity level of proADM or fragment(s) thereof, wherein the low severity level is equal or below 0.75 nmol/l±20%, indicates discharging of said patient from ICU;

a lower level of PCT or fragment(s) thereof in the second sample compared to the first sample, and a high severity level of proADM or fragment(s) thereof, wherein the high severity level is above 0.75 nmol/l±20%, indicates keeping the patient in the ICU and optionally modifying the treatment of the patient;

an elevated level of PCT or fragment(s) thereof in the second sample compared to the first sample, and a low severity level proADM or fragment(s) thereof, wherein the low severity level is equal or below 0.75 nmol/l±20%, indicates discharging of said patient from ICU; or an elevated level of PCT or fragment(s) thereof in the second sample compared to the first sample, and a high severity level of proADM or fragment(s) thereof, wherein the high severity level is above 0.75 nmol/l±20%, indicates keeping the patient in the ICU and optionally modifying the treatment of the patient.

It is advantageous that by means of a combined analysis of the change in the level of PCT or fragments thereof and the severity level of proADM or fragments thereof at the time point of the isolation of the second sample (the later time point) in an ICU patient it can be decided whether a patient is a low-risk patient that can be discharged from ICU while maintaining the ongoing treatment, or whether a patient is a high-risk patient that requires a modification or adjustment of the current therapy on ICU to prevent the occurrence of an adverse event that is indicated by the respective combination of the change in PCT levels and the current severity level of proADM

Embodiments Relating to a Kit of the Present Invention

A further aspect of the invention relates to a kit for carrying out the method as described herein.

In one embodiment, the kit comprises:

a. detection reagents for determining the level of proADM or fragment(s) thereof in a sample from a patient, and b. reference data for the risk of a patient as to whether a disease progression to a condition that requires hospitalization will occur, in particular reference data for a risk threshold or cut-off value, wherein said reference data is preferably stored on a computer readable medium and/or employed in the form of computer executable code configured for comparing the determined levels of proADM or fragment(s) thereof with the risk threshold or cut-off value, c. optionally detection reagents for determining the presence of SARS or of infection with a SARS-virus, preferably detection reagents for the presence of a corona-virus infection, such as a SARS-CoV2 infection;

d. and optionally, detection reagents for determining the level of at least one additional parameter or biomarker or fragment(s) thereof, preferably PCT, D-Dimer, Troponin, body weight and/or age, in a sample from a patient, and reference data, such as reference levels for said at least one additional biomarker, preferably PCT, for a risk threshold or cut-off value, wherein said reference data is preferably stored on a computer readable medium and/or employed in the form of computer executable code, such as an algorithm, configured for comparing the determined levels of the at least one additional biomarker or fragment(s) thereof with the threshold or cut-off value.

In embodiments of the kit of the invention, the reference data include a threshold of cut-off value of 0.87 nmol/l±20%, wherein a low risk level of proADM level or fragment(s) thereof of equal or below 0.87 nmol/l±20% in the sample from the patient indicates that the patient is not at risk of a disease progression to a condition that requires hospitalization, and/or wherein a high risk level of proADM level or fragment(s) thereof of above 0.87 nmol/l±20% in the sample from the patient indicates that the patient is at risk of a disease progression to a condition that requires hospitalization. In embodiments of the kit, said reference data including the cut-off value of 0.87 nmol/l±20% are provided on a computer executable code configured for comparing the determined levels of proADM or fragment(s) thereof with the risk threshold or cut-off value and may optionally provide a treatment recommendation including the options of hospitalization of the patient or release of the patient from (constant) medical supervision, depending on the determined level of proADM.

In embodiments of the kit of the invention, the reference data include a threshold of cut-off value of 0.93 nmol/l±20%, wherein a low risk level of proADM level or fragment(s) thereof of equal or below 0.93 nmol/l±20% in the sample from the patient indicates that the patient is not at risk of a disease progression to a condition that requires hospitalization, and/or wherein a high risk level of proADM level or fragment(s) thereof of above 0.93 nmol/l±20% in the sample from the patient indicates that the patient is at risk of a disease progression to a condition that requires hospitalization. In embodiments of the kit, said reference data including the cut-off value of 0.93 nmol/l±20% are provided on a computer executable code configured for comparing the determined levels of proADM or fragment(s) thereof with the risk threshold or cut-off value and may optionally provide a treatment recommendation including the options of hospitalization of the patient or release of the patient from (constant) medical supervision, depending on the determined level of proADM.

In further embodiments of the kit of the invention, the reference data include additionally or alternatively a threshold of cut-off value of 2.25 nmol/l±20%, wherein a low severity level of proADM level or fragment(s) thereof of equal or below 2.25 nmol/l±20% in the sample from the patient indicates discharging of said patient from ICU, and/or wherein a high severity level of proADM level or fragment(s) thereof of above 2.25 nmol/l±20% in the sample from the patient indicates keeping said patient on the ICU and optionally modifying the treatment of the patient in the ICU. In embodiments of the kit, said reference data including the cut-off value of 2.25 nmol/l±20% are provided on a computer executable code configured for comparing the determined levels of proADM or fragment(s) thereof with the risk threshold or cut-off value and may optionally provide a treatment recommendation including the options of keeping or discharging of the patient from an ICU, depending on the determined level of proADM.

In further embodiments of the kit of the invention, the reference data include additionally or alternatively a threshold of cut-off value of 2.5 nmol/l±20%, wherein a low severity level of proADM level or fragment(s) thereof of equal or below 2.5 nmol/l±20% in the sample from the patient indicates discharging of said patient from ICU, and/or wherein a high severity level of proADM level or fragment(s) thereof of above 2.5 nmol/l±20% in the sample from the patient indicates keeping said patient on the ICU and optionally modifying the treatment of the patient in the
ICU. In embodiments of the kit, said reference data includ-
ing the cut-off value of 2.25 nmol/l±20% are provided on a
computer executable code configured for comparing the
determined levels of proADM or fragment(s) thereof with
the risk threshold or cut-off value and may optionally
provide a treatment recommendation including the options
of keeping or discharging of the patient from an ICU,
depending on the determined level of proADM.

In further embodiments of the kit of the invention, the
reference data include additionally or alternatively a thresh-
old of cut-off value of 1.5 nmol/l±20%, wherein a low
severity level of proADM level or fragment(s) thereof of
equal or below 1.5 nmol/l±20% in the sample from the
patient indicates discharging of said patient from ICU,
and/or wherein a high severity level of proADM level or
fragment(s) thereof of above 1.5 nmol/l±20% in the sample
from the patient indicates keeping said patient on the ICU
and optionally modifying the treatment of the patient in the
ICU. In embodiments of the kit, said reference data including the cut-off value of 1.5 nmol/l±20% are provided on a
computer executable code configured for comparing the
determined levels of proADM or fragment(s) thereof with
the risk threshold or cut-off value and may optionally
provide a treatment recommendation including the options
of keeping or discharging of the patient from an ICU,
depending on the determined level of proADM.

In further embodiments of the kit of the invention, the
reference data include additionally or alternatively a thresh-
old of cut-off value of 0.75 nmol/l±20%, wherein a low
severity level of proADM level or fragment(s) thereof of
equal or below 0.75 nmol/l±20% in the sample from the
patient indicates discharging of said patient from ICU,
and/or wherein a high severity level of proADM level or
fragment(s) thereof of above 0.75 nmol/l±20% in the sample
from the patient indicates keeping said patient on the ICU
and optionally modifying the treatment of the patient in the
ICU. In embodiments of the kit, said reference data includ-
ing the cut-off value of 0.75 nmol/l±20% are provided on a
computer executable code configured for comparing the
determined levels of proADM or fragment(s) thereof with
the risk threshold or cut-off value and may optionally
provide a treatment recommendation including the options
of keeping or discharging of the patient from an ICU,
depending on the determined level of proADM.

In preferred embodiments, the kit of the invention is a kit
for carrying out an in vitro method for therapy guidance,
stratification and/or control in a patient showing mild symp-
toms of SARS or of infection with a SARS-virus corre-
sponding to a qSOFA score of 0 or 1 and/or a patient with symptoms of SARS or of infection with a SARS-virus that
shows not clinical symptoms for a viral and/or bacterial
pneumonia, ARDS, respiratory failure, blood stream infec-
tion, a sepsis, a severe sepsis and/or septic shock.

Furthermore, the reference data of the kit can include a
reference range of levels of proADM or fragment(s) thereof
between 0.5 nm/L±20% and 0.87 nmol/L±20%. This range
of proADM levels represented a serious challenge for medi-
cal practitioners and/or medical personnel since it may
indicate the presence of an infectious disease in a patient and
before the present invention it was unclear whether patients
with a proADM level falling within this range would require
hospitalization.

However, using the kit and method of the present inven-
tion it is possible to base the decision about hospitalization
of such patients on objective criteria, such as the reference
data of the kit. The reference data of the kit can be provided on a computer executable code configured for comparing the
determined levels of proADM or fragment(s) thereof with
said reference range, wherein the computer executable code
can provide a treatment recommendation including the
options of hospitalization of the patient if the determined
level of ADM is above the reference range or release of the
patient from (constant) medical supervision if the deter-
mined level is inside or below the reference range.

In some embodiments, the features of the kit may be
considered to include those features used in characterizing
the methods of the invention, and vice versa.

General Embodiments of the Methods of the
Invention

The cut-off values disclosed herein refer preferably to
measurements of the protein level of proADM or fragments
thereof in a blood sample, preferably a whole blood sample
or plasma or serum sample obtained from a patient, by
means of the Thermo Scientific BRAHMS KRYPTOR
assay. Accordingly, the values disclosed herein may vary to
some extent depending on the detection/measurement
method employed, and the specific values disclosed herein
are intended to also read on the corresponding values
determined by other methods.

In embodiments of the invention, the cut-off value of
proADM or fragment(s) thereof that may define either a low
or a high severity level, may be any value around 0.87
nmol/L±20%. In other embodiments, the cut-off value of
proADM or fragment(s) thereof that may define either a low
or a high severity level, may be any value around 0.87
nmol/L±preferably 15%, or 12%, or 10%, or 9, 8, 7, 6, 5, 4,
3, 2, or 1%.

Any value within this range (ie within the window of
variation of the 0.87 nmol/L value) may be considered an
appropriate cut-off value between high and low proADM
severity levels.

In aspects of the invention, the cut-off value of proADM
or fragment(s) thereof that may define either a low or a high
severity or risk level, may be any value around 0.93 nmol/
L±20%. In other embodiments, the cut-off value of proADM
or fragment(s) thereof that may define either a low or a high
severity level, may be any value around 0.93 nmol/
L±preferably 15%, or 12%, or 10%, or 9, 8, 7, 6, 5, 4, 3, 2,
or 1%.

Any value within this range (ie within the window of
variation of the 0.93 nmol/L value) may be considered an
appropriate cut-off value between high and low proADM
severity levels.

In aspects of the invention, the cut-off value of proADM
or fragment(s) thereof that may define either a low or a high
severity or risk level, may be any value around 2.25 nmol/
L±20%. In other embodiments, the cut-off value of proADM
or fragment(s) thereof that may define either a low or a high
severity level, may be any value around 2.25 nmol/
L±preferably 15%, or 12%, or 10%, or 9, 8, 7, 6, 5, 4, 3, 2,
or 1%.

Any value within this range (ie within the window of
variation of the 2.25 nmol/L value) may be considered an
appropriate cut-off value between high and low proADM
severity levels.

In aspects of the invention, the cut-off value of proADM
or fragment(s) thereof that may define either a low or a high
severity or risk level, may be any value around 2.5 nmol/
l±20%. In other embodiments, the cut-off value of proADM
or fragment(s) thereof that may define either a low or a high severity level, may be any value around 2.5 nmol/L±preferably 15%, or 12%, or 10%, or 9, 8, 7, 6, 5, 4, 3, 2, or 1%.

Any value within this range (ie within the window of variation of the 2.5 nmol/L value) may be considered an appropriate cut-off value between high and low proADM severity levels.

In aspects of the invention, the cut-off value of proADM or fragment(s) thereof that may define either a low or a high severity or risk level, may be any value around 1.5 nmol/L±20%. In other embodiments, the cut-off value of proADM or fragment(s) thereof that may define either a low or a high severity level, may be any value around 1.5 nmol/L±preferably 15%, or 12%, or 10%, or 9, 8, 7, 6, 5, 4, 3, 2, or 1%.

Any value within this range (ie within the window of variation of the 1.5 nmol/L value) may be considered an appropriate cut-off value between high and low proADM severity levels.

In aspects of the invention, the cut-off value of proADM or fragment(s) thereof that may define either a low or a high severity or risk level, may be any value around 0.75 nmol/L±20%. In other embodiments, the cut-off value of proADM or fragment(s) thereof that may define either a low or a high severity level, may be any value around 0.75 nmol/L±preferably 15%, or 12%, or 10%, or 9, 8, 7, 6, 5, 4, 3, 2, or 1%.

Any value within this range (ie within the window of variation of the 0.75 nmol/L value) may be considered an appropriate cut-off value between high and low proADM severity levels.

Furthermore, values below such a cut-off value may be indicative of the absence of significant risk of developing a condition requiring hospitalization, and values equal or above such a cut-off value may be indicative of developing a condition requiring hospitalization.

In the context of the methods of the invention disclosed herein, appropriate cut-off levels that may be used in the context of the present invention, comprise, without limitation, any value between 0.7 and 3.0 nmol/L. Other values include 0.72, 0.74, 0.76, 0.80, 0.82, 0.84, 8.60, 0.88, 0.90, 0.92, 0.94, 0.96, 0.98, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, and 2.95 nmol/L, or a value in between these values, or range using these values as an end point.

In embodiments of the invention, deviations from these possible cut-off values are also claimed, such as deviations of ±30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1%.

In the embodiments described herein, the severity levels are defined preferably by one or more cut-off values, that represent a boundary between low and high severity levels. Any embodiments that present cut-offs therefore may use the format of a single cut-off value as a boundary between two severity levels, or a single cutoff level for each severity level.

In embodiments the invention additionally comprises informing the patient of the results of the method described herein. In embodiments of the invention, the patient is at least 18 years old.

In embodiments of the invention, the sample is selected from the group consisting of a blood sample, a serum sample, a plasma sample and/or a urine sample. Determining proADM or fragment(s) thereof in blood, serum or plasma is particularly advantageous since it has been shown to be particularly accurate. Furthermore, these samples reflect the actual status of the patient at a given time-point very accurately.

In embodiments of the invention, determining a level of proADM or fragment(s) thereof comprises determining a level of MR-proADM in the sample. The employment of determining MR-proADM is preferred for any given embodiment described herein and may be considered in the context of each embodiment, accordingly. In preferred embodiments the "ADM fragment" may be considered to be MR-proADM.

According to certain embodiments, the method of the invention additionally comprises determining a level of at least one additional biomarker or fragment(s) thereof in a sample from said patient, wherein the at least one additional biomarker preferably is PCT or fragment(s) thereof and/or lactate, and/or determining at least one clinical score, wherein the at least one clinical score is preferably SOFA, qSOFA, PSI, APACHE II and/or CRB-65, wherein the level of the at least one additional biomarker and/or the at least one clinical score, and the level of proADM or fragment(s) thereof is indicative of whether hospitalization is required, or if the patient is at risk of developing a condition requiring treatment in hospital.

Further additional markers that may be determined in the context of the present invention comprise lactate and CRP. Clinical scores that may be determined in the context of the present invention comprise SI score (systemic inflammation score), SOFA, qSOFA, SIRS, SAPS II, APACHE II, CRB-65. PSI.

Determining proADM or fragment(s) thereof, and at least one clinical score, such as SOFA, PSI or CRB-65, in the context of the method of the invention turned out to provide further accuracy with respect to prognosis of a subsequent condition requiring hospital admission.

In further embodiments, the at least one additional biomarker is at least one marker of PCT, lactate, rhabdomyolysis, such as creatine kinase (CK), lactate dehydrogenase (LDH), creatinine, myoglobin, aldolase, troponin, carbonic anhydrase type 3, fatty acid-binding protein (FABP), transaminases or potassium.

The detection reagents for determining the level of proADM or fragment(s) thereof, and optionally for determining the level of PCT, lactate and/or C-reactive protein or fragment(s) thereof, are preferably selected from those necessary to perform the method, for example antibodies directed to ADM, suitable labels, such as fluorescent labels, preferably two separate fluorescent labels suitable for application in the KRYPTOR assay, sample collection tubes.

The embodiments and features disclosed in the context of the methods of the invention also apply to the kit of the present invention and vice versa.

In one embodiment of the methods described herein the level of proADM or fragment(s) thereof and optionally additionally other biomarkers such as for example PCT or fragment(s) thereof is determined using a method selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers.

The method according to the present invention can furthermore be embodied as a homogeneous method, wherein the sandwich complexes formed by the antibody/antibodies and the marker, e.g., the proADM or a fragment thereof, which is to be detected remains suspended in the liquid phase. In this case it is preferred, that when two antibodies are used, both antibodies are labelled with parts of a detection system, which leads to generation of a signal or triggering of a signal if both antibodies are integrated into a single sandwich.

Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733 A, EP-B1 0 180 492 or EP-B1 0 539 477 and the prior art cited therein. In this way, measurements in which only reaction products comprising both labelling components in a single immune-complex directly in the reaction mixture are detected, become possible.

For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of the proADM protein or a fragment thereof, and/or the level of any further marker of the herein provided method are determined. In particular preferred aspects, the diagnostic device is KRYPTOR®.

In one embodiment of the method described herein the method is an immunoassay and wherein the assay is performed in homogeneous phase or in heterogeneous phase.

In further embodiments of the method described herein, the method additionally comprises a molecular analysis of a sample from said patient for detecting an infection. The sample used for the molecular analysis for detecting an infection preferably is a blood sample. In a preferred embodiment the molecular analysis is a method aiming to detect one or more biomolecules derived from a pathogen. Said one or more biomolecule may be a nucleic acid, protein, sugar, carbohydrates, lipid and or a combination thereof such as glycosylated protein, preferably a nucleic acid. Said biomolecule preferably is specific for one or more pathogen(s), such a coronavirus, for example SARS-CoV2. According to preferred embodiments, such biomolecules are detected by one or more methods for analysis of biomolecules selected from the group comprising nucleic acid amplification methods such as PCR, qPCR, RT-PCR, qRT-PCR or isothermal amplification, mass spectrometry, detection of enzymatic activity and immunoassay based detection methods. Further methods of molecular analysis are known to the person skilled in the art and are comprised by the method of the present invention.

In the context of the methods of the invention can be performed in combination with mass spectrometry to detect pathogens as for example disclosed in U.S. Pat. No. 9,074, 236.

Furthermore, in embodiments the methods of the invention can be performed in combination with further diagnostic procedures, such as x-ray analysis, ultrasound examination, CT scanning or other diagnostic imaging techniques.

In one embodiment of the method described herein a first antibody and a second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to said proADM or fragments thereof to be detected, a measurable signal which permits detection of the resulting sandwich complexes in the measuring solution is generated.

In one embodiment of the method described herein the labelling system comprises a rare earth cryptate or chelate in combination with a fluorescent or chemiluminescent dye, in particular of the cyanine type.

In one embodiment of the method described herein, the method additionally comprises comparing the determined level of proADM or fragment(s) thereof to a reference level, threshold value and/or a population average corresponding to proADM or fragments thereof in patients who have been diagnosed as being critically ill and are under medical treatment, wherein said comparing is carried out in a computer processor using computer executable code.

The methods of the present invention may in part be computer-implemented. For example, the step of comparing the detected level of a marker, e.g. the proADM or fragments thereof, with a reference level can be performed in a computer system. In the computer-system, the determined level of the marker(s) can be combined with other marker levels and/or parameters of the subject in order to calculate a score, which is indicative for the diagnosis, prognosis, prediction, risk assessment and/or risk stratification. For example, the determined values may be entered (either manually by a health professional or automatically from the device(s) in which the respective marker level(s) has/have been determined) into the computer-system. The computer-system can be directly at the point-of-care (e.g. primary care, ICU or ED) or it can be at a remote location connected via a computer network (e.g. via the internet, or specialized medical cloud-systems, optionally combinable with other IT-systems or platforms such as hospital information systems (HIS)). Typically, the computer-system will store the values (e.g. marker level or parameters such as age, blood pressure, weight, sex, etc. or clinical scoring systems such as SOFA, qSOFA, BMI etc.) on a computer-readable medium and calculate the score based-on pre-defined and/or pre-stored reference levels or reference values. The resulting score will be displayed and/or printed for the user (typically a health professional such as a physician). Alternatively or in addition, the associated prognosis, diagnosis, assessment, treatment guidance, patient management guidance or stratification will be displayed and/or printed for the user (typically a health professional such as a physician).

In embodiments, a low risk patient that has been diagnosed with SARS can be admitted to remote patient management. For example, a low risk patient that has been diagnosed with SARS may remain an outpatient, or may be discharged from an ICU or to become an outpatient with access to remote patient management.

In one embodiment of the invention, a software system can be employed, in which a machine learning algorithm is evident, preferably to identify hospitalized patients at risk for sepsis, severe sepsis and septic shock using data from electronic health records (EHRs). A machine learning approach can be trained on a random forest classifier using EHR data (such as labs, biomarker expression, vitals, and demographics) from patients. Machine learning is a type of artificial intelligence that provides computers with the ability to learn complex patterns in data without being explicitly programmed, unlike simpler rule-based systems. Earlier studies have used electronic health record data to trigger alerts to detect clinical deterioration in general. In one embodiment of the invention the processing of proADM levels may be incorporated into appropriate software for comparison to existing data sets, for example proADM levels may also be processed in machine learning software to assist in diagnosing or prognosing the occurrence of an adverse event.

The combined employment of proADM or fragments thereof in combination with another biomarker such as PCT or CRP may be realized either in a single multiplex assay, or in two separate assays conducted on a sample form the patient. The sample may relate to the same sample, or to different samples. The assay employed for the detection and determination of proADM and for example PCT may also be the same or different, for example an immunoassay may be employed for the determination of one of the above markers. More detailed descriptions of suitable assays are provided below.

Cut-off values and other reference levels of proADM or fragments thereof in patients who have been diagnosed as being critically ill and are under treatment may be determined by previously described methods. For example, methods are known to a skilled person for using the Coefficient of variation in assessing variability of quantitative assays in order to establish reference values and/or cut-offs (George F. Reed et al., Clin Diagn Lab Immunol. 2002; 9(6):1235-1239).

Additionally, functional assay sensitivity can be determined in order to indicate statistically significant values for use as reference levels or cut-offs according to established techniques. Laboratories are capable of independently establishing an assay's functional sensitivity by a clinically relevant protocol. "Functional sensitivity" can be considered as the concentration that results in a coefficient of variation (CV) of 20% (or some other predetermined % CV), and is thus a measure of an assay's precision at low analyte levels. The CV is therefore a standardization of the standard deviation (SD) that allows comparison of variability estimates regardless of the magnitude of analyte concentration, at least throughout most of the working range of the assay.

Furthermore, methods based on ROC analysis can be used to determine statistically significant differences between two clinical patient groups. Receiver Operating Characteristic (ROC) curves measure the sorting efficiency of the model's fitted probabilities to sort the response levels. ROC curves can also aid in setting criterion points in diagnostic tests. The higher the curve from the diagonal, the better the fit. If the logistic fit has more than two response levels, it produces a generalized ROC curve. In such a plot, there is a curve for each response level, which is the ROC curve of that level versus all other levels. Software capable of enabling this kind of analysis in order to establish suitable reference levels and cut-offs is available, for example JMP 12, JMP 13, Statistical Discovery, from SAS.

Cut off values may similarly be determined for PCT. Literature is available to a skilled person for determining an appropriate cut-off, for example Philipp Schuetz et al. (BMC Medicine. 2011; 9:107) describe that at a cut-off of 0.1 ng/mL, PCT had a very high sensitivity to exclude infection. Terence Chan et al. (Expert Rev.Mol.Diagn. 2011; 11(5), 487.496) described that indicators such as the positive and negative likelihood ratios, which are calculated based on sensitivity and specificity, are also useful for assessing the strength of a diagnostic test. Values are commonly graphed for multiple cut-off values (CVs) as a receiver operating characteristic curve. The area under the curve value is used to determine the best diagnostically relevant CV. This literature describes the variation of CVs (cut-off values, that is dependent on the assay and study design), and suitable methods for determining cut-off values.

Population averages levels of proADM or fragments thereof may also be used as reference values, for example mean proADM population values, whereby patients that are diagnosed as critically ill may be compared to a control population, wherein the control group preferably comprises more than 10, 20, 30, 40, 50 or more subjects.

In one embodiment of the invention, the cut-off level for PCT may be a value in the range of 0.01 to 100.00 ng/mL in a serum sample, when using for example a Luminex MAC Pix E-Bioscience Assay or the BRAHMS PCT-Kryptor Assay. In a preferred embodiment the cut-off level of PCT may be in the range of 0.01 to 100, 0.05 to 50, 0.1 to 20, or 0.1 to 2 ng/mL, and most preferably >0.05 to 0.5 ng/mL. Any value within these ranges may be considered as an appropriate cut-off value. For example, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 6, 7, 8, 9, 10, 15, 20, 25, 30, 35, 40, 45, 50, 55, 60, 65, 70, 75, 80, 85, 90, 95 or 100 ng/mL may be employed. In some embodiments, PCT levels for healthy subjects are approximately 0.05 ng/mL.

DETAILED DESCRIPTION OF THE INVENTION

The present invention is based on the surprising finding that proADM enables effective prognostic statements regarding whether intensifying treatment and/or disease monitoring and/or hospitalization is required for patients with symptoms of SARS or of infection with a SARS-virus, thereby providing effective means for therapy guidance. In particular, the invention enables risk assessment for patients suspected of having a coronavirus infection, such as a SARS-coronavirus, for example SARS-CoV2.

As used herein, the "patient" or "subject" may be a vertebrate. In the context of the present invention, the term "subject" includes both humans and animals, particularly mammals, and other organisms.

As used herein, a "patient with symptoms of an infectious disease" is a subject who presents with one or more of, without limitation, fever, diarrhea, fatigue, muscle aches, coughing, if have been bitten by an animal, having trouble breathing, severe headache with fever, rash or swelling, unexplained or prolonged fever or vision problems. Other symptoms may be fever and chills, very low body temperature, decreased output of urine (oliguria), rapid pulse, rapid breathing, nausea and vomiting. In preferred embodiments the symptoms of an infectious disease are fever, diarrhea, fatigue, muscle aches, rapid pulse, rapid breathing, nausea and vomiting and/or coughing.

As used herein "infectious disease" comprises all diseases or disorders that are associated with bacterial and/or viral and/or fungal infections.

As used herein, a patient with "symptoms of a viral infection of the respiratory tract" is a subject who presents with one or more of, without limitation, cold-like symptoms or flu-like illnesses, such as fever, cough, runny nose, sneezing, sore throat, having trouble breathing, headache, muscle aches, fatigue, rapid pulse, rapid breathing, nausea and vomiting, lack of taste and/or smell and/or malaise (feeling unwell).

In some embodiments, symptoms of infection with a SARS-virus are fever, sore throat, cough, myalgia or fatigue, and in some embodiments, additionally, sputum production, headache, hemoptysis and/or diarrhea.

In some embodiments, symptoms of a infection with a SARS-coronavirus, for example SARS-CoV-2, are fever, sore throat, cough, lack of taste and/or smell, shortness of breath and/or fatigue.

As used herein, the term "a patient that is at risk of developing a severe acute respiratory syndrome (SARS)" relates to a subject, preferably distinct from any given person in the general population, who has an increased (e.g. above-average) risk of developing SARS. In some embodiments, the patient has symptoms of SARS or symptoms of a SARS-virus infection. In some embodiments, the patient has no symptoms of SARS or symptoms of a SARS-virus infection. In some embodiments, the subject has been in contact with people with SARS-virus infections or symptoms. In some embodiments, the person at risk of developing SARS has been tested for the presence of a SARS-virus infection. In some embodiments, the person at risk of developing SARS has tested positive for the presence of a SARS-virus infection, preferably a coronavirus infection.

In embodiments, the patient at risk of developing SARS is an asymptomatic patient that shows no specific symptoms of SARS (yet). An asymptomatic patient may be at risk of developing SARS because the patient has been in contact with a person infected with a SARS-virus. For example, the asymptomatic patient may have been identified as being at risk of developing SARS by a software application (app) that is installed on his smart phone or corresponding (portable) device and that indicates physical proximity or short physical distance to an infected patient that uses a corresponding app on its respective mobile device/smart phone. Other methods of determining contact/physical proximity to an infected person are known to the skilled person and equally apply to the method of the invention.

In some embodiments, the patient that has or is at risk of developing a severe acute respiratory syndrome (SARS) has a coronavirus infection.

Coronaviruses are a group of related viruses that cause diseases in mammals and birds. The scientific name for coronavirus is Orthocoronavirinae or Coronavirinae. Coronavirus belongs to the family of Coronaviridae. The family is divided into Coronavirinae and Torovirinae sub-families, which are further divided into six genera: *Alphacoronavirus, Betacoronavirus, Gammacoronavirus, Deltacoronavirus, Torovirus*, and *Bafinivirus*. While viruses in the genera Alphacoronaviruses and Betacoronaviruses infect mostly mammals, the *Gammacoronavirus* infect avian species and members of the *Deltacoronavirus* genus have been found in both mammalian and avian hosts.

In humans, coronaviruses cause respiratory tract infections that can be mild, such as some cases of the common cold, and others that can be lethal, such as SARS, MERS, and COVID-19. Coronaviruses are enveloped viruses with a positive-sense single-stranded RNA genome and a nucleocapsid of helical symmetry. The genome size of coronaviruses ranges from approximately 27 to 34 kilobases, the largest among known RNA viruses.

Various species of human coronaviruses are known, such as, without limitation, Human coronavirus OC43 (HCoV-OC43), of the genus β-CoV, Human coronavirus HKU1 (HCoV-HKU1), of the genus β-CoV, Human coronavirus 229E (HCoV-229E), α-CoV, Human coronavirus NL63 (HCoV-NL63), α-CoV. Middle East respiratory syndrome-related coronavirus (MERS-CoV), Severe acute respiratory syndrome coronavirus (SARS-CoV), Severe acute respiratory syndrome coronavirus 2 (SARS-CoV-2).

Coronaviruses vary significantly in risk factor. Some can kill more than 30% of those infected (such as MERS-CoV), and some are relatively harmless, such as the common cold. Coronaviruses cause colds with major symptoms, such as fever, and a sore throat, e.g. from swollen adenoids, occurring primarily in the winter and early spring seasons. Coronaviruses can cause pneumonia (either direct viral pneumonia or secondary bacterial pneumonia) and bronchitis (either direct viral bronchitis or secondary bacterial bronchitis). Coronaviruses can also cause SARS.

Advances in nucleic acid sequencing technology (commonly termed Next-Generation Sequencing, NGS) are providing large sets of sequence data obtained from a variety of biological samples and allowing the characterization of both known and novel virus strains. Established methods are therefore available for determining a Coronavirus infection.

Viruses encode a collection of proteins required to ensure self-replication and persistence of the encoding virus. Enzymes for genome mRNA production and genome replication, proteases for protein maturation, proteins for genome encapsidation, and proteins for undermining the host antiviral responses can be identified conserved protein motifs or domains. Likely because of selective pressures, viral genomes are streamlined and the functional protein content encoded by viruses is much higher than for a cellular organisms. Thus, describing a viral genome by the collection of encoded protein domains is a potentially useful classification method. Viral evolution can therefore be followed and novel strains of coronavirus can be determined based on sequence comparison to known coronavirus strains.

In some embodiments, the patient suffers from an infection, preferably with a SARS-virus, more preferably a SARS-coronavirus (SARS-CoV).

As used herein, SARS-virus refers to a virus that leads to severe acute respiratory syndrome (SARS). Although Coronaviruses have to date been primarily responsible for SARS, other viral infections may lead to SARS, for example other viruses of zoonotic origin.

As used herein, SARS-coronavirus refers to a Coronavirus that leads to severe acute respiratory syndrome (SARS). This syndrome is a viral respiratory disease of zoonotic origin that first surfaced in the early 2000s caused by the first-identified strain of the SARS coronavirus (SARS-CoV or SARS-CoV-1).

SARS is induced via droplet transmission and replication of the virus could be shown in the upper and lower respiratory tract or gastrointestinal mucosa. In parallel the virus is also capable of directly invading cells of different organs such as liver, kidney, heart and brain. Another distinct mechanism appears to be the direct invasion of the virus in T-cells. A significant number of SARS patients, who suffer COVID-19, have a clinically low concentration of lymphocytes in the blood, also known as Lymphocytopenia Clinically, patients show respiratory symptoms such as dry cough and shortness of breath, fever or diarrhea. But symptoms associated with acute liver injury, heart injury or kidney injury can also occur. In a less severe state of SARS, patients can show mild or even no symptoms.

Clinical and scientific investigations propose that SARS-CoVs bind to the epithelial cells via the Angiotensin converting enzyme 2 receptor (ACE2). ACE2 is a cell membrane linked aminopeptidase which is expressed in vascular endothelia, kidney, bladder, heart, nasal mucosa, bronchus and lung. As one consequence binding of the virus leads to an epithelial and endothelial cell damage along with vascular leakage, which triggers a secretion of pro-inflammatory cytokines and chemokines. The virus also mediates ACE2 downregulation and shedding which further promotes a dysfunctional renin-angiotensin system (RAS). Once the RAS is disturbed it can lead an inflammatory response and to vascular permeability. Focusing on the respiratory system, ACE2 shedding can lead to pulmonary vascular permeability and subsequently to pulmonary edema.

Another pathophysiological element which is called antibody dependent enhancement (ADE) is associated with the existence of antibodies that bind to viruses and facilitate the entry of the virus into the cell. Thereby those antibodies support the virus replication and spread of the virus in the body instead of showing a neutralizing effect. If ADE is present in a patient, a systemic inflammatory response can be activated or maintained.

It is proposed that direct cell damage (multiorgan) and an impaired RAS are key factors for a local and systematic inflammatory response resulting in a so called cytokine storm which is related to an adverse outcome of SARS patients. Adverse outcomes of SARS can be based on the development of an Acute Respiratory Distress Syndrome (ARDS), multiorgan damage or Lymphocytopenia.

Older patients (above 60 years), patients with chronic diseases (e.g. cardiovascular diseases, diabetes, cancer, COPD) or immunocompromised patients are considered to be at a higher risk to face a severe development of SARS. Smoking and obesity are also considered as risk factors (1-5, 21).

Embodiments of a SARS-coronavirus include, without limitation, any coronavirus that induces a SARS or SARS-similar pathology. Particular embodiments include, without limitation, the SARS-Coronavirus (SARS-CoV-1) first discovered in 2003 (as described above), the Middle East respiratory syndrome (MERS-CoV) first discovered in 2012, and the SARS-CoV-2, which causes COVID-19, a disease which brought about the 2019-2020 coronavirus pandemic.

In preferred embodiments, the SARS-coronavirus is SARS-CoV-2.

The strain SARS-CoV-2 causes COVID-19, a disease which brought about the ongoing 2019-2020 coronavirus pandemic. The disease was first identified in December 2019 in Wuhan, the capital of China's Hubei province, and spread globally. Common symptoms include fever, cough, and shortness of breath. Other symptoms may include muscle pain, diarrhea, sore throat, loss of taste and/or smell, and abdominal pain. While the majority of cases result in mild symptoms, some progress to viral pneumonia and multiorgan failure.

Coronaviruses can be determined by molecular techniques, for example sequence-based analysis, for example by PCR-based amplification of viral genetic material. Genome-wide phylogenetic analysis indicates that SARS-CoV-2 shares 79.5% and 50% sequence identity to SARS-CoV and MERS-CoV, respectively. However, there is 94.6% sequence identity between the seven conserved replicase domains in ORF1ab of SARS-CoV-2 and SARS-CoV, and less than 90% sequence identity between those of SARS-CoV-2 and other -CoVs, implying that SARS-CoV-2 belongs to the lineage of Beta-CoVs.

Similar to other -CoVs, the SARS-CoV-2 virion with a genome size of 29.9 kb [13] possesses a nucleocapsid composed of genomic RNA and phosphorylated nucleocapsid (N) protein. The nucleocapsid is buried inside phospholipid bilayers and covered by two different types of spike proteins: the spike glycoprotein trimmer (S) that exists in all CoVs, and the hemagglutinin-esterase (HE) only shared among some CoVs. The membrane (M) protein and the envelope (E) protein are located among the S proteins in the viral envelope. The SARS-CoV-2 genome has 5' and 3' terminal sequences (265 nt at the 5' terminal and 229 nt at the 3' terminal region), which is typical of -CoVs, with a gene order 5'-replicase open reading frame (ORF) 1ab-S-envelope(E)-membrane (M)-N-30. The predicted S, ORF3a, E, M, and N genes of SARS-CoV-2 are 3822, 828, 228, 669, and 1260 nt in length, respectively. Similar to SARS-CoV, SARS-CoV-2 carries a predicted ORF8 gene (366 nt in length) located between the M and N ORF genes.

According to Jin et al (Viruses 2020, 12, 372), in the initial 41 patients, fever (98%), cough (76%), and myalgia or fatigue (44%) were the most common symptoms. Less common symptoms were sputum production (28%), headache (8%), hemoptysis (5%), and diarrhea (3%). More than half of patients developed dyspnea. The average incubation period and basic reproduction number (R0) were estimated to be 5.2 d (95% CI: 4.1-7.0) and 2.2 (95% CI, 1.4-3.9), respectively. Blood test showed normal or reduced (25%) white blood cell count and lymphopenia (65%). A total of 98% of patients had bilateral involvement under chest CT. Typical findings of chest CT images of ICU patients on admission were bilateral multiple lobular and subsegmental areas of consolidation. The representative chest CT findings of non-ICU patients showed bilateral ground-glass opacity and subsegmental areas of consolidation. Analysis of 1324 laboratory confirmed cases showed that fever (87.9%) and cough (67.7%) were still the most common symptoms, while diarrhea is uncommon. Lymphopenia was observed in 82.1% of patients admitted to ICU.

In some embodiments, subjects have been tested and determined to have a SARS-Cov. Various methods may be employed to detect SAR-CoV, e.g. SARS-CoV-2, such as a nucleic acid test, serologic diagnosis, CRISPR/Cas13-based SHERLOCK technology, or imaging technology, such as chest radiographs or CT-scans.

As used herein, the term "influenza virus" is a virus that leads to Influenza, commonly known as "the flu". In virus classification, influenza viruses are RNA viruses that make up four of the seven genera of the family Orthomyxoviridae: *Influenzavirus* A, *Influenzavirus* B, *Influenzavirus* C, *Influenzavirus* D. These viruses are distantly related to the human parainfluenza viruses, which are RNA viruses belonging to the paramyxovirus family that are a common cause of respiratory infections in children such as croup, but can also cause a disease similar to influenza in adults. Influenzaviruses A, B, C, and D are very similar in overall structure. The virus particle (also called the virion) is 80-120 nanometers in diameter such that the smallest virions adopt an elliptical shape. The central core contains the viral RNA genome and other viral proteins that package and protect this RNA.

As used herein, "patients with an increased risk of an adverse event" are preferably selected from those disclosed explicitly above. Any given patient can be assessed, and usually based on the presence of an additional disease or immunological deficiency, can be categorized as a patient with an increased risk of an adverse event.

In some embodiments, "patients with an increased risk of an adverse event" are selected from hypertension, cardiovascular diseases, diabetes mellitus, smoking, chronic obstructive pulmonary disease (COPD), malignancy, and chronic kidney disease, preferably selected from the group of hypertension, cardiovascular disease, smoking history and diabetes. According to Emami et al (Arch Acad Emerg Med. 2020 Mar. 24; 8(1):e35), the data of 76993 patients presented in 10 articles were assessed for the prevalence of underlying disease in hospitalized patients with COVID-19. According to the analysis, the pooled prevalence of hypertension, cardiovascular disease, smoking history and diabetes in people infected with SARS-CoV-2 were estimated as 16.37% (95% CI: 10.15%-23.65%), 12.11% (95% CI 4.40%-22.75%), 7.63% (95% CI 3.83%-12.43%) and 7.87% (95% CI 6.57%-9.28%), respectively. Due to the high prevalence of patients with these conditions being hospitalized, this is an indication of an adverse event in case of a viral infection.

The present invention therefore enables a risk assessment of disease progression of SARS or of infection with a SARS-virus, such as a SARS-virus infection of the respiratory tract, such as COVID-19. The following description of COVID-19 pathogenesis is therefore by way of example, and can be referred to, assessed and employed by skilled persons in the medical field for other SARS-CoV.

SARS-CoV-2 is transmitted predominantly via respiratory droplet, contact, and potential in fecal-oral. Primary viral replication is presumed to occur in mucosal epithelium of upper respiratory tract (nasal cavity and pharynx), with further multiplication in lower respiratory tract and gastro-intestinal mucosa, giving rise to a mild viremia. Few infections are controlled at this point and remain asymptomatic. Some patients have also exhibited non-respiratory symptoms such as acute liver and heart injury, kidney failure, diarrhea, implying multiple organ involvement. ACE2 is broadly expressed in nasal mucosa, bronchus, lung, heart, esophagus, kidney, stomach, bladder, and ileum, and these human organs are all vulnerable to SARS-CoV-2.

According to Jin et al (Viruses 2020, 12, 372), the first report of pathological findings from severe COVID-19 showed pulmonary bilateral diffuse alveolar damage with cellular fibromyxoid exudates. The right lung showed evident desquamation of pneumocytes and hyaline membrane formation, indicating acute respiratory distress syndrome. The left lung tissue displayed pulmonary edema with hyaline membrane formation, suggestive of early-phase acute respiratory distress syndrome (ARDS). Interstitial mononuclear inflammatory infiltrates, dominated by lymphocytes, could be observed in both lungs. Multinucleated syncytial cells with atypical enlarged pneumocytes characterized by large nuclei, amphiphilic granular cytoplasm, and prominent nucleoli were identified in the intra-alveolar spaces, indicating viral cytopathic-like changes.

According to Jin et al (Viruses 2020, 12, 372), these pulmonary pathological findings extremely resemble those seen in SARS and MERS. Moderate microvascular steatosis and mild lobular and portal activity were observed in liver biopsy specimens, which might be caused by either SARS-CoV-2 infection or drug use. In addition, only a few interstitial mononuclear inflammatory infiltrates were found in the heart tissue, which means that SARS-CoV-2 might not directly impair the heart. Massive mucus secretion in both lungs was found in death cases with COVID-19, which was different from SARS and MERS. Acute Respiratory Distress Syndrome (ARDS) is a life-threatening lung condition that prevents enough oxygen from getting to the lungs and into the circulation, accounting for mortality of most respiratory disorders and acute lung injury. In fatal cases of human SARS-CoV, MERS-CoV, and SARS-CoV-2 infections, individuals exhibit severe respiratory distress requiring mechanical ventilation, and the histopathology findings also support ARDS. Immune dysfunction and cytokine storms were also seen in COVID-19 induced fatalities.

As used herein, the term "requires intensifying treatment and/or disease monitoring" therefore refers to a patient with a higher risk of the disease worsening, i.e. a higher risk of progressing to a more severe health-risk to the patient compared to a patient with a low risk, considered preferably in relation to the description of pathogenesis described above.

As used herein, the term "at risk of a disease progression to a condition that requires hospitalization" relates to patients that require intensifying treatment and/or disease monitoring, whereby the treatment options available at a hospital are advisable on recommendation of medical staff. In other words, the risk is assessed as such, that the treatments typically available outside of hospital are insufficient to safely care for the patient and avoid unwanted adverse events.

As used herein, the term "at risk of a disease progression to a condition that requires treatment and/or disease monitoring on an ICU" relates to patients that require intensifying treatment and/or disease monitoring, whereby the treatment options available at the ICU are advisable on recommendation of medical staff. In other words, the risk is assessed as such, that the treatments typically available outside of the ICU are insufficient to safely care for the patient and avoid unwanted adverse events.

The treatment options typically available outside a hospital, in a hospital and in an ICU are known to a skilled person, and are by way of example also disclosed herein.

According to the invention, therapeutic interventions or therapeutics can also comprise Type 1 Interferons (IFN), IFN-α, IFN-β, immunosuppressive drugs, Ribavirn, Remdesivir, Lopinavir, Nelfinavir, Chloroquine, convalescent plasma, anti-SARS CoV antibodies, anti-Fc specific antibodies, renin-angiotensin system (RAS) inhibitors, intravenous transplantation of ACE2-mesenchymal stem cells (MSCs), anti-inflammatory drugs, Tumor necrosis factor-α blocker, proteinase inhibitors, steroids, vaccination, The patient described herein who has been diagnosed as being "critically ill" can be diagnosed as an intensive care unit (ICU) patient, a patient who requires constant and/or intense observation of his health state, a patient diagnosed with SARS, with SARS and sepsis, severe sepsis or septic shock, a patient diagnosed with an SARS and one or more existing organ failure(s), a pre- or post-surgical patient, an intraoperative patient, a posttraumatic patient, a trauma patient, such as an accident patient, a burn patient, a patient with one or more open lesions. The subject described herein can be at the emergency department or intensive care unit, or in other point of care settings, such as in an emergency transporter, such as an ambulance, or at a general practitioner, who is confronted with a patient with said symptoms.

As used herein, "diagnosis" in the context of the present invention relates to the recognition and (early) detection of a clinical condition. Also the assessment of the severity may be encompassed by the term "diagnosis".

"Prognosis" relates to the prediction of an outcome or a specific risk for a subject. This may also include an estimation of the chance of recovery or the chance of an adverse outcome for said subject.

The methods of the invention may also be used for monitoring, therapy monitoring, therapy guidance and/or therapy control. "Monitoring" relates to keeping track of a patient and potentially occurring complications, e.g. to analyze the progression of the healing process or the influence of a particular treatment or therapy on the health state of the patient.

The term "therapy monitoring" or "therapy control" in the context of the present invention refers to the monitoring and/or adjustment of a therapeutic treatment of said patient, for example by obtaining feedback on the efficacy of the therapy. As used herein, the term "therapy guidance" refers to application of certain therapies, therapeutic actions or medical interventions based on the value/level of one or more biomarkers and/or clinical parameter and/or clinical scores. This includes the adjustment of a therapy or the discontinuation of a therapy.

In the present invention, the terms "risk assessment" and "risk stratification" relate to the grouping of subjects into different risk groups according to their further prognosis. Risk assessment also relates to stratification for applying preventive and/or therapeutic measures. The term "therapy stratification" in particular relates to grouping or classifying patients into different groups, such as risk groups or therapy groups that receive certain differential therapeutic measures depending on their classification. The term "therapy stratification" also relates to grouping or classifying patients with infections or having symptoms of an infectious disease into a group that are not in need to receive certain therapeutic measures.

As used herein the term "remote patient management" preferably refers to a therapeutic approach for remotely managing patients with a infectious disease, in which data on the health status of a patient is repeatedly collected at the site of the patient (i.e. out-patients) and transmitted to remote (geographically separated) medical personnel or an automated system, which may or may not act upon said data to contact the patient, give advice to the patient, initiate or change concomitant treatments or take any other medical intervention for ameliorating and/or stabilizing the health state of the patient.

A remote patient management preferably encompasses a telemonitoring on health status of the patient as well as telemedical interventions, guideline-based ambulatory care and/or structured patient education.

Telemonitoring preferably refers to the repeated data collection at the site of the patient and its remote transmission to a monitoring system or device allowing for review by medical personnel or an automated medical system.

As used herein the term "remote patient management" preferably refers to a therapeutic approach for remotely managing patients with a infectious disease, in which data on the health status of a patient is repeatedly collected at the site of the patient (i.e. out-patients) and transmitted to remote (geographically separated) medical personnel or an automated system, which may or may not act upon said data to contact the patient, give advice to the patient, initiate or change concomitant treatments or take any other medical intervention for ameliorating and/or stabilizing the health state of the patient.

A remote patient management preferably encompasses a telemonitoring on health status of the patient as well as telemedical interventions, guideline-based ambulatory care and/or structured patient education.

Telemonitoring preferably refers to the repeated data collection at the site of the patient and its remote transmission to a monitoring system or device allowing for review by medical personnel or an automated medical system.

It is understood that in the context of the present invention "determining the level of proADM or fragment(s) thereof" or the like refers to any means of determining proADM or a fragment thereof.

The fragment can have any length, e.g. at least about 5, 10, 20, 30, 40, 50 or 100 amino acids, so long as the fragment allows the unambiguous determination of the level of proADM or fragment thereof. In particular preferred aspects of the invention, "determining the level of proADM"

refers to determining the level of midregional proadrenomedullin (MR-proADM). MR-proADM is a fragment and/or region of proADM.

The peptide adrenomedullin (ADM) was discovered as a hypotensive peptide comprising 52 amino acids, which had been isolated from a human phenochromocytome (Kitamura et al., 1993). Adrenomedullin (ADM) is encoded as a precursor peptide comprising 185 amino acids ("preproadrenomedullin" or "pre proADM"). An exemplary amino acid sequence of ADM is given in SEQ ID NO: 1.

SEQ ID NO:1: Amino Acid Sequence of Pre-Pro-ADM:

```
  1  MKLVSVALMY  LGSLAFLGAD  TARLDVASEF
     RKKWNKWALS  RGKRELRMSS
 51  SYPTGLADVK  AGPAQTLIRP  QDMKGASRSP
     EDSSPDAARI  RVKRYRQSMN
101  NFQGLRSFGC  RFGTCTVQKL  AHQIYQFTDK
     DKDNVAPRSK  ISPQGYGRRR
151  RRSLPEAGPG  RTLVSSKPQA  HGAPAPPSGS
     APHFL
```

ADM comprises the positions 95-146 of the pre-proADM amino acid sequence and is a splice product thereof. "Proadrenomedullin" ("proADM") refers to pre-proADM without the signal sequence (amino acids 1 to 21), i.e. to amino acid residues 22 to 185 of pre-proADM. "Midregional proadrenomedullin" ("MR-proADM") refers to the amino acids 42 to 95 of pre-proADM. An exemplary amino acid sequence of MR-proADM is given in SEQ ID NO: 2.

SEQ ID NO:2: Amino Acid Sequence of MR-Pro-ADM (AS 45-92 of Pre-Pro-ADM):

```
ELRMSSSYPT GLADVKAGPA QTLIRPQDMK

GASRSPEDSS PDAARIRV
```

It is also envisaged herein that a peptide and fragment thereof of pre-proADM or MR-proADM can be used for the herein described methods. For example, the peptide or the fragment thereof can comprise the amino acids 22-41 of pre-proADM (PAMP peptide) or amino acids 95-146 of pre-proADM (mature adrenomedullin, including the biologically active form, also known as bio-ADM).

SEQ ID NO:3: Amino Acid Sequence of Mature ADM (AS 95-146 of Pre-Pro-ADM):

```
YRQSMNNFQGLRSFGCRFGTCTVQKLAHQIYQ

FTDKDKDNVAPRSAISPQGY
```

A C-terminal fragment of proADM (amino acids 153 to 185 of pre proADM) is called adrenotensin. Fragments of the proADM peptides or fragments of the MR-proADM can comprise, for example, at least about 5, 10, 20, 30 or more amino acids. Accordingly, the fragment of proADM may, for example, be selected from the group consisting of MR-proADM, PAMP, adrenotensin and mature adrenomedullin, preferably herein the fragment is MR-proADM.

The determination of these various forms of ADM or proADM and fragments thereof also encompass measuring and/or detecting specific sub-regions of these molecules, for example by employing antibodies or other affinity reagents directed against a particular portion of the molecules, or by determining the presence and/or quantity of the molecules by measuring a portion of the protein using mass spectrometry. Any one or more of the "ADM peptides or fragments" described herein may be employed in the present invention.

Accordingly, the methods and kits of the present invention can also comprise determining at least one further biomarker, marker, clinical score and/or parameter in addition to ADM.

As used herein, a parameter is a characteristic, feature, or measurable factor that can help in defining a particular system. A parameter is an important element for health- and physiology-related assessments, such as a disease/disorder/clinical condition risk, preferably organ dysfunction(s). Furthermore, a parameter is defined as a characteristic that is objectively measured and evaluated as an indicator of normal biological processes, pathogenic processes, or pharmacologic responses to a therapeutic intervention. An exemplary parameter can be selected from the group consisting of Pneumonia Severity Index (PSI), Acute Physiology and Chronic Health Evaluation II (APACHE II), the simplified acute physiology score (SAPSII score), sequential organ failure assessment score (SOFA score), quick sequential organ failure assessment score (qSOFA), body mass index, weight, age, sex, IGS II, liquid intake, white blood cell count, sodium, potassium, temperature, blood pressure, dopamine, bilirubin, respiratory rate, partial pressure of oxygen, World Federation of Neurosurgical Societies (WFNS) grading, Glasgow Coma Scale (GCS), CURB-65 pneumonia severity score, Pneumonia Severity Index (PSI), age, gender, family history, ethnicity, body weight, body mass index (BMI), cystoscopy report, white blood cell count, lymphocyte count, imaging methods as such as CT scan, PET imaging or X-ray, blood pressure, heart rate, antihypertensive treatment, liquid intake, wheezing, body temperature, presence of diabetes mellitus, blood glucose levels, and (current) smoking habits.

Such parameters may additionally be assessed in combination with the methods described herein in order to improve assay implementation and diagnostic statements.

The present invention has the following advantages over the conventional methods: the inventive methods and the kits are fast, objective, easy to use and precise. The methods and kits of the invention relate to markers and clinical scores that are easily measurable in routine methods, because the levels of proADM, PCT, D-Dimer, Troponin, Copeptin, lactate, c-reactive protein, can be determined in routinely obtained blood samples or further biological fluids or samples obtained from a subject.

As used herein, terms such as "marker", "surrogate", "prognostic marker", "factor" or "biomarker" or "biological marker" are used interchangeably and relate to measurable and quantifiable biological markers (e.g., specific protein or enzyme concentration or a fragment thereof, specific hormone concentration or a fragment thereof, or presence of biological substances or a fragment thereof) which serve as indices for health- and physiology-related assessments, such as a disease/disorder/clinical condition risk, preferably an adverse event. A marker or biomarker is defined as a characteristic that can be objectively measured and evaluated as an indicator of normal biological processes, pathogenic processes, or pharmacologic responses to a therapeutic intervention. Biomarkers may be measured in a sample (as a blood, plasma, urine, or tissue test).

The at least one further marker and/or parameter of said subject can be selected from the group consisting of a level of lactate in said sample, a level of procalcitonin (PCT) in said sample, the sequential organ failure assessment score (SOFA score) of said subject, optionally the quick SOFA score, the simplified acute physiology score (SAPSII) of said subject, the Acute Physiology and Chronic Health Evaluation II (APACHE II) score of said subject and a level of the soluble fms-like tyrosine kinase-1 (sFlt-1), Histone H2A, Histone H2B, Histone H3, Histone H4, calcitonin, Endothelin-1 (ET-1), Arginine Vasopressin (AVP), Atrial Natriuretic Peptide (ANP), Neutrophil Gelatinase-Associated Lipocalin (NGAL), Troponin, Brain Natriuretic Peptide (BNP), C-Reactive Protein (CRP), Pancreatic Stone Protein (PSP), Triggering Receptor Expressed on Myeloid Cells 1 (TREM1), Interleukin-8 (IL-6), Interleukin-1, Interleukin-24 (IL-24), Interleukin-22 (IL-22), Interleukin (IL-20) other ILs, Presepsin (sCD14-ST), Lipopolysaccharide Binding Protein (LBP), Alpha-1-Antitrypsin, Matrix Metalloproteinase 2 (MMP2), Metalloproteinase 2 (MMP8), Matrix Metalloproteinase 9 (MMP9), Matrix Metalloproteinase 7 (MMP7, Placental growth factor (PIGF), Chromogranin A, S100A protein, S100B protein and Tumor Necrosis Factor α (TNFα), Neopterin, Alpha-1-Antitrypsin, pro-arginine vasopressin (AVP, proAVP or Copeptin), procalcitonin, atrial natriuretic peptide (ANP, pro-ANP), Endothelin-1, CCL1/TCA3, CCL11, CCL12/MCP-5, CCL13/MCP-4, CCL14, CCL15, CCL16, CCL17/TARC, CCL18, CCL19, CCL2/MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CX3CL1, CXCL1, CXCL10, CXCL11, CXCL12, CXCL13, CXCL14, CXCL15, CXCL16, CXCL17, CXCL2/MIP-2. CXCL3, CXCL4, CXCL5, CXCL6, CXCL7/Ppbp, CXCL9, IL8/CXCL8, XCL1, XCL2, FAM19A1, FAM19A2, FAM19A3, FAM19A4, FAM19A5, CLCF1, CNTF, IL11, IL31, IL6, Leptin, LIF, OSM, IFNA1, IFNA10, IFNA13, IFNA14, IFNA2, IFNA4, IFNA7, IFNB1, IFNE, IFNG, IFNZ, IFNA8, IFNA5/IFNaG, IFNω/IFNW1, BAFF, 4-1BBL, TNFSF8, CD40LG, CD70, CD95L/CD178, EDA-A1, TNFSF14, LTA/TNFB, LTB, TNFa, TNFSF10, TNFSF11, TNFSF12, TNFSF13, TNFSF15, TNFSF4, TRAIL, IP-10, IL18, IL18BP, IL1A, IL1B, IL1F10, IL1F3/IL1RA, IL1F5, IL1F6, IL1F7, IL1F8, IL1RL2, IL1F9, IL33 or a fragment thereof. Further markers comprise membrane microparticle, platelet count, mean platelet volume (MPV), sCD14-ST, prothrombinase, antithrombin and/antithrombin activity, cationic protein 18 (CAP18), von Willebrand factor (vWF)-cleaving proteases, lipoproteins in combination with CRP, fibrinogen, fibrin, B2GP1, GPIIb-IIIa, non-denatured D-dimer of fibrin, platelet factor 4, histones and a PT-Assay.

As used herein, "procalcitonin" or "PCT" relates to a peptide spanning amino acid residues 1-116, 2-116, 3-116, or fragments thereof, of the procalcitonin peptide. PCT is a peptide precursor of the hormone calcitonin. Thus the length of procalcitonin fragments is at least 12 amino acids, preferably more than 50 amino acids, more preferably more than 110 amino acids. PCT may comprise post-translational modifications such as glycosylation, liposidation or derivatization. Procalcitonin is a precursor of calcitonin and katacalcin. Thus, under normal conditions the PCT levels in the circulation are very low (<about 0.05 ng/ml).

The level of PCT in the sample of the subject can be determined by immunoassays as described herein. As used herein, the level of ribonucleic acid or deoxyribonucleic acids encoding "procalcitonin" or "PCT" can also be determined. Methods for the determination of PCT are known to a skilled person, for example by using products obtained from Thermo Fisher Scientific/B•R•A•H•M•S GmbH.

Troponin is a protein found in muscles which facilitate contraction by sliding of actin and myosin filaments. It comprises three subunits, C, I and T. An isoform of troponin T, cTnT, is only found in cardiomyocytes and is the most important cardiac biomarker because of its high myocardial specificity and clinical sensitivity. The sequence of the subunit C is given in SEQ ID NO:4. The sequence of the subunit I is given in SEQ ID NO:5. The sequence of the subunit T is given in SEQ ID NO:6.

| SEQ ID NO: 4 | Troponin C | MDDIYKAAVE QLTEEQKNEF KAAFDIFVLG AEDGCISTKE LGKVMRMLGQNPTPEELQEM IDEVDEDGSG TVDFDEFLVM MVRCMKDDSKGKSEEELSDLF RMFDKNADG YIDLDELKIM LQATGETITE DDIEELMKDG DKNNDGRIDYDEFLEFMKGVE |
|---|---|---|
| SEQ ID NO: 5 | Troponin I | MADGSSDAAR EPRPAPAPIR RRSSNYRAYATEPHAKKKSK ISASRKLQLKTLLLQIAKQEL EREAEERRGEKGRALSTRCQP LELAGLGFAELQDLCRQLHAR VDKVDEERYDIEAKVTKNITE IADLTQKIFDLRGKFKRPTLR RVRISADAMMQALLGARAKES LDLRAHLKQVKKEDTEKENRE VGDWRKNIDALSGMEGRKKKF ES |
| SEQ ID NO: 6 | Troponin T | MSDIEEVVEEYEEEEQEEAAV EEQEEAAEEDAEAEAETEETR AEEDEEEEEAKEAEDGPMEES KPKPRIFMPNLVPPKSPDGER VDFDDSHRKRMEKDLNELQAL IEAHFENRKKEEEELVSLKDR IERRRAERAEQQRIRNEREKE RQNRLAEERARREEEENRRKA EDEARKKKALSNMMHFGGYIQ KQAQTERKSGKRQTEREKKKK ILAERRKVLAIDHLNEDQLRE KAKELWQSIYNLEAEKFDLQE KFKQQKYEINVLRNRINDNQK VSKTRGKAKVTGRWK |

"Copeptin" is also referred to as "CT-proAVP" or "C-terminal portion of vasopressin". Vasopressin is a powerful vasoconstrictor. The level of CT-proAVP can be measured in the plasma or serum of a subject by immunoassays as described below.

The sequence of the 164 amino acid precursor peptide of Vasopressin (pre-pro-Vasopressin) is given in SEQ ID NO:7. Pro-Vasopressin relates to the amino acid residues 19 to 164 of the sequence of pre-pro-Vasopressin. The amino acid sequence of pro-Vasopressin is given in SEQ ID NO:8. Pro-Vasopressin is cleaved into mature Vasopressin, Neurophysin II and C-terminal proVasopressin (CT-proAVP or Copeptin). Vasopressin relates to the amino acid residues 20 to 28 of pre-pro-Vasopressin. The amino acid sequence of Vasopressin is shown in SEQ ID NO:9 Coeptin relates to amino acid residues 126 to 164 of pre-pro-Vasopressin. The amino acid sequence of Copeptin is provided in SEQ ID NO:10. Neurophysin II comprises the amino acid residues 32 to 124 of pre-pro-Vasopressin and its sequence is shown in SEQ ID NO:11.

| SEQ ID NO: 7 | Pre-pro-AVP | MPDTMLPACF LGLLAFSSAC YFQNCPRGGK RAMSDLELRQ CLPCGPGGKG RCFGPSICCA DELGCFVGTA EALRCQEENY LPSPCQSGQK ACGSGGRCAA FGVCCNDESC VTEPECREGF HRRARASDRS NATQLDGPAG ALLLRLVQLA GAPEPFEPAQ PDAY |
|---|---|---|

-continued

| SEQ ID NO: 8 | pro-AVP | CYFQNCPRGG KRAMSDLELR QCLPCGPGGK GRCFGPSICC ADELGCFVGT AEALRCQEEN YLPSPCQSGQ KACGSGGRCA AFGVCCNDES CVTEPECREG FHRRARASDR SNATQLDGPA GALLLRLVQL AGAPEPFEPA QPDAY |
|---|---|---|
| SEQ ID NO: 9 | AVP | CYFQNCPRG |
| SEQ ID NO: 10 | Copeptin | ASDRSNATQL DGPAGALLLR LVQLAGAPEP FEPAQPDAY |
| SEQ ID NO: 11 | Neuro-physin II | AMSDLELRQC LPCGPGGKGR CFGPSICCAD ELGCFVGTAE ALRCQEENYL PSPCQSGQKA CGSGGRCAAF GVCCNDESCV TEPECREGFH RRA |

D-Dimer is not normally present in human blood plasma. This biomarker is one of the Fibrinogen degradation products (FDP) which is released after a thrombus or blood clot is enzymatically degraded by Plasmin.

Below a concentration range (e.g. 0.5 mg/l in a blood sample), D-Dimer can help to rule out clinical conditions that are characterized by inappropriate blood clot formation such as deep vein thrombosis, pulmonary embolism or disseminated intravascular coagulation.

In case of increased levels of D-Dimer, further testing (such as ultrasound, scintigraphy. CT scanning) is required (see Adam S S, Key N S, Greenberg C S (March 2009). "D-dimer antigen: current concepts and future prospects". Blood. 113 (13): 2878-87. doi:10.1182/blood-2008-06-165845).

Lactate, or lactic acid, is an organic compound with the formula $CH_3CH(OH)COOH$, which occurs in bodily fluids including blood. Blood tests for lactate are performed to determine the status of the acid base homeostasis in the body. Lactic acid is a product of cell metabolism that can accumulate when cells lack sufficient oxygen (hypoxia) and must turn to a less efficient means of energy production, or when a condition causes excess production or impaired clearance of lactate. Lactic acidosis can be caused by an inadequate amount of oxygen in cells and tissues (hypoxia), for example if someone has a condition that may lead to a decreased amount of oxygen delivered to cells and tissues, such as shock, septic shock or congestive heart failure, the lactate test can be used to help detect and evaluate the severity of hypoxia and lactic acidosis.

C-reactive protein (CRP) is a pentameric protein, which can be found in bodily fluids such as blood plasma. CRP levels can rise in response to inflammation. Measuring and charting CRP values can prove useful in determining disease progress or the effectiveness of treatments.

As used herein, the pneumonia severity index (PSI) or PORT Score is a clinical prediction rule that medical practitioners can use to calculate the probability of morbidity and mortality among patients with community acquired pneumonia. The PSI/PORT score is often used to predict the need for hospitalization in people with pneumonia, and the PSI score has been reported to accurately identify the patients with community-acquired pneumonia who are at low risk for death and other adverse outcomes. The prediction rules of the PSI score can therefore help physicians to make more rational decisions about hospitalization for patients with pneumonia. Mortality prediction is similar to that when using CURB-85.

As used herein, the "sequential organ failure assessment score" or "SOFA score" is one score used to track a patient's status during the stay in an intensive care unit (ICU). The SOFA score is a scoring system to determine the extent of a person's organ function or rate of failure. The score is based on six different scores, one each for the respiratory, cardio-vascular, hepatic, coagulation, renal and neurological systems. Both the mean and highest SOFA scores being predictors of outcome. An increase in SOFA score during the first 24 to 48 hours in the ICU predicts a mortality rate of at least 50% up to 95%. Scores less than 9 give predictive mortality at 33% while above 14 can be close to or above 95%.

As used herein, the quick SOFA score (qSOFA) is a scoring system that indicates a patient's organ dysfunction or mortality risk. The score is based on three criteria: 1) an alteration in mental status, 2) a decrease in systolic blood pressure of less than 100 mm Hg, 3) a respiration rate greater than 22 breaths per minute. Patients with two or more of these conditions are at greater risk of having an organ dysfunction or to die. A "positive" qSOFA Score (2) suggests high risk of poor outcome in patients with suspected infection. These patients should be more thoroughly assessed for evidence of organ dysfunction.

As used herein, "APACHE II" or "Acute Physiology and Chronic Health Evaluation II" is a severity-of-disease classification scoring system (Knaus et al., 1985). It can be applied within 24 hours of admission of a patient to an intensive care unit (ICU) and may be determined based on 12 different physiologic parameters: AaDO2 or PaO2 (depending on FiO2), temperature (rectal), mean arterial pressure, pH arterial, heart rate, respiratory rate, sodium (serum), potassium (serum), creatinine, hematocrit, white blood cell count and Glasgow Coma Scale.

As used herein, "SAPS II" or "Simplified Acute Physiology Score II" relates to a system for classifying the severity of a disease or disorder (see Le Gall J R et al., A new Simplified Acute Physiology Score (SAPS II) based on a European/North American multicenter study. JAMA. 1993; 270(24):2957-63.). The SAPS II score is made of 12 physiological variables and 3 disease-related variables. The point score is calculated from 12 routine physiological measurements, information about previous health status and some information obtained at admission to the ICU. The SAPS II score can be determined at any time, preferably, at day 2. The "worst" measurement is defined as the measure that correlates to the highest number of points. The SAPS II score ranges from 0 to 163 points. The classification system includes the followings parameters: Age, Heart Rate, Systolic Blood Pressure, Temperature, Glasgow Coma Scale, Mechanical Ventilation or CPAP, PaO2, FiO2, Urine Output, Blood Urea Nitrogen, Sodium, Potassium, Bicarbonate, Bilirubin, White Blood Cell, Chronic diseases and Type of admission. There is a sigmoidal relationship between mortality and the total SAPS II score. The mortality of a subject is 10% at a SAPSII score of 29 points, the mortality is 25% at a SAPSII score of 40 points, the mortality is 50% at a SAPSII score of 52 points, the mortality is 75% at a SAPSII score of 64 points, the mortality is 90% at a SAPSII score of 77 points (Le Gall loc. cit.).

As used herein, the term "sample" is a biological sample that is obtained or isolated from the patient or subject. "Sample" as used herein may, e.g., refer to a sample of bodily fluid or tissue obtained for the purpose of analysis, diagnosis, prognosis, or evaluation of a subject of interest, such as a patient. Preferably herein, the sample is a sample of a bodily fluid, such as blood, serum, plasma, cerebrospinal fluid, urine, saliva, sputum, pleural effusions, cells, a cellular extract, a tissue sample, any tissue sample from the upper or lower respiratory tract, a tissue biopsy, a stool sample and the like. Particularly, the sample is blood, blood plasma, blood serum.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g.

"Serum" in the context of the present invention is the liquid fraction of whole blood that is collected after the blood is allowed to clot. When coagulated blood (clotted blood) is centrifuged serum can be obtained as supernatant.

As used herein, "urine" is a liquid product of the body secreted by the kidneys through a process called urination (or micturition) and excreted through the urethra.

In embodiments of the present invention the condition requiring hospitalization may be sepsis, severe sepsis and/or septic shock. "Sepsis" in the context of the invention refers to a systemic response to infection. Alternatively, sepsis may be seen as the combination of SIRS with a confirmed infectious process or an infection. Sepsis may be characterized as clinical syndrome defined by the presence of both infection and a systemic inflammatory response (Levy M M et al. 2001 SCCM/ESICM/ACCP/ATS/SIS International Sepsis Definitions Conference. Crit Care Med. 2003 April; 31(4):1250-6). The term "sepsis" used herein includes, but is not limited to, sepsis, severe sepsis, and septic shock.

The term "sepsis" used herein includes, but is not limited to, sepsis, severe sepsis, and septic shock. Severe sepsis in refers to sepsis associated with organ dysfunction, hypoperfusion abnormality, or sepsis-induced hypotension. Hypoperfusion abnormalities include lactic acidosis, oliguria and acute alteration of mental status. Sepsis-induced hypotension is defined by the presence of a systolic blood pressure of less than about 90 mm Hg or its reduction by about 40 mm Hg or more from baseline in the absence of other causes for hypotension (e.g. cardiogenic shock). Septic shock is defined as severe sepsis with sepsis-induced hypotension persisting despite adequate fluid resuscitation, along with the presence of hypoperfusion abnormalities or organ dysfunction (Bone et al., CHEST 101(6): 1644-55, 1992).

The term sepsis may alternatively be defined as life-threatening organ dysfunction caused by a dysregulated host response to infection. For clinical operationalization, organ dysfunction can preferably be represented by an increase in the Sequential Organ Failure Assessment (SOFA) score of 2 points or more, which is associated with an in-hospital mortality greater than 10%. Septic shock may be defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 nmol/L (>18 mg/dL) in the absence of hypovolemia.

The term "sepsis" used herein relates to all possible stages in the development of sepsis. The term "sepsis" also includes severe sepsis or septic shock based on the SEPSIS-2 definition (Bone et al., 2009). The term "sepsis" also includes subjects falling within the SEPSIS-3 definition (Singer et al., 2016). The term "sepsis" used herein relates to all possible stages in the development of sepsis.

As used herein, "infection" within the scope of the invention means a pathological process caused by the invasion of normally sterile tissue or fluid by pathogenic or potentially pathogenic agents/pathogens, organisms and/or microorganisms, and relates preferably to infection(s) by bacteria, viruses, fungi, and/or parasites. In the context of the invention, infection relates in particular to viral infections with a SARS-virus. Infection can also be a combination of infections including a SARS-virus infection, such as a SARS-CoV2 infection, and one or more additional infections, such as a simultaneously or subsequently occurring infection or an infection that was already present at the time of SARS-virus infection, wherein the additional infection can be a bacterial infection, viral infection, and/or fungal infection. Infections with more than one additional pathogen can also occur, including at least one SARS-virus, and additionally one or more bacteria, viruses or fungi. For a triple infection with SARS-virus, a bacterium and a fungus can be envisioned. The infection can be a local or systemic infection. For the purposes of the invention, a viral infection may be considered as infection by a microorganism.

As used herein "infectious disease" comprises a viral infectious diseases or disorders that are associated with a primary viral infection, in particular a SARS-virus infection. In the context of the invention, the infectious disease can comprise in addition to the SARS-virus infection an infection with one or more bacteria and/or viruses and/or fungi.

Furthermore, the infection-related complication can be a "nosocomial" infection. Nosocomial infections are also called hospital-acquired infections (HAI) are infections that are acquired in a hospital or other health care facility. To emphasize both hospital and nonhospital settings, it is sometimes instead called a health care-associated infection (HAI or HCAI). Such an infection can be acquired in hospital, nursing home, rehabilitation facility, outpatient clinic, or other clinical settings. Nosocomial infection may be spread to the susceptible patient in the clinical setting by various means. Health care staff can spread infection, in addition to contaminated equipment, bed linens, or air droplets. The infection can originate from the outside environment, another infected patient, staff that may be infected, or in some cases, the source of the infection cannot be determined. In some cases the microorganism originates from the patient's own skin microbiota, becoming opportunistic after surgery or other procedures that compromise the protective skin barrier. Though the patient may have contracted the infection from their own skin, the infection is still considered nosocomial since it develops in the health care setting.

Further, the subject suffering from an infection can suffer from more than one source(s) of infection simultaneously. For example, the subject suffering from an infection can suffer from a bacterial infection and viral infection; from a viral infection and fungal infection; from a bacterial and fungal infection, and from a bacterial infection, fungal infection and viral infection, or suffer from a mixed infection comprising one or more of the infections listed herein, including potentially a superinfection, for example one or more bacterial infections in addition to one or more viral infections and/or one or more fungal infections.

In the context of the present invention, the term "medical treatment" or "treatment" comprises various treatments and therapeutic strategies, which comprise, without limitation, anti-inflammatory strategies, administration of ADM-antagonists such as therapeutic antibodies, si-RNA or DNA, the extracorporeal blood purification or the removal of harmful substances via apheresis, dialyses, adsorbers to prevent the cytokine storm, removal of inflammatory mediators, plasma apheresis, administration of vitamines such as vitamin C, surgery, emergency surgery, ventilation like mechanical ventilation and non-mechanical ventilation, to provide the body with sufficient oxygen, for example, focus cleaning procedures, transfusion of blood products, infusion of colloids, organ replacement, such as renal or liver replacement, antibiotic treatment, invasive mechanical ventilation, non-invasive mechanical ventilation, vasopressor use, fluid therapy, apheresis and measures for organ protection.

A skilled person is capable of determining which of the treatments described herein require administration in a hospital setting.

A skilled person is also capable of determining which medical conditions, and which degrees of severity of such medical conditions, require treatments only (or primarily) available in hospital settings, for example in the ED or ICU.

Further treatments of the present invention comprise the administration of cells or cell products like stem cells, blood or plasma, and the stabilization of the patients circulation and the protection of endothelial glycocalyx, for example via optimal fluid management strategies, for example to reach normovolemia and prevent or treat hypervolemia or hypovolemia. Moreover, vasopressors or e.g. catecholamine as well as albumin or heparanase inhibition via unfractionated heparin or N-desulfated re-N-acetylated heparin are useful treatments to support the circulation and endothelial layer.

Additionally, medical treatments of the present invention comprise, without limitation, stabilization of the blood clotting, anti-fibrinolytic treatment, iNOS inhibitors, anti-inflammatory agents like hydrocortisone, sedatives and analgetics as well as insulin.

Artificial and mechanical ventilation are effective approaches to enhance proper gas exchange and ventilation and aim to save life during severe hypoxemia. Artificial ventilation relates to assisting or stimulating respiration of the subject. Artificial ventilation may be selected from the group consisting of mechanical ventilation, manual ventilation, extracorporeal membrane oxygenation (ECMO) and noninvasive ventilation (NIV). Mechanical ventilation relates to a method to mechanically assist or replace spontaneous breathing. This may involve a machine called a ventilator. Mechanical ventilation may be High-Frequency Oscillatory Ventilation or Partial Liquid Ventilation.

"Renal replacement therapy" (RRT) relates to a therapy that is employed to replace the normal blood-filtering function of the kidneys. Renal replacement therapy may refer to dialysis (e.g. hemodialysis or peritoneal dialysis), hemofiltration, and hemodiafiltration. Such techniques are various ways of diverting the blood into a machine, cleaning it, and then returning it to the body. Renal replacement therapy may also refer to kidney transplantation, which is the ultimate form of replacement in that the old kidney is replaced by a donor kidney. The hemodialysis, hemofiltration, and hemodiafiltration may be continuous or intermittent and can use an arteriovenous route (in which blood leaves from an artery and returns via a vein) or a venovenous route (in which blood leaves from a vein and returns via a vein). This results in various types of RRT. For example, the renal replacement therapy may be selected from the group of, but not limited to continuous renal replacement therapy (CRRT), continuous hemodialysis (CHD), continuous arteriovenous hemodialysis (CAVHD), continuous venovenous hemodialysis (CVVHD), continuous hemofiltration (CHF), continuous arteriovenous hemofiltration (CAVH or CAVHF), continuous venovenous hemofiltration (CVVH or CVVHF), continuous hemodiafiltration (CHDF), continuous arterio-venous hemodiafiltration (CAVHDF), continuous venovenous hemodiafiltration (CVVHDF), intermittent renal replacement therapy (IRRT), intermittent hemodialysis (IHD), intermittent venovenous hemodialysis (IVVHD), intermittent hemofiltration (IHF), intermittent venovenous hemofiltration (IVVH or IVVHF), intermittent hemodiafiltration (IHDF) and intermittent venovenous hemodiafiltration (IVVHDF).

Medical treatment also comprises methods to avoid hypothermia which includes the use of warmed intravenous fluids and warm air blankets.

Medical treatment also comprises wound management including haemorrhage control, bleeding control techniques with or without tourniquets, wound cleaning, local anaesthetic application, wound closure techniques where skin adhesive strips, tissue adhesive glue, sutures, staples and wound dressings can be used.

The term "fluid therapy" as used in the present invention relates to the administration of a liquid to a subject in need thereof. The terms "fluid replacement" or "fluid resuscitation" may also be used. Fluid therapy comprises but is not limited to fluids being replaced with oral rehydration therapy (drinking), intravenous therapy, rectally, or the injection of fluid into subcutaneous tissue. Intravenous methods are preferred. "Colloids" are dispersions of large organic molecules (e.g., Gelofusin, Voluven). Colloids are typically suspensions of molecules within a carrier solution that are relatively incapable of crossing the healthy semipermeable capillary membrane due to their molecular weight. In one embodiment, the method indicates that the fluid therapy comprises a colloid selected from gelatin, albumin and/or starch solution, or blood or a fluid derived from blood. "Crystalloids" are solutions of small molecules in water (e.g., sodium chloride, glucose, Hartmann's solution, or Ringer's solution). Crystalloids are typically solutions of ions that are freely permeable but contain concentrations of sodium and chloride that determine the tonicity of the fluid.

"Fluid management" refers to the monitoring and controlling of the fluid status of a subject and the administration of fluids to stabilize the circulation or organ vitality, by e.g. oral, enteral or intravenous fluid administration. It comprises the stabilization of the fluid and electrolyte balance or the prevention or correction of hyper- or hypovolenia as well as the supply of blood products.

Cleaning Procedures are hygienic methods to prevent subjects from infections, especially nosocomial infections, comprising disinfection of all organic and inorganic surfaces that could get in contact with a patient, such as for example, skin, objects in the patient's room, medical devices, diagnostic devices, or room air. Cleaning procedures include the use of protective clothes and units, such as mouth guards, gowns, gloves or hygiene lock, and actions like restricted patient visits. Furthermore, cleaning procedures comprise the cleaning of the patient itself and the clothes or the patient.

In a preferred embodiment, the term "medical treatment" or "treatment" comprises antibiotic treatment such as intravenous antibiotic, oral antibiotics or topical antibiotics.

In the context of the present invention, the term "medical treatment" or "treatment" comprises various treatments and therapeutic strategies, which comprise, without limitation, anti-inflammatory strategies, administration of proADM-antagonists such as therapeutic antibodies, si-RNA or DNA, the extracorporeal blood purification or the removal of harmful substances via apheresis, dialyses, adsorbers to prevent the cytokine storm, removal of inflammatory mediators, plasma apheresis, administration of vitamines such as vitamin C, ventilation like mechanical ventilation and non-mechanical ventilation, to provide the body with sufficient oxygen, for example, focus cleaning procedures, transfusion of blood products, infusion of colloids, renal or liver replacement, antibiotic treatment, invasive mechanical ventilation, non-invasive mechanical ventilation, renal replacement therapy, vasopressor use, fluid therapy, apheresis and measures for organ protection, provision of corticosteroids, blood or platelet transfusion, transfusion of blood components, such as serum, plasma or specific cells or combinations thereof, drugs promoting the formation of thrombocytes, source control, surgeries, causative treatment, performing a splenectomy or in regards to cardiovascular and cerebrovascular events an anticoagulation therapy, an oxygen therapy, a lysis therapy such as a thrombolysis, a percutaneous coronary intervention, a percutaneous transluminal angioplast, a coronary artery bypass graft and/or a stent implantation. In some embodiments the medical treatment of a cardiovascular and cerebrovascular events includes the administration of nitroglycerin, acetylsalicylic acid, a beta-blocker, an ACE Inhibitor and/or clopidogrel.

In regard to perioperative myocardial infarction as means of a prevention the medical treatment may comprise in particular the administration of statins, β-blockers, α2-adrenergic agonists or other anti-ischemic agents such calcium-channel blockers or nitrates.

A skilled person is capable of determining which of the treatments described herein require administration in a hospital setting.

A skilled person is also capable of determining which medical conditions, and which degrees of severity of such medical conditions, require treatments only (or primarily) available in hospital settings, for example in the ED or ICU.

Further treatments of the present invention comprise the administration of cells or cell products like stem cells, blood or plasma, and the stabilization of the patients circulation and the protection of endothelial glycocalyx, for example via optimal fluid management strategies, for example to reach normovolemia and prevent or treat hypervolemia or hypovolemia. Moreover, vasopressors or e.g. catecholamine as well as albumin or heparanase inhibition via unfractionated heparin or N-desulfated re-N-acetylated heparin are useful treatments to support the circulation and endothelial layer.

In a preferred embodiment, the term "medical treatment" or "treatment" comprises antibiotic treatment such as intravenous antibiotic, oral antibiotics or topical antibiotics. In a more preferred embodiment, the term "medical treatment" or "treatment" comprises intravenously applied antibiotic treatment.

Additionally, medical treatments of the present invention comprise, without limitation, stabilization of the blood dotting, iNOS inhibitors, anti-inflammatory agents like hydrocortisone, sedatives and analgetics as well as insulin.

Medical treatment also comprises methods to avoid hypothermia which includes the use of warmed intravenous fluids and warm air blankets.

Medical treatment also comprises wound management including haemorrhage control, bleeding control techniques with or without tourniquets, wound cleaning, local anaesthetic application, wound closure techniques where skin adhesive strips, tissue adhesive glue, sutures, staples and wound dressings can be used.

A medical treatment of the present invention may be an antibiotic treatment, wherein one or more "antibiotics" or "antibiotic agents" may be administered if an infection has been diagnosed or prognosed by the method of the invention. Antibiotics or antibiotic agents according to the present invention also encompass potentially the anti-fungal or anti-viral compounds used to treat a diagnosed infection or sepsis. The antibiotic agents commonly applied in the treatment of any given infection, as separated into the classes of pathogen are:

Gram positive coverage: Penicillins, (ampicillin, amoxicillin), penicillinase resistant, (Dicloxacillin, Oxacillin), Cephalosporins (1st and 2nd generation), Macrolides (Erythromycin, Clarithromycin, Azithromycin), Quinolones (gatifloxacin, moxifloxacin, levofloxacin), Vancomycin, Sulfonamide/trimethoprim, Clindamycin, Tetracyclines, Chloramphenicol, Linezolid, Synercid.

Gram negative coverage: Broad spectrum penicillins (Ticarcillin, clavulanate, piperacillin, tazobactam), Cephalosporins (2nd, 3rd, and 4th generation), Aminoglycosides, Macrolides, Azithromycin, Quinolones (Ciprofloxacin), Monobactams (Azetreonam), Sulfonamide/trimethoprim, Carbapenems (Imipenem), Chloramphenicol.

Pseudomonas coverage: Ciprofloxacin, Aminoglycosides, Some 3rd generation cephalosporins, 4th generation cephalosporins, Broad spectrum penicillins, Carbapenems.

Fungal treatments: Allylamines, Amphotericin B, Fluconazole and other Azoles, itraconazole, voriconazole, posaconazole, ravuconazole, echinocandins, Flucytosine, sordarins, chitin synthetase inhibitors, topoisomerase inhibitors, lipopeptides, pradimycins, Liposomal nystatin, Voriconazole, Echinocandins, Imidazole, Triazole, Thiazole, Polyene.

Anti-viral treatments: Abacavir, Acyclovir (Aciclovir), activated caspase oligomerizer, Adefovir, Amantadine, Amprenavir (Agenerase), Ampligen, Arbidol, Atazanavir, Atripla, Balavir, Cidofovir, Combivir, Dolutegravir, Darunavir, Delavirdine, Didanosine, Double-stranded RNA, Docosanol, Edoxudine, Efavirenz, Emtricitabine, Enfuvirtide, Entecavir, Ecoliever, Famciclovir, Fixed dose combination (antiretroviral), Fomivirsen, Fosamprenavir, Foscamet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Morpholinos, Nelfinavir, Nevirapine, Nexavir, Nitazoxanide, Nucleoside analogues, Novir, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Ribozymes, Rifampicin, Rimantadine, Ritonavir, RNase H, protease inhibitors, Pyramidine, Saquinavir, Sofosbuvir, Stavudine, Synergistic enhancer (antiretroviral), Telaprevir, Tenofovir. Tenofovir disoproxil, Tipranavir, Trifluridine, Trizivir, Tromantadine, Truvada, Valaciclovir (Valtrex), Valganciclovir, Vicriviroc. Vidarabine, Viramidine, Zalcitabine, Zanamivir (Relenza), Zidovudine.

Furthermore, antibiotic agents comprise bacteriophages for treatment of bacterial infections, synthetic antimicrobial peptides or iron-antagonists/iron chelator. Also, therapeutic antibodies or antagonist against pathogenic structures like anti-VAP-antibodies, anti-resistant clone vaccination, administration of immune cells, such as in vitro primed or modulated T-effector cells, are antibiotic agents that represent treatment options for critically ill patients, such as sepsis patients. Further antibiotic agents/treatments or therapeutic strategies against infection or for the prevention of new infections include the use of antiseptics, decontamination products, anti-virulence agents like liposomes, sanitation, wound care, surgery.

It is also possible to combine several of the aforementioned antibiotic agents or treatments strategies.

According to the present invention proADM and optionally PCT and/or other markers or clinical scores are employed as markers for the diagnosis, prognosis, prediction, risk assessment and/or risk stratification of a patient in developing a medical condition that requires treatment in hospital who presents with symptoms of an infectious disease.

A skilled person is capable of obtaining or developing means for the identification, measurement, determination and/or quantification of any one of the above ADM molecules, or fragments or variants thereof, as well as the other markers of the present invention according to standard molecular biological practice.

The level of proADM or fragments thereof as well as the levels of other markers of the present invention can be determined by any assay that reliably determines the concentration of the marker. Particularly, mass spectrometry (MS) and/or immunoassays can be employed as exemplified in the appended examples. As used herein, an immunoassay is a biochemical test that measures the presence or concentration of a macromolecule/polypeptide in a solution through the use of an antibody or antibody binding fragment or immunoglobulin.

Methods of determining ADM or other the markers such as PCT used in the context of the present invention are intended in the present invention. By way of example, a method may be employed selected from the group consisting of mass spectrometry (MS), luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats such as for instance immunochromatographic strip tests, rare cryptate assay, and automated systems/analyzers.

Determination of ADM and optionally other markers based on antibody recognition is a preferred embodiment of the invention. As used herein, the term, "antibody" refers to immunoglobulin molecules and immunologically active portions of immunoglobulin (Ig) molecules, i.e., molecules that contain an antigen binding site that specifically binds (immuno reacts with) an antigen. According to the invention, the antibodies may be monoclonal as well as polyclonal antibodies. Particularly, antibodies that are specifically binding to at least proADM or fragments thereof are used.

An antibody is considered to be specific, if its affinity towards the molecule of interest, e.g. ADM, or the fragment thereof is at least 50-fold higher, preferably 100-fold higher, most preferably at least 1000-fold higher than towards other molecules comprised in a sample containing the molecule of interest. It is well known in the art how to develop and to select antibodies with a given specificity. In the context of the invention, monoclonal antibodies are preferred. The antibody or the antibody binding fragment binds specifically to the herein defined markers or fragments thereof. In particular, the antibody or the antibody binding fragment binds to the herein defined peptides of ADM. Thus, the herein defined peptides can also be epitopes to which the antibodies specifically bind. Further, an antibody or an antibody binding fragment is used in the methods and kits of the invention that binds specifically to ADM or proADM, particularly to MR-proADM.

Further, an antibody or an antibody binding fragment is used in the methods and kits of the invention that binds specifically to proADM or fragments thereof and optionally to other markers of the present inventions such as PCT. Exemplary immunoassays can be luminescence immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, rare cryptate assay. Further, assays suitable for point-of-care testing and rapid test formats such as for instance immune-chromatographic strip tests can be employed. Automated immunoassays are also intended, such as the KRYPTOR assay.

Alternatively, instead of antibodies, other capture molecules or molecular scaffolds that specifically and/or selectively recognize ADM may be encompassed by the scope of the present invention. Herein, the term "capture molecules" or "molecular scaffolds" comprises molecules which may be used to bind target molecules or molecules of interest, i.e. analytes (e.g. ADM, proADM, MR-proADM, and PCT), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may, for instance, be mediated by ionic, van-der-Waals, pi-pi, sigma-pi, hydrophobic or hydrogen bond interactions or a combination of two or more of the aforementioned interactions or covalent interactions between the capture molecules or molecular scaffold and the target molecules or molecules of interest. In the context of the present invention, capture molecules or molecular scaffolds may for instance be selected from the group consisting of a nucleic acid molecule, a carbohydrate molecule, a PNA molecule, a protein, a peptide and a glycoprotein. Capture molecules or molecular scaffolds include, for example, aptamers, DARpins (Designed Ankyrin Repeat Proteins). Affimers and the like are included.

In certain aspects of the invention, the method is an immunoassay comprising the steps of:

a) contacting the sample with
   i. a first antibody or an antigen-binding fragment or derivative thereof specific for a first epitope of said proADM, and
   ii. a second antibody or an antigen-binding fragment or derivative thereof specific for a second epitope of said proADM; and
b) detecting the binding of the two antibodies or antigen-binding fragments or derivates thereof to said proADM.

Preferably, one of the antibodies can be labeled and the other antibody can be bound to a solid phase or can be bound selectively to a solid phase. In a particularly preferred aspect of the assay, one of the antibodies is labeled while the other is either bound to a solid phase or can be bound selectively to a solid phase. The first antibody and the second antibody can be present dispersed in a liquid reaction mixture, and wherein a first labeling component which is part of a labeling system based on fluorescence or chemiluminescence extinction or amplification is bound to the first antibody, and a second labeling component of said labeling system is bound to the second antibody so that, after binding of both antibodies to said proADM or fragments thereof to be detected, a measurable signal which permits detection of the resulting sandwich complexes in the measuring solution is generated. The labeling system can comprise a rare earth cryptate or chelate in combination with a fluorescent or chemiluminescent dye, in particular of the cyanine type.

In a preferred embodiment, the method is executed as heterogeneous sandwich immunoassay, wherein one of the antibodies is immobilized on an arbitrarily chosen solid phase, for example, the walls of coated test tubes (e.g. polystyrol test tubes; coated tubes; CT) or microtiter plates, for example composed of polystyrol, or to particles, such as for instance magnetic particles, whereby the other antibody has a group resembling a detectable label or enabling for selective attachment to a label, and which serves the detection of the formed sandwich structures. A temporarily delayed or subsequent immobilization using suitable solid phases is also possible.

The method according to the present invention can furthermore be embodied as a homogeneous method, wherein the sandwich complexes formed by the antibody/antibodies and the marker, ADM or a fragment thereof, which is to be detected remains suspended in the liquid phase. In this case it is preferred, that when two antibodies are used, both antibodies are labeled with parts of a detection system, which leads to generation of a signal or triggering of a signal if both antibodies are integrated into a single sandwich. Such techniques are to be embodied in particular as fluorescence enhancing or fluorescence quenching detection methods. A particularly preferred aspect relates to the use of detection reagents which are to be used pair-wise, such as for example the ones which are described in U.S. Pat. No. 4,882,733, EP0180492 or EP0539477 and the prior art cited therein. In this way, measurements in which only reaction products comprising both labeling components in a single immune-complex directly in the reaction mixture are detected, become possible. For example, such technologies are offered under the brand names TRACE® (Time Resolved Amplified Cryptate Emission) or KRYPTOR®, implementing the teachings of the above-cited applications. Therefore, in particular preferred aspects, a diagnostic device is used to carry out the herein provided method. For example, the level of proADM or fragments thereof and/or the level of any further marker of the herein provided method, such as PCT, is determined.

In particular preferred aspects, the diagnostic device is KRYPTOR®.

The level of the marker of the present invention, e.g. the proADM or fragments thereof, PCT or fragments thereof, or other markers, can also be determined by a mass spectrometric (MS) based methods. Such a method may comprise detecting the presence, amount or concentration of one or more modified or unmodified fragment peptides of e.g. ADM or the PCT in said biological sample or a protein digest (e.g. tryptic digest) from said sample, and optionally separating the sample with chromatographic methods, and subjecting the prepared and optionally separated sample to MS analysis. For example, selected reaction monitoring (SRM), multiple reaction monitoring (MRM) or parallel reaction monitoring (PRM) mass spectrometry may be used in the MS analysis, particularly to determine the amounts of proADM or fragments thereof.

Herein, the term "mass spectrometry" or "MS" refers to an analytical technique to identify compounds by their mass. In order to enhance the mass resolving and mass determining capabilities of mass spectrometry, the samples can be processed prior to MS analysis. Accordingly, the invention relates to MS detection methods that can be combined with immuno-enrichment technologies, methods related to sample preparation and/or chromatographic methods, preferably with liquid chromatography (LC), more preferably with high performance liquid chromatography (HPLC) or ultra high performance liquid chromatography (UHPLC). Sample preparation methods comprise techniques for lysis, fractionation, digestion of the sample into peptides, depletion, enrichment, dialysis, desalting, alkylation and/or peptide reduction. However, these steps are optional. The selective detection of analyte ions may be conducted with tandem mass spectrometry (MS/MS). Tandem mass spectrometry is characterized by mass selection step (as used herein, the term "mass selection" denotes isolation of ions having a specified m/z or narrow range of m/z's), followed by fragmentation of the selected ions and mass analysis of the resultant product (fragment) ions.

The skilled person is aware how quantify the level of a marker in the sample by mass spectrometric methods. For example, relative quantification "rSRM" or absolute quantification can be employed as described above.

Moreover, the levels (including reference levels) can be determined by mass spectrometric based methods, such as methods determining the relative quantification or determining the absolute quantification of the protein or fragment thereof of interest.

Relative quantification "rSRM" may be achieved by:

1. Determining increased or decreased presence of the target protein by comparing the SRM (Selected reaction monitoring) signature peak area from a given target fragment peptide detected in the sample to the same SRM signature peak area of the target fragment peptide in at least a second, third, fourth or more biological samples.

2. Determining increased or decreased presence of target protein by comparing the SRM signature peak area from a given target peptide detected in the sample to SRM signature peak areas developed from fragment peptides from other proteins, in other samples derived from different and separate biological sources, where the SRM signature peak area comparison between the two samples for a peptide fragment are normalized for e.g. to amount of protein analyzed in each sample.

3. Determining increased or decreased presence of the target protein by comparing the SRM signature peak area for a given target peptide to the SRM signature peak areas from other fragment peptides derived from different proteins within the same biological sample in order to normalize changing levels of histones protein to levels of other proteins that do not change their levels of expression under various cellular conditions.

4 These assays can be applied to both unmodified fragment peptides and to modified fragment peptides of the target proteins, where the modifications include, but are not limited to phosphorylation and/or glycosylation, acetylation, methylation (mono, di, tri), citrullination, ubiquitinylation and where the relative levels of modified peptides are determined in the same manner as determining relative amounts of unmodified peptides.

Absolute quantification of a given peptide may be achieved by:

1. Comparing the SRM/MRM signature peak area for a given fragment peptide from the target proteins in an individual biological sample to the SRM/MRM signature peak area of an internal fragment peptide standard spiked into the protein lysate from the biological sample. The internal standard may be a labeled synthetic version of the fragment peptide from the target protein that is being interrogated or the labeled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas. This can be applied to unmodified fragment peptides and modified fragment peptides, where the modifications include but are not limited to phosphorylation and/or glycosylation, acetylation, methylation (e.g. mono-, di-, or tri-methylation), citrullination, ubiquitinylation, and where the absolute levels of modified peptides can be determined in the same manner as determining absolute levels of unmodified peptides.

2. Peptides can also be quantified using external calibration curves. The normal curve approach uses a constant amount of a heavy peptide as an internal standard and a varying amount of light synthetic peptide spiked into the sample. A representative matrix similar to that of the test samples needs to be used to construct standard curves to account for a matrix effect. Besides, reverse curve method circumvents the issue of endogenous analyte in the matrix, where a constant amount of light peptide is spiked on top of the endogenous analyte to create an internal standard and varying amounts of heavy peptide are spiked to create a set of concentration standards. Test samples to be compared with either the normal or reverse curves are spiked with the same amount of standard peptide as the internal standard spiked into the matrix used to create the calibration curve.

The invention further relates to kits, the use of the kits and methods wherein such kits are used. The invention relates to kits for carrying out the herein above and below provided methods. The herein provided definitions, e.g. provided in relation to the methods, also apply to the kits of the invention. In particular, the invention relates to kits for therapy monitoring, comprising the prognosis, risk assessment or risk stratification of a subsequent adverse event in the health of a patient, wherein said kit comprises detection reagents for determining the level proADM or fragment(s) thereof, and optionally additionally for determining the level of PCT, lactate and/or C-reactive protein or fragment(s) thereof, in a sample from a subject, and—detection reagents for determining said level of ADM in said sample of said subject, and reference data, such as a reference level, corresponding to high and/or low severity levels of ADM, wherein the low severity level is below 4 nmol/l, preferably below 3 nmol/l, more preferably below 2.7 nmol/l, and the high seventy level is above 6.5 nmol/l, preferably above 6.95 nmol/l, more preferably above 10.9 nmol/l, and optionally PCT, lactate and/or C-reactive protein levels, wherein said reference data is preferably stored on a computer readable medium and/or employed in the form of computer executable code configured for comparing the determined levels of proADM or fragment(s) thereof, and optionally additionally the determined levels of PCT, lactate and/or C-reactive protein or fragment(s) thereof, to said reference data.

As used herein, "reference data" comprise reference level(s) of ADM and optionally PCT, lactate, C-reactive protein and/or other suitable markers disclosed herein, such as for example markers of rhabdomyolysis. The levels of ADM and optionally other markers such as PCT, lactate and/or C-reactive protein in the sample of the subject can be compared to the reference levels comprised in the reference data of the kit. The reference levels are herein described above and are exemplified also in the appended examples. The reference data can also include a reference sample to which the level of ADM and optionally PCT, lactate and/or C-reactive protein is compared. The reference data can also include an instruction manual how to use the kits of the invention.

The kit may additionally comprise items useful for obtaining a sample, such as a blood sample, for example the kit may comprise a container, wherein said container comprises a device for attachment of said container to a cannula or syringe, is a syringe suitable for blood isolation, exhibits an internal pressure less than atmospheric pressure, such as is suitable for drawing a pre-determined volume of sample into said container, and/or comprises additionally detergents, chaotropic salts, ribonuclease inhibitors, chelating agents, such as guanidinium isothiocyanate, guanidinium hydrochloride, sodium dodecylsulfate, polyoxyethylene sorbitan monolaurate, RNAse inhibitor proteins, and mixtures thereof, and/or A filter system containing nitro-cellulose, silica matrix, ferromagnetic spheres, a cup retrieve spill over, trehalose, fructose, lactose, mannose, poly-ethylenglycol, glycerol, EDTA, TRIS, limonene, xylene, benzoyl, phenol, mineral oil, anilin, pyrol, citrate, and mixtures thereof.

As used herein, the "detection reagent" or the like are reagents that are suitable to determine the herein described marker(s), e.g. of ADM, PCT, lactate and/or C-reactive protein. Such exemplary detection reagents are, for example, ligands, e.g. antibodies or fragments thereof, which specifically bind to the peptide or epitopes of the herein described marker(s). Such ligands might be used in immunoassays as described above. Further reagents that are employed in the immunoassays to determine the level of the marker(s) may also be comprised in the kit and are herein considered as detection reagents. Detection reagents can also relate to reagents that are employed to detect the markers or fragments thereof by MS based methods. Such detection reagent can thus also be reagents. e.g. enzymes, chemicals, buffers, etc, that are used to prepare the sample for the MS analysis. A mass spectrometer can also be considered as a detection reagent. Detection reagents according to the invention can also be calibration solution(s), e.g. which can be employed to determine and compare the level of the marker(s).

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having an infection and "disease" populations, e.g. subjects having an infection. For any particular marker (like ADM), a distribution of marker levels for subjects with and without a disease/condition will likely overlap. Under such conditions, a test does not absolutely distinguish normal from disease with 100% accuracy, and the area of overlap might indicate where the test cannot distinguish normal from disease. A threshold is selected, below which the test is considered to be abnormal and above which the test is considered to be normal or below or above which the test indicates a specific condition, e.g. infection. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art; see, e.g., Hanley et al. 1982. Radiology 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

Accordingly, the invention comprises the administration of an antibiotic suitable for treatment on the basis of the information obtained by the method described herein.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

Thus, the terms "comprising"/"including"/"having" mean that any further component (or likewise features, integers, steps and the like) can/may be present. The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

FIGURES

The invention is further described by the following figures. These are not intended to limit the scope of the invention, but represent preferred embodiments of aspects of the invention provided for greater illustration of the invention described herein.

FIG. 1: Flow chart of the study. Abbreviations: KSA, Cantonal Hospital Aarau; SARS-CoV-2, severe acute respiratory syndrome coronavirus 2; REHA, Rehabilitation.

Figure 2:
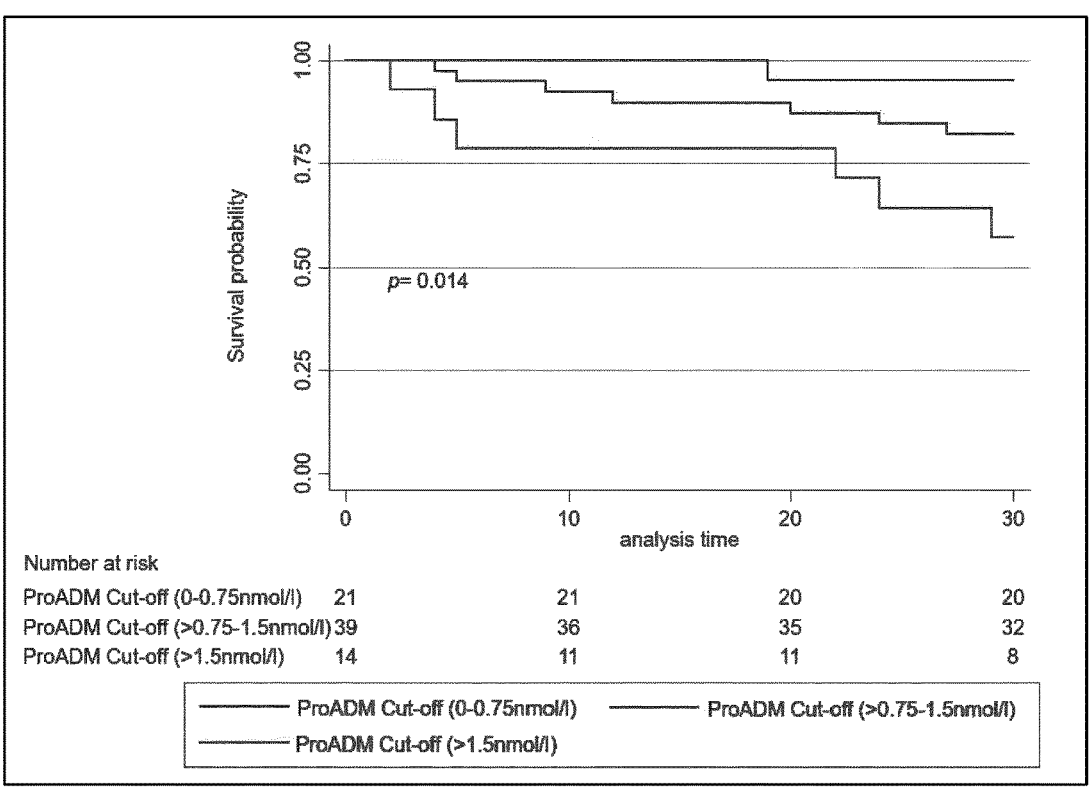
Figure 2:
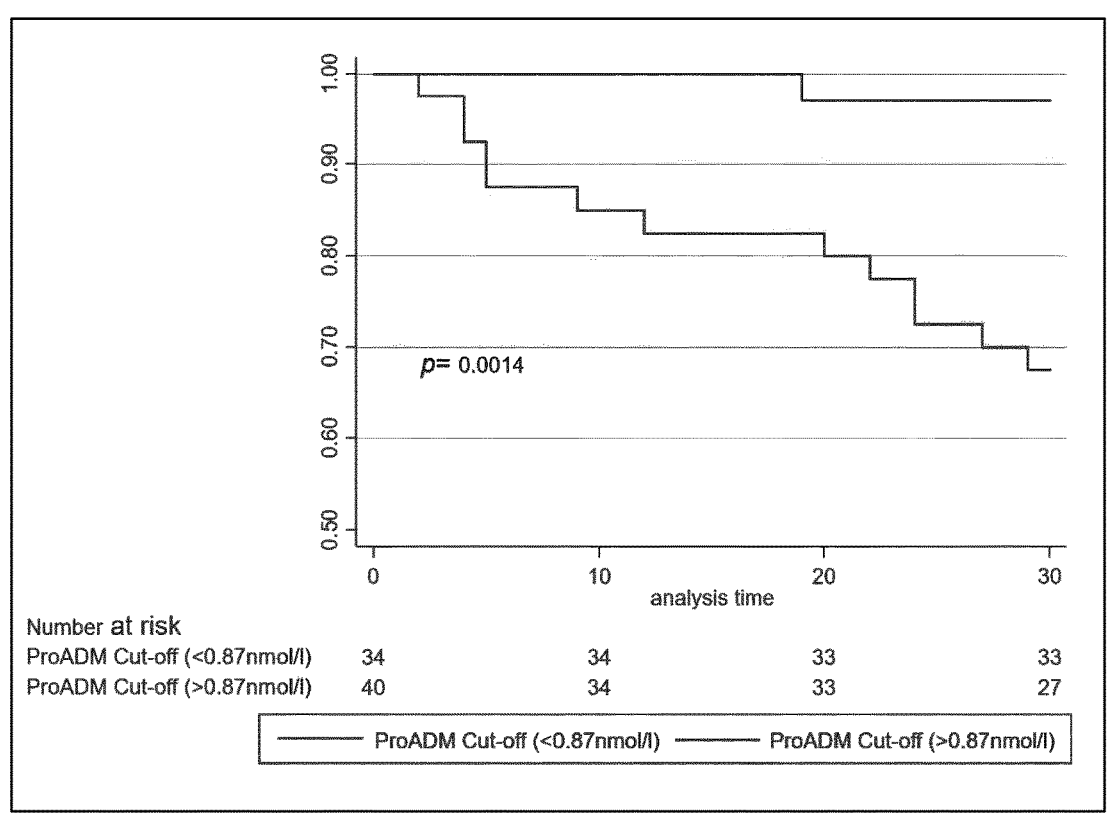
Figure 2:
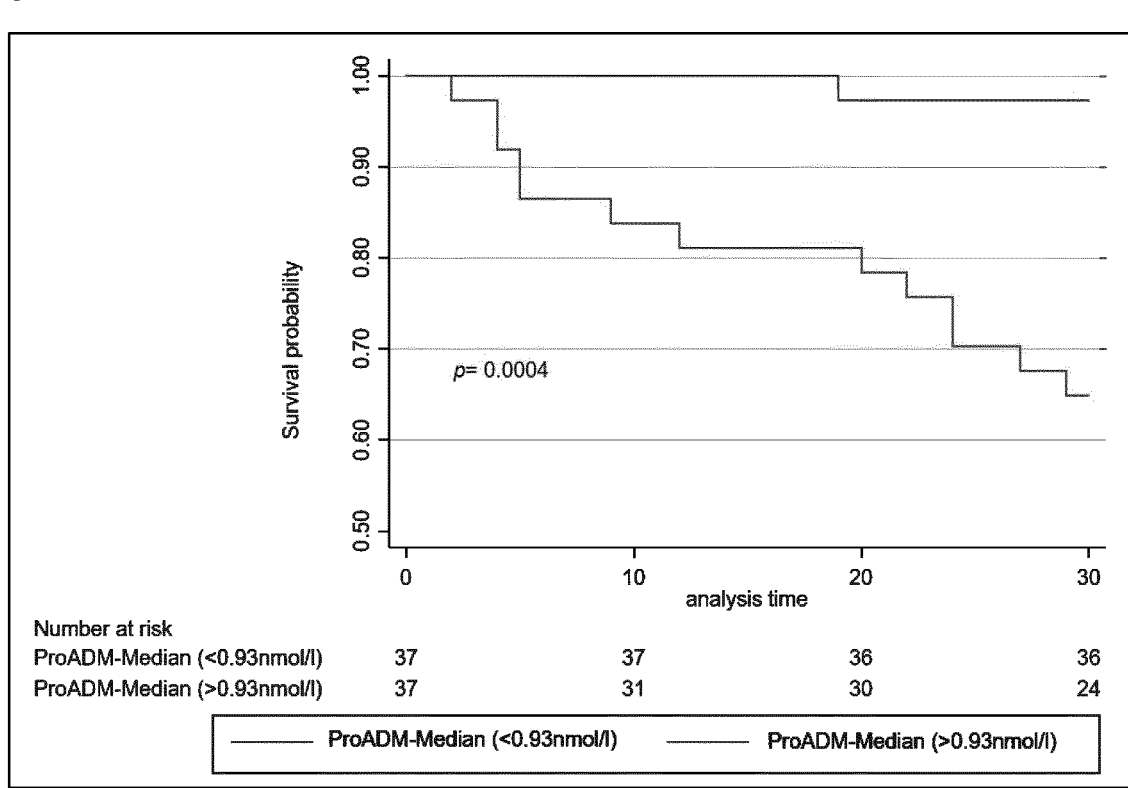

FIG. 2: Survival according to different proADM cut-offs and median at time point 1 (within 24 h from admission): A) 0-0.75 nmol/L, >0.75-1.5 nmol/L, >1.5 nmol/L; B) <0.87 nmol/L, >0.87 nmol/L; C) Median: <0.93 nmol/L, >0.93 nmol/L. Abbreviations: MR-proADM, Mid-regional pro-Adrenomedullin.

Figure 3:
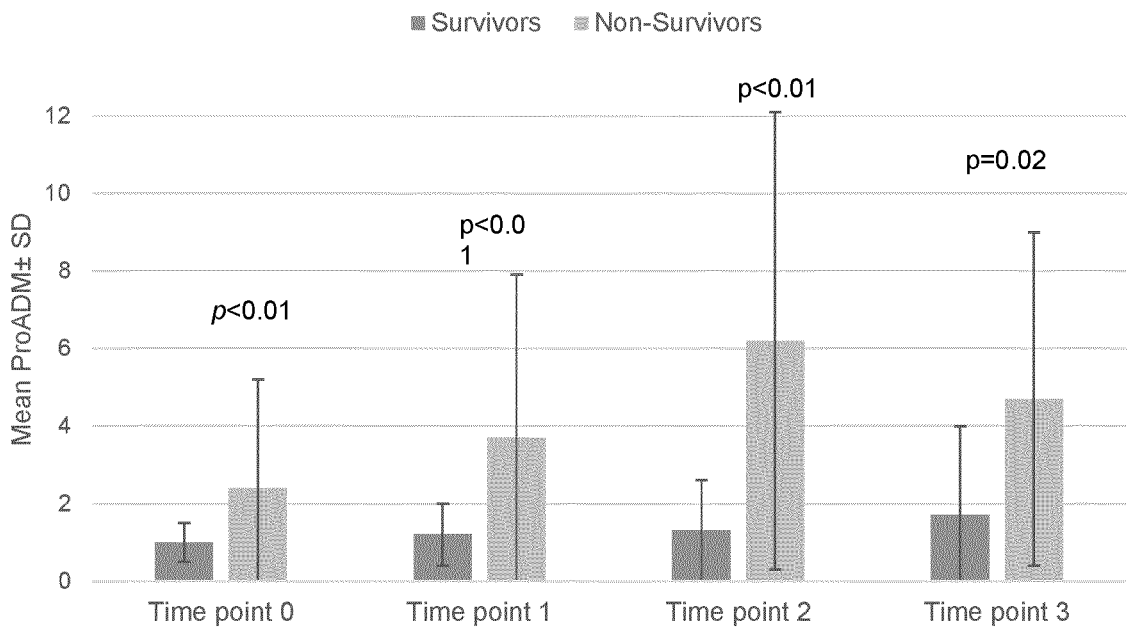

FIG. 3: Mean MR-proADM values at the different measurement time points for survivors and non-survivors. Abbreviations: MR-proADM, pro-adrenomedullin; SD, Standard Deviation

EXAMPLES

The invention is further described by the following examples. These are not intended to limit the scope of the invention, but represent preferred embodiments of aspects of the invention provided for greater illustration of the invention described herein.

Example 1

Pro-ADM (MR-proADM) values were measured in plasma samples of 90 patients that required hospitalization due to SARS-CoV-2 infection. Pro-ADM in samples was quantified by using the MR-proADM Kryptor assay (Thermo Fisher Scientific, BRAHMS GmbH).

Available samples were measured at different time points: time point 1 (within 24 h (day 1) from hospital admission), time point 2 (day 3 or 4 from hospitalization), time point 3 (day 5 or 6 from hospitalization) and time point 4 (day 7 or 8 from hospitalization). During the course of clinical care, 24 patients were transferred to the intensive care unit (ICU). Pro-ADM values were related to in-hospital mortality of patients.

TABLE 1

Crude and adjusted association of overall pro ADM and cut-offs and in hospital mortality.

| Pro-ADM Time Point | Cut off nmol/l | Survivors N = 70 | Non-Survivors N = 17 | p-Value | AUC | Univariate OR (95% CI), p-value | Multivariate OR* (95% CI), p-value |
|---|---|---|---|---|---|---|---|
| Time Point 1 | | | | | | | |
| Pro ADM overall, median (IQR) | | 0.8 (0.7 1.1) | 1.3 (1.1; 2.3) | <0.01 | 0.79 | 3.2 (1.3 to 8.1), p = 0.012 | 5.3 (1.3 to 21.9), p = 0.02 |
| Pro ADM cut offs n (%) | <0.75 | 20 (34%) | 1 (7%) | 0.02 | | | |
| | >0.75 | 31 (53%) | 7 (50%) | | | 4.5 (0.5 to 39.5), p = 0.17 | 2.7 (0.3 to 27.4), p = 0.406 |
| | >1.5 | 8 (14%) | 6 (43%) | | | 15.0 (1.5 to 145.2), p = 0.02 | 9.9 (0.7 to 150.2), p = 0.09 |
| | <0.87 | 33 (56%) | 1 (7%) | | | | |
| | >0.87 | 26 (44%) | 13 (93%) | <0.01 | | 16.5 (2.02 to 134.5), p = 0.009 | 9.2 (0.9 to 95.3), p = 0.06 |
| Time Point 2 | | | | | | | |
| ProADM overall, median (IQR) | | 1.0 (0.8; 1.4) | 2.5 (1.4; 4.0) | <0.01 | 0.85 | 3.1 (1.5 to 6.4), p = 0.002 | 2.9 (1.2 to 6.9), p = 0.02 |
| Pro ADM cut offs, n (%) | <0.75 | 11 (22%) | 0 (0%) | | | NA | NA |
| | >0.75 | 28 (55%) | 4 (29%) | | | NA | NA |
| | >1.5 | 12 (24%) | 10 (71%) | | | NA | NA |
| | <0.87 | 21 (41%) | 0 (0%) | | | NA | NA |
| | >0.87 | 30 (59%) | 14 (100%) | <0.01 | | NA | NA |
| Pro ADM median cut off, n (%) | <1.1 | 32 (63%) | 2 (14%) | <0.01 | | | |
| | >1.1 | 19 (37%) | 12 (100%) | | | 10.1 (2.0 to 50.1), p = 0.005 | 9.3 (1.4 to 60.7), p = 0.02 |
| Time Point 3 | | | | | | | |
| ProADM overall, median (IQR) | | 0.9 (0.6; 1.3) | 3.8 (2.6; 8.3) | <0.01 | 0.94 | 3.7 (1.6 to 8.9), p = 0.003 | 3.5 (1.3 to 10.1); p = 0.02 |
| Pro ADM cut offs, n (%) | <0.75 | 16 (38%) | 0 (0%) | <0.01 | | NA | NA |
| | >0.75 | 19 (45%) | 1 (10%) | | | NA | NA |
| | >1.5 | 7 (17%) | 9 (90%) | | | NA | NA |
| | <0.87 | 21 (50%) | 0 (0%) | | | NA | NA |
| | >0.87 | 21 (50%) | 10 (100%) | <0.01 | | NA | NA |

TABLE 1-continued

Crude and adjusted association of overall pro ADM and cut-offs and in hospital mortality.

| Pro-ADM Time Point | Cut off nmol/l | Survivors N = 70 | Non-Survivors N = 17 | p-Value | AUC | Univariate OR (95% CI), p-value | Multivariate OR* (95% CI), p-value |
|---|---|---|---|---|---|---|---|
| Pro ADM median cut off, n (%) | <1.1 | 28 (67%) | 0 (0%) | <0.01 | | NA | NA |
| | >1.1 | 14 (33%) | 10 (100%) | | | NA | NA |
| | | | Time Point 4 | | | | |
| Pro ADM overall, median (IQR) | | 1.1 (0.7; 1.8) | 2.5 (1.6; 9.2) | <0.01 | 0.86 | 3.7 (0.8 to 16.7); p = 0.08 | 2.7 (0.9 to 7.9); p = 0.06 |
| Pro ADM cut offs, n (%) | <0.75 | 8 (26%) | 0 (0%) | 0.06 | | NA | NA |
| | >0.75 | 13 (42%) | 1 (17%) | | | NA | NA |
| | >1.5 | 10 (32%) | 5 (83%) | | | NA | NA |
| | <0.87 | 10 (32%) | 0 (0%) | | | NA | NA |
| | >0.87 | 21 (68%) | 6 (100%) | 0.1 | | NA | NA |
| Pro ADM median cut off, n (%) | <1.3 | 19 (61%) | 1 (17%) | 0.04 | | | |
| | >1.3 | 12 (39%) | 5 (83%) | | | 7.9 (0.8 to 76.3); p = 0.07 | 3.8 (0.3 to 53.6), p = 0.33 |

*adjusted for gender, age and age adjusted Carlson Index.

TABLE 2

Diagnostic Accuracy.

| Pro ADM cut offs | Sensitivity | Specificity | Positive predictive value | Negative predictive value |
|---|---|---|---|---|
| 0.75 nmol/l | 92.9 (95% CI 66.1 to 99.8) | 33.9 (95% CI 22.1 to 47.4) | 25.0 (95% CI 14.0 to 38.9) | 95.2 (95% CI 76.2 to 99.9) |
| 0.87 nmol/l | 92.9 (95% CI 66.1 to 99.8) | 55.9 (95% CI 42.4 to 68.8) | 33.3 (95% CI 19.1 to 50.2) | 97.1 (95% CI 84.7 to 99.9) |
| 1.5 nmol/l | 42.9 (95% CI 17.7 to 71.1) | 86.4 (95% CI 75.0 to 94.0) | 42.9 (95% CI 17.7 to 71.1) | 86.4% (95% CI 75.0 to 94.0) |
| 2.5 nmol/l | 21.4 (95% CI 4.7 to 50.8) | 98.3 (95% CI 90.9 to 100.0) | 98.3 (95% CI 90.9 to 100.0) | 84.1 (95% CI 73.3 to 91.8) |

Example 2: Mid-Regional Pro-Adrenomedullin, a Marker of Permeability and Endothelial Stability, in Patients with Confirmed COVID-19 Infection: Results from an Observational Study

Summary

Introduction: Pro-adrenomedullin (MR-proADM) is a vasoactive peptide with key roles in reducing vascular hyperpermeability and improving endothelial stability during infection. MR-proADM has shown promise in risk stratification of patients with sepsis, but there is a lack of clinical data about this marker in patients with COVID-19 infection.

Methods: We included consecutive hospitalized adult patients with confirmed SARS-CoV-2 infection at the Cantonal Hospital Aarau (Switzerland) between February and April 2020. We investigated the association of initial and follow-up MR-proADM levels with in-hospital mortality in logistic regression analysis and area under the ROC curve (AUC).

Results: Mortality in the 89 included patients was 19% (n=17). Median admission MR-proADM levels (nmol/) were almost 2-fold increased in non-survivors compared to survivors (1.3 (IQR 1.1 to 2.3) vs. 0.8 (IQR 0.7 to 1.1)) and showed good discrimination (AUC 0.78). The association of initial MR-proADM levels and mortality was independent of other prognostic indicators including gender and age-adjusted Charlson Comorbidity Index (adjusted odds ratio 5.47 (95% CI 1.40 to 21.36, p=0.015). For admission MR-proADM levels the optimal threshold regarding mortality was at 0.93 nmol/L with a sensitivity of 93% (negative predictive value 97.3) and a specificity of 60%. Kinetics of MR-proADM over the subsequent days of in-hospital treatment provided further prognostic information.

Conclusion: Increased levels of MR-proADM are associated with mortality attributable to COVID-19 infection and may help to better risk stratify patients on admission and during the hospital stay.

Introduction

The severe acute respiratory syndrome coronavirus 2 (SARS-CoV-2), a novel coronavirus, is currently affecting millions of people in the world. Coronavirus disease 2019 (COVID-19) caused by SARS-Cov-2, was declared as global pandemic on the 11 Mar. 2020 by the World Health Organization. COVID-19 is highly contagious, which also explains its rapid and worldwide expansion (22). Key mechanisms that may have a role in the pathophysiology of multi-organ injury secondary to infection with SARS-CoV-2 include direct viral toxicity, endothelial cell damage and thrombo-inflammation, dysregulation of the immune response, and dysregulation of the renin-angiotensin-aldosterone system (23). The increased incidence of cardiovascular and thromboembolic complications, immune cell deactivation and sepsis-like multiple organ failure suggests the involvement of multiple pathways. Preliminary evidence suggests that while around 80% of the patients show only mild upper respiratory tract infection symptoms, 15% progress to severe lower respiratory manifestations requiring hospital admittance, and 5% need intensive care unit treatment due to severe diseases progression, primarily characterized by pulmonary failure, sometimes showing a high level inflammation, and multi-organ failure (24). Besides protective and preventive measures to reduce and minimize large-scale outbreaks, a timely assessment of the individual risk profile of a patient presenting to the emergency department may help to improve early decisions about site-of-care and initiation of COVID-19 specific treatments. Having objective measures of a patient's risk for mortality early are thus important to prompt such measures. Herein, prognostic biomarkers may help to estimate a patient's individual risk and provide objective and measurable results within short time of a patient's hospital admission. Such markers may also improve our understanding of the pathophysiology behind COVID-19 infection and its adverse outcomes.

Whilst different cytokines and blood markers have been compared in patients with different severities of COVID-19 no study today has investigated the potential role of adrenomedullin (ADM) during the host response to COVID-19 (25). ADM and its mid-regional prohormone fragment MR-proADM has been linked to endothelial dysfunction and the risk for organ dysfunction in patients with sepsis and infection of the lung as it is directly related to the status of the endothelium (26-29). Previous research found MR-proADM to be an accurate marker for risk assessment in patients with pneumonia and sepsis and thereby improving clinical scores such as the sequential organ failure assessment score (SOFA-Score) (30). Therefore, MR-proADM is mostly used to improve the identification of organ dysfunction and disease progression to sepsis or septic shock (31). MR-proADM has also been shown to be a good predictor for short and long term mortality in patients with low-respiratory-tract infections and sepsis (32-34). Previously the MR-proADM cut-off of 0.87 nmol/L has been proposed in a large multinational study to best classify patients as low or high risk for mortality (35). Saeed et al. demonstrated in two cohorts that using a MR-proADM cut-off in patients with suspected infection presenting to the emergency department of 0.87 nmol/L can increase out-patient treatment by 15% and 16.6%, with decreased readmission rates and no increase in mortality (35). Our aim was to investigate the association of initial and follow-up levels of MR-proADM levels with mortality in patients with confirmed COVID-19 infection.

Methods

Study Design and Setting: This prospective observational study included all consecutively hospitalized adult patients (≥18 years) with a confirmed SARS-CoV-2 infection at the Cantonal Hospital Aarau (Switzerland) between Feb. 26, 2020 and Apr. 30, 2020. The study was approved by the ethical committee (EKZN, 2020-01306). Baseline data of our cohort was previously published in order to understand specific characteristics of this illness in the Swiss population during the initial time of the pandemic (36). In brief, the definition for a confirmed COVID-19 infection were typical clinical symptoms (e.g., respiratory symptoms with or without fever, and/or pulmonary infiltrates and/or anosmia/dysgeusia) together with a positive real-time reverse transcription polymerase chain reaction (RT-PCR) taken from nasopharyngeal swabs or lower respiratory tract specimens, according to the WHO guidance (37). All analyzed data were assessed as part of the clinical routine during the hospitalization (from admission to discharge/death).

Data collection: Clinical information, including sociodemographics and comorbidities, home medications and COVID-19-specific inpatient medication were assessed until hospital discharge or death and exported from the hospital electronic clinical information system. Experimental treatment was offered to all patients and included, for hospital ward patients, Hydroxychloroquine only (first line) and, Tocilizumab. Azithromycin was also used in patients transferred from France. For all patients the age-adjusted Charlson comorbidity index (38) and the Clinical Frailty Score (up to 9 points) (39) were calculated as part of the clinical routine. Comorbidities were also assessed through chart review and based on the ICD10 code. Further, patient outcomes including in-hospital mortality, admission to the intensive care unit (ICU), length of hospital stay (LOS) as well as length of ICU stay were collected by chart review. Laboratory test results were available according to clinical routine.

Study objective and endpoint: The objective of this study is to investigate the ability of MR-proADM to predict mortality in confirmed COVID-19 infection patients, in order to classify patients at high or low risk for mortality. The primary endpoint is all cause in-hospital mortality.

Measurements of MR-proADM: Plasma and serum samples on admission were collected in BD Vacutainer® Heparin and SST tubes. Routine left-over samples were immediately frozen at $-70°$ C. until assayed. Results from routine laboratory tests were recorded. Mid-regional pro-adrenomedullin (MR-proADM) was assessed in batch using a commercially available automated fluorescent sandwich immunoassay (KRYPTOR®, B.R.A.H.M.S Thermo Fisher Scientific. Germany), as described in detail elsewhere (40-41). Briefly, the immunoassay employs two polyclonal antibodies to the amino acids 45-92 of pre-pro-adrenomedullin, the MR-proADM and has a limit of detection (LOD) of 0.05 nmol/L (41). The functional assay sensitivity, defined as the MR-proADM concentration with an inter-assay coefficient of variation of <20%, was 0.25 nmol/L. Values for the analytes followed a Gaussian distribution in healthy individuals without significant differences between males and females (41). The laboratory technicians who measured MR-proADM were blinded to the characteristics of the patients and the characteristics of the study.

Different time points during hospitalization were analyzed, depending on the available data:

$T_0$ (hospital admission day→blood draw within 24 h from admission)

$T_1$ (day 3/day 4)

$T_2$ (day 5/day 6)

$T_3$ (day 7/day 8)

Statistical Analysis: Discrete variables are expressed as frequency (percentage) and continuous variables as medians with interquartile ranges (IQR) or mean with standard deviation (SD). Multivariate logistic regression model were used to examine the association of MR-proADM levels with the primary endpoint. As predefined, regression models were adjusted for gender and age-adjusted Charlson comorbidity Index. Odds ratios (OR) and corresponding 95% confidence intervals (CI) were reported as a measure of association and C-Statistics (area under the operating receiver curve (ROC-AUC) as a measure of discrimination. We also validated the prognostic value of different pre-defined MR-proADM cut-offs based on previous studies in other populations, namely 0.75 (27, 42), 0.87 (35), 1.5 (27, 42). Survival analysis and log rank test was used to compare in-hospital mortality according to different MR-proADM-cutoffs. Additionally, sensitivity, specificity, positive and negative predictive values of MR-proADM in predicting in-hospital mortality for different potential cut-offs. A two-sided p-value of <0.05 was considered significant. Statistical analysis was performed using Stata 15.1 (StataCorp, College Station, TX, USA).

Results

A total of 103 patients were hospitalized with of a confirmed COVID-19 infection at the Cantonal Hospital Aarau (Switzerland), whereby 29 were transferred from other hospitals (three cases from France, one case from the Canton Ticino, 25 cases from regional hospitals not accepting COVID-19 admissions or treatment at a tertiary care hospital was indicated). Several patients had to be excluded from the analysis due to declined general informed consent (n=4) or no available aliquots for biomarker analysis (n=9). One further patient had to be excluded from the analysis, since still hospitalized and the primary endpoint was not evaluable at the time point of the analysis. FIG. 1 provides an overview of the study flow.

Baseline Characteristics

Baseline characteristics including demographics, comorbidities as well as in-hospital treatment and in-hospital endpoints in the overall cohort and stratified according to the primary endpoint are summarized in Table 3. Median age was 67 years (IQR 58-74) and 35% (n=31) were female. A total of 22% (n=20) of patients were taking angiotensin-converting enzyme inhibitors at home, while 19% (n=17) had an angiotensin II receptor blockers prescription and few patients were taking corticosteroids or other immunosuppressive treatments. Patients had a high burden of comorbidities with a median age-adjusted Charlson comorbidity index of 3 points and a high median frailty score of 3 points. The most common comorbidities included hypertension (58%, n=52), chronic kidney disease (27%, n=24) and obesity (29%, n=26). Overall, 49% of patients received an experimental antiviral treatment (mostly Hydroxychloroquine, rarely Ritonavir-boosted Lopinavir). A total of 26% (n=23) of patients developed severe COVID-19 progression characterized by a need for ICU treatment, of whom 18 needed mechanical ventilation. Overall, patients hospitalized due to COVID-19 had a median length of stay (LOS) of 9.0 days (IQR 5.0-18.0). 19% (n=17) of the hospitalized patients reached the primary endpoint, defined as in-hospital mortality.

A majority of patients presented with high clinical severity, particularly regarding the respiratory system with a high respiratory rate and evidence of compromised oxygenation in blood gas analysis. There was also a modest increase in the inflammation marker C-reactive protein (CRP) (mean level at 88.5 mg/L) but low levels of procalcitonin (PCT) levels (0.11 µg/L).

Association of MR-proADM Levels and in-Hospital Mortality

Median admission MR-proADM levels were almost 2-fold increased in non-survivors compared to survivors (1.3 (IQR 1.1 to 2.3) vs. 0.8 (IQR 0.7 to 1.1). We found a strong association of MR-proADM levels at each of the analyzed time points and in-hospital mortality. These associations remained robust in the multivariate model adjusted for gender and age-adjusted Charlson comorbidity index (Table 4). Regarding discrimination, MR-proADM had high AUCs for each time point with highest results on time point 3 (day 5/6 of hospitalization) with an AUC of 0.92 compared with an AUC of 0.78 on admission.

Furthermore, diagnostic accuracy of MR-proADM in predicting in-hospital was analyzed for different cut-offs (Table 5). We found an optimal cut-off at 0.93 nmol/L which was close to the median within the analyzed cohort with a sensitivity of 92.9% (95% CI 66.1 to 99.8) and a specificity of 60% (95% CI 46.5 to 72.4). Further, the cut-off at 0.93 nmol/L showed an excellent negative predictive value with 97.3 (95% CI 85.5 to 99.9). Results were also similar for other previously proposed cut-offs (i.e., at 0.75 nmol/L and 0.87 nmol/L). The use of higher cut-offs such as 1.5 nmol/L and 2.5 nmol/L showed a low sensitivity (42.9% and 21.4%) but higher specificity and positive predictive values.

We also confirmed our analysis in a time to event survival analysis showing short time to death in patients with higher MR-proADM levels. We classified patients according to different cut-offs and the median of MR-proADM values (>1.5 nmol/l, >0.87 nmol/l and >0.93 nmol/l). Results were also significant in regard to log-rank testing (log-rank, p=0.014 for survival curve A, log-rank p=0.0014 for survival curve B and log-rank p=0.0004 for survival curve C in FIG. 2).

Kinetics of Serial Measurements of MR-proADM

The kinetic of the MR-proADM according to the primary endpoint is illustrated in FIG. 3. MR-proADM values in non-survivor were significantly higher compared to survivors at every measured time point. Further, in survivors, MR-proADM remained low during the analyzed timeframe, whereas in non-survivors MR-proADM showed a step-wise increase between baseline (time point 0) and day 5/6 of hospitalization (time point 2) and a slight decrease around day 7/8 (time point 3).

Discussion

The results of this prospective study involving patients with COVID-19 infection in the early phase of the pandemic are twofold. First, we found that levels of admission MR-proADM, a marker that reflects permeability and endothelial stability, are twofold increased in patients with a fatal outcome and are thus strongly associated with in-hospital mortality, also in statistical models adjusted for age, gender and comorbid-burden. Second, when looking at the kinetics of MR-proADM, we also found a further increase in its level in non-survivors while survivors have lower levels that remain low during follow-up. These results suggest that MR-proADM may be helpful in the early risk stratification and monitoring of patients with COVID-19.

Early identification of patients at high risk for adverse outcomes with confirmed COVID-19 is crucial in order to predict severe diseases progression and reduce COVID-19 associated mortality. Yet, prediction rules for patients individual risk profile as well as the ability to predict outcomes are still lacking. Whilst several pro-inflammatory cytokines and prognostic markers have already been investigated in patients with COVID-19, no study has examined the prognostic value of MR-proADM measurements for the identification of COVID-19 patients at high risk for mortality. Yet, MR-proADM holds great promise as a biomarker in COVID-19 as it plays a key role in reducing vascular permeability and promotes endothelial stability and integrity following severe infection, and thus may help in identifying patients at risk of COVID-19 induced endotheliitis. Indeed, a recent study investigating gene upregulation in patients with systemic capillary leak syndrome (SCLS), characterized by plasma leakage into peripheral tissue and transient episodes of hypotensive shock and edema, found that ADM was not only one of the most upregulated genes, but that subsequent application to endothelial cells resulted in a protective effect on vascular barrier function. (25) Herein, this study evaluated the prognostic performance of initial and follow-up measurements of MR-proADM in confirmed COVID-19 patients treated in a tertiary care hospital in Aarau, Switzerland. The analyzed data showed that MR-proADM is a strong predictor for in-hospital mortality, with a high discriminatory ability in patients with confirmed COVID-19. This results suggest that MR-proADM levels in conjunction with clinical evaluation and other laboratory findings may help to identify and classify patients presenting to the emergency department with low and high risk for adverse outcome.

The prognostic relevance of MR-proADM was already analyzed and proved in several prior studies investigating patients with community acquired pneumonia (CAP) (43-45), chronic obstructive pulmonary disease (COPD) (46, 47) and cardiovascular diseases (48, 49). Our analysis is in line with this research and further expands the field to COVID-19 disease, which is also a very severe illness with however a very particular pathophysiology involving different organ systems as demonstrated in recent studies. Interestingly, we also found that previously proposed cut-off level of 0.87 nmol/L had a very sensitivity and negative likelihood ratio to rule out mortality in COVID-19 patients, similar to a previous study (35). Also, similar to our analysis, Christ-Crain et al. showed that MR-proADM has a high prognostic accuracy with an AUC of 0.81 for the prediction of ICU mortality in patients with sepsis (40) in contrast, Suberviola et al. found only a moderate value for the prediction of hospital mortality in sepsis patients with an AUC of 0.62 (50). This conflicting results on the prognostic role of MR-proADM may be explained by differences in study population like patient characteristics, disease severity underlying diseases and infection as well as sample size of the analyzed patient population. Zhoue et al (51) showed that already existing risk scores like CRB-65 and qSOFA may be helpful to identity COVID-19 affected patients with a poor prognosis, but they include too many false-positive patients. Consequences are a higher than needed demand for often limited resources. In this respect, other studies have confirmed that MR-proADM is more accurate compared to risk scores used alone and that it can improve the accuracy of these scores when used in combination (30, 52). Further, MR-proADM can be easy performed by a biomarker assay compared to scores that are often complex to calculate.

We found an optimal cut-off at 0.93 nmol/L in our analyzed cohort that can be recommended for the assessment of disease severity, disease progression, risk for in-hospital mortality and also for decisions regarding patient disposition. This cut-off is very close to already defined and validated MR-proADM cut-offs at 0.75 nmol/L (27, 42) and at 0.87 nmol/L (35). Higher cut-offs between 1.5 nmol/L and 2.5 nmol/L had low sensitivity but fairly high positive prognostic values. An initial MR-proADM value below the defined cut-off within the first 24 hours after presentation to the ED can be interpreted as low risk for mortality and can predict a mild course of disease while MR-proADM value above the cut-off indicates a high risk for mortality and thus predict a severe course of disease. Therefore, physicians may choose to monitor patients more closely. With this classification hospital resources could potentially be used more efficiently by improve site-of-care decisions and early discharge of patients. This is essential, especially for regions where healthcare systems reach their maximum capacity during peaks of the COVID-19 pandemic.

Conclusion

In conclusion, this first study evaluating MR-proADM in patients with COVID-19 infection, confirms its high prognostic value regarding prediction of in-hospital mortality. When used in conjunction With clinical findings and results of other laboratory parameters during an initial risk assessment, MR-proADM may improve early risk stratification in this patient population. The strong prognostic value of MR-proADM in COVID-19 confirmed patients is of interest and warrants further investigation.

Tables of Example 2

TABLE 3

| Demographic data, comorbidities, in-hospital treatment and in-hospital endpoints in the study population | | | | |
|---|---|---|---|---|
| | Overall n = 89 | Survivors n = 72 | Non-Survivors n = 17 | p-value |
| Sociodemographics | | | | |
| Age [years], median (IQR) | 67.0 (56.0, 74.0) | 63.0 (55.5, 74.0) | 74.0 (69.0, 80.0) | <0.01 |
| Female gender, n (%) | 31 (35%) | 30 (42%) | 1 (6%) | <0.01 |
| Nationality, n (%) | | | | |
| France | 3 (4%) | 3 (4%) | 0 (0%) | 0.80 |
| Italy | 6 (7%) | 5 (7%) | 1 (6%) | |
| Switzerland | 56 (63%) | 46 (64%) | 10 (59%) | |
| Turkey | 4 (4%) | 4 (6%) | 0 (0%) | |
| Others | 20 (22%) | 14 (19%) | 6 (35%) | |

TABLE 3-continued

| | Overall n = 89 | Survivors n = 72 | Non-Survivors n = 17 | p-value |
|---|---|---|---|---|
| Demographic data, comorbidities, in-hospital treatment and in-hospital endpoints in the study population | | | | |
| Pre-esisting risk-factors and medication | | | | |
| Active smoker, n (%) | 6 (9%) | 5 (9%) | 1 (8%) | 0.95 |
| Corticosteriod use, n (%) | 2 (2%) | 1 (1%) | 1 (6%) | 0.26 |
| Imuunosuppressant, n (%) | 4 (4%) | 2 (3%) | 2 (12%) | 0.11 |
| Angiotensin converting enzyme-inhibitor, n (%) | 20 (22%) | 14 (19%) | 6 (35%) | 0.16 |
| Angiotensin II receptor blockers, n (%) | 17 (19%) | 13 (18%) | 4 (24%) | 0.61 |
| Pre-admission history | | | | |
| Symptom onset before admission [days], median (IQR) | 8.0 (5.0, 10.0) | 8.0 (4.0, 11.0) | 7.0 (5.0, 8.0) | 0.47 |
| Transfer from another Hospital, n (%) | 27 (30%) | 21 (29%) | 6 (35%) | 0.62 |
| Comorbidities | | | | |
| Age adjusted Charlson comorbidity Index, median (IQR) | 3.0 (2.0, 6.0) | 3.0 (2.0, 6.0) | 5.0 (3.0, 9.0) | <0.01 |
| Clinical frailty scale, median (IQR) | 3.0 (2.0, 4.0) | 3.0 (2.0, 4.0) | 3.0 (3.0, 4.0) | 0.27 |
| Cancer, n (%) | 9 (10%) | 5 (7%) | 4 (24%) | 0.04 |
| Hypertension, n (%) | 52 (58%) | 39 (54%) | 13 (76%) | 0.09 |
| Coronary artery disease, n (%) | 23 (26%) | 16 (22%) | 7 (41%) | 0.11 |
| Chronic heart failure, n (%) | 3 (3%) | 3 (4%) | 0 (0%) | 0.39 |
| Asthma, n (%) | 14 (16%) | 11 (15%) | 3 (18%) | 0.81 |
| COPD, n (%) | 7 (8%) | 4 (6%) | 3 (18%) | 0.10 |
| Obsturctive sleep apnea, n (%) | 12 (13%) | 9 (13%) | 3 (18%) | 0.58 |
| Solid organ transplant recipient, n (%) | 1 (1%) | 1 (1%) | 0 (0%) | 0.63 |
| Rheumatic disease, n (%) | 2 (2%) | 1 (1%) | 1 (6%) | 0.26 |
| Chronic kidney disease, n (%) | 24 (27%) | 16 (22%) | 8 (47%) | 0.04 |
| Obesity (BMI >30 kg/m$^2$), n (%) | 26 (29%) | 22 (31%) | 4 (24%) | 0.57 |
| Diabetes, n (%) | 21 (24%) | 17 (24%) | 4 (24%) | 0.99 |
| In-hospital treatment | | | | |
| Treatment specification, n (%) | | | | |
| Hydroxychloroquine | 36 (40%) | 27 (38%) | 9 (53%) | 0.04 |
| Hydroxychloroquine + azithromycin | 3 (3%) | 3 (4%) | 0 (0%) | |
| Hydroxychloroquine + Tocilizumab | 1 (1%) | 1 (1%) | 0 (0%) | |
| Lopinavir/ritonavir | 2 (2%) | 2 (3%) | 0 (0%) | |
| Tocilizumab | 2 (2%) | 0 (0%) | 2 (12%) | |
| Symptomatic treatment only | 45 (51%) | 39 (54%) | 6 (35%) | |
| Antibiotic treatment, n (%) | 38 (43%) | 25 (35%) | 13 (76%) | <0.01 |
| In-hospital endpoints | | | | |
| ICU care, n (%) | 23 (26%) | 16 (22%) | 7 (41%) | 0.11 |
| Need for mechanical ventilation, n (%) | 18 (78%) | 12 (75%) | 6 (86%) | 0.09 |
| Length of stay, median (IQR) | 9.0 (5.0, 18.0) | 9.0 (5.0, 12.5) | 15.0 (5.0, 24.0) | 0.08 |

Abbreviations:

BMI, Body-Mass-Index;

COPD, Chronic Obstructive Pulmonary Disease;

ICU, intensive care unit;

IQR, interquartile range

TABLE 4

Univariate and multivariate logistic regression analysis for
different MR-proADM cut-offs at different time points.

| | Survivors n = 72 | Non-Survivors n = 17 | p-value | AUC | Univariate OR (95% CI), p-value | Multivariate* OR (95% CI), p-value |
|---|---|---|---|---|---|---|
| MR-proADM Time point 0 (within 24 h from admission) | | | | | | |
| MR-proADM overall, median (IQR) | 0.8 (0.7, 1.1) | 1.3 (1.1, 2.3) | <0.01 | 0.78 | 3.22 (1.29, 8.06), p = 0.012 | 5.47 (1.40, 21.36), p = 0.015 |
| MR-proADM cut-off, n (%) | | | | | | |
| <0.75 | 20 (33%) | 1 (7%) | 0.02 | | Reference | Reference |
| >0.75 | 32 (53%) | 7 (50%) | | | 4.38 (0.50, 38.26), p = 0.182 | 3.59 (0.38, 33.95), p = 0.265 |
| >1.5 | 8 (13%) | 6 (43%) | | | 15.00 (1.55, 145.22), p = 0.019 | 14.39 (1.02, 202.25), p = 0.048 |
| MR-proADM 0.87-cut-offs, n (%) | | | | | | |
| <0.87 | 33 (55%) | 1 (7%) | <0.01 | | Reference | Reference |
| >0.87 | 27 (45%) | 13 (93%) | | | 15.89 (1.95, 129.31), p = 0.010 | 11.78 (1.23, 112.38), p = 0.032 |
| MR-proADM median-cutoff, n (%) | | | | | | |
| <0.93 | 36 (60%) | 1 (7%) | <0.01 | | Reference | Reference |
| >0.93 | 24 (40%) | 13 (93%) | | | 19.50 (2.39, 159.00), p = 0.006 | 14.40 (1.48, 139.83), p = 0.021 |
| MR-proADM Time point 1 (day 3/day 4 of hospitalization) | | | | | | |
| MR-proADM overall, median (IQR) | 1.0 (0.8, 1.5) | 2.5 (1.4, 4.0) | <0.01 | 0.84 | 2.84 (1.44, 5.60), p = 0.003 | 2.84 (1.34, 6.00), p = 0.006 |
| MR-proADM cut-offs, n (%) | | | | | | |
| <0.75 | 11 (21%) | 0 (0%) | <0.01 | | NA | NA |
| >0.75 | 28 (54%) | 4 (29%) | | | NA | NA |
| >1.5 | 13 (25%) | 10 (71%) | | | NA | NA |
| MR-proADM 0.87-cut-offs, n (%) | | | | | | |
| <0.87 | 21 (40%) | 0 (0%) | <0.01 | | NA | NA |
| >0.87 | 31 (60%) | 14 (100%) | | | NA | NA |
| MR-proADM median-cut-off, n (%) | | | | | | |
| <1.1 | 32 (62%) | 2 (14%) | <0.01 | | Reference | Reference |
| >1.1 | 20 (33%) | 12 (86%) | | | 9.60 (1.94, 47.44), p = 0.006 | 7.46 (1.35, 41.26), p = 0.021 |
| MR-proADM Time point 2 (day 5/day 6 of hospitalization) | | | | | | |
| MR-proADM overall, median (IQR) | 0.9 (0.6, 1.4) | 3.8 (2.6, 8.3) | <0.01 | 0.92 | 2.02 (1.22, 3.35), p = 0.006 | 1.94 (1.15, 3.26), p = 0.012 |
| MR-proADM cut-offs, n (%) | | | | | | |
| <0.75 | 16 (36%) | 0 (0%) | <0.01 | | NA | NA |
| >0.75 | 19 (43%) | 1 (10%) | | | NA | NA |
| >1.5 | 9 (20%) | 9 (90%) | | | NA | NA |
| MR-proADM 0.87-cut-offs, n (%) | | | | | | |
| <0.87 | 21 (48%) | 0 (0%) | | | NA | NA |
| >0.87 | 23 (52%) | 10 (100%) | <0.01 | | NA | NA |
| MR-proADM median- | | | | | | |

US 12,681,017 B2

85

TABLE 4-continued

Univariate and multivariate logistic regression analysis for different MR-proADM cut-offs at different time points.

| | Survivors n = 72 | Non-Survivors n = 17 | p-value | AUC | Univariate OR (95% CI), p-value | Multivariate* OR (95% CI), p-value |
|---|---|---|---|---|---|---|
| cut-off, n (%) | | | | | | |
| <1.1 | 28 (64%) | 0 (0%) | <0.01 | | NA | NA |
| >1.1 | 16 (36%) | 10 (100%) | | | NA | NA |
| MR-proADM Time point 3 (day 7/day 8 of hospitalization) | | | | | | |
| MR-proADM overall, median (IQR) | 1.3 (0.8, 1.8) | 2.5 (1.6, 9.2) | 0.01 | 0.82 | 1.29 (0.99, 1.67), p = 0.055 | 1.28 (0.97, 1.69), p = 0.087 |
| MR-proADM cut-offs, n (%) | | | | | | |
| <0.75 | 8 (24%) | 0 (0%) | 0.09 | | NA | NA |
| >0.75 | 13 (39%) | 1 (17%) | | | NA | NA |
| >1.5 | 12 (36%) | 5 (83%) | | | NA | NA |
| MR-proADM 0.87-cut-offs, n (%) | | | | | | |
| <0.87 | 10 (30%) | 0 (0%) | | | NA | NA |
| >0.87 | 23 (70%) | 6 (100%) | 0.1 | | NA | NA |
| MR-proADM median-cut-off, n (%) | | | | | | |
| <1.3 | 19 (58%) | 1 (17%) | 0.07 | | Reference | Reference |
| >1.3 | 14 (42%) | 5 (83%) | | | 6.79 (0.71, 64.72), p = 0.096 | 4.71 (0.45, 48.71), p = 0.194 |

*adjusted for, gender and age adjusted Charlson comorbidity Index.
Abbreviations:
AUC, area under the curve;
CI, confidence interval;
OR, odds ratio;
MR-proADM, pro-adrenomedullin.

TABLE 5

Diagnostic accuracy of different MR-proADM cut-offs at baseline.

| | Sensitivity (95% CI) | Specificity (95% CI) | Positive predictive value (95% CI) | Negative predictive value (95% CI) |
|---|---|---|---|---|
| MR-proADM cut-off values | | | | |
| 0.75 nmol/L | 92.9 (95% CI 66.1 to 99.8) | 33.3 (95% CI 22.7 to 46.7) | 24.5 (95% CI 13.8 to 38.3) | 95.2 (95% CI 76.2 to 99.9) |
| 0.87 nmol/L | 92.9 (95% CI 66.1 to 99.8) | 55.0 (95% CI 41.6 to 67.9) | 32.5 (95% CI 18.6 to 49.1) | 97.1 (95% CI 84.7 to 99.9) |
| 1.5 nmol/L | 42.9 (95% CI 17.7 to 71.1) | 86.7 (95% CI 75.4 to 94.1) | 42.9 (95% CI 17.7 to 71.1) | 86.7 (95% CI 75.4 to 94.1) |
| 2.5 nmol/L | 21.4 (95% CI 4.7 to 50.8) | 98.3 (95% CI 91.1 to 100.0) | 75.0 (95% CI 19.4 to 99.4) | 84.3 (95% CI 73.6 to 91.9) |
| MR-proADM-Median | | | | |
| 0.93 nmol/L | 92.9 (95% CI 66.1 to 99.8) | 60.0 (95% CI 46.5 to 72.4) | 35.1 (95% CI 20.2 to 52.5) | 97.3 (95% CI 85.8 to 99.9) |

86

1. https://www.mayoclinic.org/diseases-conditions/sars/symptoms-causes/syc-20351765
2. Vjaykrishna, D.; Smith, G. J.; Zhang, J. X.; Peiris, J. S.; Chen, H.; Guan, Y. Evolutionary insights into the ecology of coronaviruses. J. Virol. 2007, 81, 4012-4020.
3. Yuefei, J.; Haiyan, Y.; Wangquan, J.; Weidong, W; Shuaiyin, C.; Weiguo, Z; Guangcai, D. Virology, Epidemiology, Pathogenesis and Control of Covid-19. Viruses 2020, 12, 372.
4. Al-Tawfiq Asymptomatic Coronavirus Infection: MERS-CoV and SARS-CoV-2 (COVID-19). Travel Med Infect Dis. 2020 February (Epub)
5. Gu, J; Gong, E; Zhang, B: et al. Multiple organ infection and the pathogenesis of SARS. J Exp Med 2005 205 (3): 415-424
6. Fei Z.; Ting, Y; Ronghui, D; et al. Clinical course and risk factors for mortality of adult inpatients with COVID-19 in Wuhan, China: a retrospective cohort study. The Lancet 2020, 395:1054-1062
7. Temmesfeld-Wollbruck B, Brell B, David I, et al. Adrenomedullin reduces vascular hyperpermeability and improves survival in rat septic shock. Intensive Care Med. April 2007; 33(4):703-710.
8. Muller-Redetzky H C, Will D, Hellwig K, et al. Mechanical ventilation drives pneumococcal pneumonia into lung injury and sepsis in mice: protection by adrenomedullin. Crit Care. 2014; 18(2):R73.

9. Vallet B. Endothelial cell dysfunction and abnormal tissue perfusion. Crit Care Med. May 2002; 30(5 Suppl):S229-234.

10. Gonzalez-Rey E, Chomy A, Varela N, Robledo G, Delgado M. Urocortin and adrenomedullin prevent lethal endotoxemia by down-regulating the inflammatory response. Am J Pathol. Jun. 2006; 168(6):1921-1930.

11. Carrizo G J, Wu R, Cui X, Dwivedi A J, Simms H H, Wang P. Adrenomedullin and adrenomedullin-binding protein-1 downregulate inflammatory cytokines and attenuate tissue injury after gut ischemia-reperfusion. Surgery. February 2007; 141(2):245-253.

12. Brell B, Hippenstiel S, David I, et al. Adrenomedullin treatment abolishes ileal mucosal hypoperfusion induced by *Staphylococcus aureus* alpha-toxin—an intravital microscopic study on an isolated rat ileum Crit Care Med. December 2005; 33(12):2810-2016.

13. Brell B, Temmesfeld-Wollbruck B, Altzschner I, et al. Adrenomedullin reduces *Staphylococcus aureus* alpha-toxin-induced rat ileum microcirculatory damage. Crit Care Med. April 2005; 33(4):819-826.

14. Vigue B, Leblanc P E, Moati F, et al. Mid-regional pro-adrenomedullin (MR-proADM), a marker of positive fluid balance in critically ill patients: results of the ENVOL study. Crit Care. Nov. 9, 2016; 20(1):363.

15. Andaluz-Ojeda D, Cicuendez R, Calvo D, et al. Sustained value of proadrenomedullin as mortality predictor in severe sepsis. J Infect. July 2015; 71(1):136-139.

16. Hartmann O, Schuetz P, Albrich V C, Anker S D, Mueller B, Schmidt T. Time-dependent Cox regression: serial measurement of the cardiovascular biomarker proadrenomedullin improves survival prediction in patients with lower respiratory tract infection Int J Cardiol. Nov. 29, 2012; 161(3):166-173.

17. Albrich V C, Dusemund F, Ruegger K, et al. Enhancement of CURB65 score with proadrenomedullin (CURB65-A) for outcome prediction in lower respiratory tract infections: derivation of a clinical algorithm. BMC Infect Dis. 2011; 11:112.

18. Albrich V C, Ruegger K, Dusemund F, et al. Optimised patient transfer using an innovative multidisciplinary assessment in Kanton Aargau (OPTIMA I): an observational survey in lower respiratory tract infections. Swiss Med Wkly. 2011; 141:w13237.

19. Tyagi A, Sethi A K, Girotra G, Mohta M. The microcirculation in sepsis. Indian J Anaesth. June 2009; 53(3): 281-293.

20. Hemandez G, Bruhn A, Ince C. Microcirculation in sepsis: new perspectives. Curr Vasc Pharmacol. Mar. 1, 2013; 11(2):161-169.

21. Vijayanand, P.; Wilkins, E.; Woodhead, M.; Severe Acute Respiratory Syndrome (SARS): a review. Clin Med 2004; 4:152-60

22. Li R, Pei S, Chen B, et al. Substantial undocumented infection facilitates the rapid dissemination of novel coronavirus (SARS-CoV-2). Science 2020; 368(6490): 489-93.

23. Gupta A, Madhavan M V, Sehgal K, et al. Extrapulmonary manifestations of COVID-19.
Nature medicine 2020; 26(7): 1017-32.

24. Wu Z, McGoogan J M. Characteristics of and Important Lessons From the Coronavirus Disease 2019 (COVID-19) Outbreak in China: Summary of a Report of 72314 Cases From the Chinese Center for Disease Control and Prevention. JAMA: the journal of the American Medical Association 2020.

25. Wilson D C, Schefold J C, Baldira J, Spinetti T, Saeed K, Elke G. Adrenomedullin in COVID-19 induced endotheliitis. Crit Care 2020; 24(1): 411.

26. Valenzuela-Sanchez F, Valenzuela-Mendez B, Rodriguez-Gutierrez J F, Estella-Garcia A, Gonzalez-Garcia M A. New role of biomarkers: mid-regional pro-adrenomedullin, the biomarker of organ failure. Ann Transl Med 2016; 4(17): 329.

27. Kutz A, Hausfater P, Amin D, et al. The TRIAGE-ProADM Score for an Early Risk Stratification of Medical Patients in the Emergency Department—Development Based on a Multi-National, Prospective, Observational Study. PLoS One 2016; 11(12): e0168076.

28. Renaud B, Schuetz P, Claessens Y E, Labarere J, Albrich W, Mueller B. Proadrenomedullin improves Risk of Early Admission to ICU score for predicting early severe community-acquired pneumonia. Chest 2012; 142(6): 1447-54.

29. Labarere J, Schuetz P, Renaud B, Claessens Y E, Albrich W, Mueller B. Validation of a clinical prediction model for early admission to the intensive care unit of patients with pneumonia Academic emergency medicine: official journal of the Society for Academic Emergency Medicine 2012; 19(9): 993-1003.

30. Schuetz P, Wolbers M, Christ-Crain M, et al. Prohormones for prediction of adverse medical outcome in community-acquired pneumonia and lower respiratory tract infections. Crit Care 2010; 14(3): R106.

31. Elke G. Bloos F, Wilson D C, et al. The use of mid-regional proadrenomedullin to identify disease severity and treatment response to sepsis—a secondary analysis of a large randomised controlled trial. Critical care 2018; 22(1): 79.

32. Huang D T, Angus D C, Kellum J A, et al. Midregional proadrenomedullin as a prognostic tool in community-acquired pneumonia. Chest 2009; 136(3): 823-31.

33. Christ-Crain M, Morgenthaler N G, Stolz D. et al. Pro-adrenomedullin to predict severity and outcome in community-acquired pneumonia [ISRCTN04176397]. Crit Care 2006; 10(3): R96.

34. Kruger S, Ewig S, Giersdorf S, et al. Cardiovascular and inflammatory biomarkers to predict short- and long-term survival in community-acquired pneumonia: Results from the German Competence Network, CAPNETZ. Am J Respir Crit Care Med 2010; 182(11): 1426-34.

35. Saeed K, Wilson D C, Bloos F, et al. The early identification of disease progression in patients with suspected infection presenting to the emergency department: a multi-centre derivation and validation study. Critical care 2019; 23(1): 40.

36. Gregoriano C, Koch D, Haubitz S, et al. Characteristics, predictors and outcomes among 99 patients hospitalised with COVID-19 in a tertiary care centre in Switzerland: an observational analysis. Swiss medical weekly 2020; 150: w20316.

37. WHO. Clinical management of severe acute respiratory infection when novel coronavirus (nCov) infection is suspected; interim guidance, 25 Jan. 2020. Published Jan. 25, 2020.

38. Charlson M, Szatrowski T P, Peterson J, Gold J. Validation of a combined comorbidity index. J Clin Epidemiol 1994; 47(11): 1245-51.

39. Juma S, Taabazuing M M, Montero-Odasso M. Clinical Frailty Scale in an Acute Medicine Unit: a Simple Tool That Predicts Length of Stay. Can Geriatr J 2016; 19(2): 34-9.

40. Christ-Crain M, Morgenthaler N G, Struck J, Harbarth S, Bergmann A, Muller B. Mid-regional pro-adrenomedullin as a prognostic marker in sepsis: an observational study. Critical care 2005; 9(6): R816-24.

41. Morgenthaler N G, Struck J, Alonso C, Bergmann A. Measurement of midregional proadrenomedullin in plasma with an immunoluminometric assay. Clin Chem 2005; 51(10): 1823-9.

42. Albrich W C, Dusemund F, Ruegger K, et al. Enhancement of CURB65 score with proadrenomedullin (CURB65-A) for outcome prediction in lower respiratory tract infections: derivation of a clinical algorithm. BMC infectious diseases 2011; 11: 112.

43. Cavallazzi R, El-Kersh K, Abu-Atherah E, et al. Midregional proadrenomedullin for prognosis in community-acquired pneumonia: a systematic review. Respir Med 2014; 108(11): 1569-80

44. Gordo-Remartinez S, Calderon-Moreno M, Fernandez-Herranz J, et al. Usefulness of midregional proadrenomedullin to predict poor outcome in patients with community acquired pneumonia. PLoS One 2015; 10(6): e0125212.

45. Espana P P, Capelastegui A, Mar C, et al. Performance of pro-adrenomedullin for identifying adverse outcomes in community-acquired pneumonia. J Infect 2015; 70(5): 457-66.

46. Grolimund E, Kutz A, Marlowe R J, et al. Long-term Prognosis in COPD Exacerbation: Role of Biomarkers, Clinical Variables and Exacerbation Type. COPD 2015; 12(3): 295-305.

47. Schuetz P. Marlowe R J, Mueller B. The prognostic blood biomarker proadrenomedullin for outcome prediction in patients with chronic obstructive pulmonary disease (COPD): a qualitative clinical review. Clin Chem Lab Med 2015; 53(4): 521-39.

48. Shah K S, Marston N A, Mueller C, et al. Midregional proadrenomedullin predicts mortality and major adverse cardiac events in patients presenting with chest pain: results from the CHOPIN trial. Acad Emerg Med 2015; 22(5): 554-83.

49. Yuyun M F, Narayan H K, Ng L L. Prognostic significance of adrenomedullin in patients with heart failure and with myocardial infarction. Am J Cardiol 2015; 115(7): 986-91.

50. Suberviola B, Castellanos-Ortega A, Ruiz Ruiz A, Lopez-Hoyos M, Santibanez M. Hospital mortality prognostication in sepsis using the new biomarkers suPAR and proADM in a single determination on ICU admission. Intensive Care Med 2013; 39(11): 1945-52.

51. Zhou F, Yu T, Du R, et al. Clinical course and risk factors for mortality of adult inpatients with COVID-19 in Wuhan, China: a retrospective cohort study. Lancet 2020; 395(10229): 1054-62.

52. Legramante J M, Mastropasqua M, Susi B, et al. Prognostic performance of MR-pro-adrenomedullin in patients with community acquired pneumonia in the Emergency Department compared to clinical severity scores PSI and CURB. PloS one 2017; 12(11): e0187702.

The invention claimed is:

1. A method for reducing the risk of severe acute respiratory syndrome (SARS) progression in a patient that has SARS, wherein the patient is infected with a SARS-coronavirus, wherein the method comprises determining a level of mid-regional pro-adrenomedullin (MR-proADM) in a sample from the patient, wherein said level indicates the severity of SARS progression, comprising prognosing a subsequent adverse event in the health of the patient, wherein the patient has been diagnosed with SARS, wherein the level of MR-proADM indicates the likelihood of a subsequent adverse event in the health of said patient and treating said patient to reduce the risk of SARS progression, wherein the treatment comprises one or more of a transfer to a clinical setting for intensified treatment, hospitalization, an escalation of therapeutic interventions, symptomatic treatment, treatment to reduce fever and/or pain, anti-inflammatory treatment, antiviral treatment, antibiotic treatment, oxygen support, invasive mechanical ventilation, non-invasive mechanical ventilation, renal replacement therapy, vasopressor use, fluid therapy, extracorporeal blood purification and/or organ protection.

2. The method according to claim 1, further comprising therapy guidance, stratification and/or control for the patient, wherein the level of MR-proADM indicates whether the patient is at risk of SARS progression to a condition that requires intensified treatment and/or disease monitoring.

3. The method according to claim 1, wherein the patient exhibits symptoms of a severe acute respiratory syndrome (SARS) and/or symptoms of infection with a SARS-coronavirus.

4. The method according to claim 1, wherein the patient is infected with SARS-COV-2.

5. The method according to claim 1, wherein the patient belongs to a patient group with an increased risk of an adverse event in severe acute respiratory syndrome (SARS).

6. The method according to claim 1, wherein the method comprises:
   providing a sample from said patient,
   determining a level of MR-proADM in said sample,
   comparing the level of MR-proADM to a cut-off value,
      wherein said cut-off value is 0.93 nmol/l±20%,
   wherein a level of MR-proADM in said sample above the cut-off value indicates that the patient is at risk of SARS progression to a condition that requires intensified treatment and/or disease monitoring.

7. The method according to claim 6,
   wherein a level of MR-proADM in said sample above the cut-off value indicates that the patient is at risk of a SARS progression to a condition that requires hospitalization.

8. The method according to claim 1, wherein the patient shows mild or no symptoms of SARS or of infection with a SARS-coronavirus.

9. The method according to claim 1, wherein the adverse event in the health of said patient is death, respiratory failure, and/or organ failure.

10. The method according to claim 1, wherein a high severity level of MR-proADM determined in the sample is indicative of a subsequent adverse event, wherein the high severity level is above 2.25 nmol/l±20%.

11. The method according to claim 10, wherein the patient is an intensive care unit (ICU)-patient and a high severity level of MR-proADM indicates keeping said patient on the ICU and modifying the treatment of the patient in the ICU, or the patient is not an intensive care unit (ICU)-patient and the high severity level of MR-proADM indicates transferring said patient to an ICU.

12. The method according to claim 1, wherein the method comprises determining a level of MR-proADM in a sample from the patient obtained within 24 hours of hospital admission, wherein a level of or above 0.93 nmol/l±20% indicates the patient is at risk of SARS progression to a condition that requires intensified treatment and/or disease monitoring.

13. The method according to claim 1, wherein the patient is infected with SARS-COV-2.

14. The method according to claim 1, wherein the adverse event in the health of said patient is a deterioration of clinical symptoms requiring a focus cleaning procedure, transfusion of blood products, infusion of colloids, emergency surgery, invasive mechanical ventilation and/or renal or liver replacement.

15. The method according to claim 1, wherein the method further comprises determining a level of at least one additional biomarker in a sample from said patient.

16. The method according to claim 15, wherein the at least one additional biomarker is at least one of procalcitonin (PCT), lactate, creatine kinase (CK), lactate dehydrogenase (LDH), creatinine, myoglobin, aldolase, troponin, carbonic anhydrase type 3, fatty acid-binding protein (FABP), transaminases, potassium, arginine vasopressin (AVP), pro-arginine vasopressin (proAVP), Copeptin (CT-proAVP), Endothelin-1 (ET-1), C-terminal proendothelin-1 (CT-proET-1), and D-Dimer.

* * * * *

SEQUENCE LISTING

<160> NUMBER OF SEQ ID NOS: 11

<210> SEQ ID NO 1
<211> LENGTH: 185
<212> TYPE: PRT
<213> ORGANISM: Homo sapiens

<400> SEQUENCE: 1

```
Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175
```

-continued

Pro Ser Gly Ser Ala Pro His Phe Leu
            180                 185

<210> SEQ ID NO 2
<211> LENGTH: 48
<212> TYPE: PRT
<213> ORGANISM: Homo sapiens

<400> SEQUENCE: 2

Glu Leu Arg Met Ser Ser Ser Tyr Pro Thr Gly Leu Ala Asp Val Lys
1               5                   10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
        35                  40                  45

<210> SEQ ID NO 3
<211> LENGTH: 52
<212> TYPE: PRT
<213> ORGANISM: Homo sapiens

<400> SEQUENCE: 3

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 4
<211> LENGTH: 161
<212> TYPE: PRT
<213> ORGANISM: Homo sapiens

<400> SEQUENCE: 4

Met Asp Asp Ile Tyr Lys Ala Ala Val Glu Gln Leu Thr Glu Glu Gln
1               5                   10                  15

Lys Asn Glu Phe Lys Ala Ala Phe Asp Ile Phe Val Leu Gly Ala Glu
            20                  25                  30

Asp Gly Cys Ile Ser Thr Lys Glu Leu Gly Lys Val Met Arg Met Leu
        35                  40                  45

Gly Gln Asn Pro Thr Pro Glu Glu Leu Gln Glu Met Ile Asp Glu Val
    50                  55                  60

Asp Glu Asp Gly Ser Gly Thr Val Asp Phe Asp Glu Phe Leu Val Met
65                  70                  75                  80

Met Val Arg Cys Met Lys Asp Asp Ser Lys Gly Lys Ser Glu Glu Glu
            85                  90                  95

Leu Ser Asp Leu Phe Arg Met Phe Asp Lys Asn Ala Asp Gly Tyr Ile
            100                 105                 110

Asp Leu Asp Glu Leu Lys Ile Met Leu Gln Ala Thr Gly Glu Thr Ile
        115                 120                 125

Thr Glu Asp Asp Ile Glu Glu Leu Met Lys Asp Gly Asp Lys Asn Asn
    130                 135                 140

Asp Gly Arg Ile Asp Tyr Asp Glu Phe Leu Glu Phe Met Lys Gly Val
145                 150                 155                 160

-continued

```
Glu

<210> SEQ ID NO 5
<211> LENGTH: 210
<212> TYPE: PRT
<213> ORGANISM: Homo sapiens

<400> SEQUENCE: 5

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210

<210> SEQ ID NO 6
<211> LENGTH: 288
<212> TYPE: PRT
<213> ORGANISM: Homo sapiens

<400> SEQUENCE: 6

Met Ser Asp Ile Glu Glu Val Val Glu Glu Tyr Glu Glu Glu Glu Gln
1               5                   10                  15

Glu Glu Ala Ala Val Glu Glu Gln Glu Glu Ala Ala Glu Glu Asp Ala
            20                  25                  30

Glu Ala Glu Ala Glu Thr Glu Glu Thr Arg Ala Glu Glu Asp Glu Glu
        35                  40                  45

Glu Glu Glu Ala Lys Glu Ala Glu Asp Gly Pro Met Glu Glu Ser Lys
    50                  55                  60

Pro Lys Pro Arg Ser Phe Met Pro Asn Leu Val Pro Pro Lys Ile Pro
65                  70                  75                  80

Asp Gly Glu Arg Val Asp Phe Asp Asp Ile His Arg Lys Arg Met Glu
                85                  90                  95

Lys Asp Leu Asn Glu Leu Gln Ala Leu Ile Glu Ala His Phe Glu Asn
```

-continued 100                    105                    110

Arg Lys Lys Glu Glu Glu Glu Leu Val Ser Leu Lys Asp Arg Ile Glu
                115                    120                    125

Arg Arg Arg Ala Glu Arg Ala Glu Gln Gln Arg Ile Arg Asn Glu Arg
    130                    135                    140

Glu Lys Glu Arg Gln Asn Arg Leu Ala Glu Glu Arg Ala Arg Arg Glu
145                    150                    155                    160

Glu Glu Glu Asn Arg Arg Lys Ala Glu Asp Glu Ala Arg Lys Lys Lys
                165                    170                    175

Ala Leu Ser Asn Met Met His Phe Gly Gly Tyr Ile Gln Lys Gln Ala
                180                    185                    190

Gln Thr Glu Arg Lys Ser Gly Lys Arg Gln Thr Glu Arg Glu Lys Lys
                195                    200                    205

Lys Lys Ile Leu Ala Glu Arg Arg Lys Val Leu Ala Ile Asp His Leu
    210                    215                    220

Asn Glu Asp Gln Leu Arg Glu Lys Ala Lys Glu Leu Trp Gln Ser Ile
225                    230                    235                    240

Tyr Asn Leu Glu Ala Glu Lys Phe Asp Leu Gln Glu Lys Phe Lys Gln
                245                    250                    255

Gln Lys Tyr Glu Ile Asn Val Leu Arg Asn Arg Ile Asn Asp Asn Gln
                260                    265                    270

Lys Val Ser Lys Thr Arg Gly Lys Ala Lys Val Thr Gly Arg Trp Lys
                275                    280                    285

<210> SEQ ID NO 7
<211> LENGTH: 164
<212> TYPE: PRT
<213> ORGANISM: Homo sapiens

<400> SEQUENCE: 7

Met Pro Asp Thr Met Leu Pro Ala Cys Phe Leu Gly Leu Leu Ala Phe
1                    5                    10                    15

Ser Ser Ala Cys Tyr Phe Gln Asn Cys Pro Arg Gly Gly Lys Arg Ala
                20                    25                    30

Met Ser Asp Leu Glu Leu Arg Gln Cys Leu Pro Cys Gly Pro Gly Gly
                35                    40                    45

Lys Gly Arg Cys Phe Gly Pro Ser Ile Cys Cys Ala Asp Glu Leu Gly
    50                    55                    60

Cys Phe Val Gly Thr Ala Glu Ala Leu Arg Cys Gln Glu Glu Asn Tyr
65                    70                    75                    80

Leu Pro Ser Pro Cys Gln Ser Gly Gln Lys Ala Cys Gly Ser Gly Gly
                85                    90                    95

Arg Cys Ala Ala Phe Gly Val Cys Cys Asn Asp Glu Ser Cys Val Thr
                100                    105                    110

Glu Pro Glu Cys Arg Glu Gly Phe His Arg Arg Ala Arg Ala Ser Asp
                115                    120                    125

Arg Ser Asn Ala Thr Gln Leu Asp Gly Pro Ala Gly Ala Leu Leu Leu
    130                    135                    140

Arg Leu Val Gln Leu Ala Gly Ala Pro Glu Pro Phe Glu Pro Ala Gln
145                    150                    155                    160

Pro Asp Ala Tyr

<210> SEQ ID NO 8
<211> LENGTH: 145
<212> TYPE: PRT

<213> ORGANISM: Homo sapiens

<400> SEQUENCE: 8

```
Cys Tyr Phe Gln Asn Cys Pro Arg Gly Gly Lys Arg Ala Met Ser Asp
1               5                   10                  15

Leu Glu Leu Arg Gln Cys Leu Pro Cys Gly Pro Gly Gly Lys Gly Arg
            20                  25                  30

Cys Phe Gly Pro Ser Ile Cys Cys Ala Asp Glu Leu Gly Cys Phe Val
            35                  40                  45

Gly Thr Ala Glu Ala Leu Arg Cys Gln Glu Glu Asn Tyr Leu Pro Ser
        50                  55                  60

Pro Cys Gln Ser Gly Gln Lys Ala Cys Gly Ser Gly Gly Arg Cys Ala
65                  70                  75                  80

Ala Phe Gly Val Cys Cys Asn Asp Glu Ser Cys Val Thr Glu Pro Glu
                85                  90                  95

Cys Arg Glu Gly Phe His Arg Arg Ala Arg Ala Ser Asp Arg Ser Asn
                100                 105                 110

Ala Thr Gln Leu Asp Gly Pro Ala Gly Ala Leu Leu Leu Arg Leu Val
            115                 120                 125

Gln Leu Ala Gly Ala Pro Glu Pro Phe Glu Pro Ala Gln Pro Asp Ala
    130                 135                 140

Tyr
145
```

<210> SEQ ID NO 9
<211> LENGTH: 9
<212> TYPE: PRT
<213> ORGANISM: Homo sapiens

<400> SEQUENCE: 9

```
Cys Tyr Phe Gln Asn Cys Pro Arg Gly
1               5
```

<210> SEQ ID NO 10
<211> LENGTH: 39
<212> TYPE: PRT
<213> ORGANISM: Homo sapiens

<400> SEQUENCE: 10

```
Ala Ser Asp Arg Ser Asn Ala Thr Gln Leu Asp Gly Pro Ala Gly Ala
1               5                   10                  15

Leu Leu Leu Arg Leu Val Gln Leu Ala Gly Ala Pro Glu Pro Phe Glu
            20                  25                  30

Pro Ala Gln Pro Asp Ala Tyr
        35
```

<210> SEQ ID NO 11
<211> LENGTH: 93
<212> TYPE: PRT
<213> ORGANISM: Homo sapiens

<400> SEQUENCE: 11

```
Ala Met Ser Asp Leu Glu Leu Arg Gln Cys Leu Pro Cys Gly Pro Gly
1               5                   10                  15

Gly Lys Gly Arg Cys Phe Gly Pro Ser Ile Cys Cys Ala Asp Glu Leu
            20                  25                  30

Gly Cys Phe Val Gly Thr Ala Glu Ala Leu Arg Cys Gln Glu Glu Asn
        35                  40                  45
```

-continued

```
Tyr Leu Pro Ser Pro Cys Gln Ser Gly Gln Lys Ala Cys Gly Ser Gly
    50              55              60

Gly Arg Cys Ala Ala Phe Gly Val Cys Cys Asn Asp Glu Ser Cys Val
65              70              75              80

Thr Glu Pro Glu Cys Arg Glu Gly Phe His Arg Arg Ala
                85              90
```